US012285487B2

(12) United States Patent
Jordan et al.

(10) Patent No.: US 12,285,487 B2
(45) Date of Patent: Apr. 29, 2025

(54) LIQUID TOPICAL PHARMACEUTICAL NANO-EMULSION FORMULATIONS

(71) Applicant: JRX BIOTECHNOLOGY, INC., Newport Beach, CA (US)

(72) Inventors: Frederick L. Jordan, Santa Ana, CA (US); Chris Jordan, Santa Ana, CA (US)

(73) Assignee: JRX Biotechnology, Inc., Newport Beach, CA (US)

( * ) Notice: Subject to any disclaimer, the term of this patent is extended or adjusted under 35 U.S.C. 154(b) by 667 days.

(21) Appl. No.: 16/575,056

(22) Filed: Sep. 18, 2019

(65) Prior Publication Data

US 2020/0009257 A1 Jan. 9, 2020

Related U.S. Application Data

(62) Division of application No. 14/655,238, filed as application No. PCT/US2013/077985 on Dec. 27, 2013, now abandoned.

(60) Provisional application No. 61/758,726, filed on Jan. 30, 2013, provisional application No. 61/748,036, filed on Dec. 31, 2012.

(51) Int. Cl.
| | | |
|---|---|---|
| *A61K 47/44* | (2017.01) | |
| *A61K 9/00* | (2006.01) | |
| *A61K 9/107* | (2006.01) | |
| *A61K 9/14* | (2006.01) | |
| *A61K 31/167* | (2006.01) | |
| *A61K 31/192* | (2006.01) | |
| *A61K 31/616* | (2006.01) | |
| *A61K 38/28* | (2006.01) | |
| *A61K 47/10* | (2017.01) | |
| *A61K 47/38* | (2006.01) | |
| *A61K 38/00* | (2006.01) | |

(52) U.S. Cl.
CPC ............ *A61K 47/44* (2013.01); *A61K 9/0014* (2013.01); *A61K 9/1075* (2013.01); *A61K 9/14* (2013.01); *A61K 31/167* (2013.01); *A61K 31/192* (2013.01); *A61K 31/616* (2013.01); *A61K 38/28* (2013.01); *A61K 47/10* (2013.01); *A61K 47/38* (2013.01); *A61K 38/00* (2013.01)

(58) Field of Classification Search
None
See application file for complete search history.

(56) References Cited

U.S. PATENT DOCUMENTS

| | | |
|---|---|---|
| 4,374,766 A | 2/1983 | Puchalski et al. |
| 4,973,473 A | 11/1990 | Schneider et al. |
| 5,126,331 A | 6/1992 | Gazzani |
| 5,153,174 A | 10/1992 | Band et al. |
| 5,318,960 A | 6/1994 | Toppo |
| 5,431,924 A | 7/1995 | Ghosh et al. |
| 5,472,713 A | 12/1995 | Fein et al. |
| 5,571,671 A | 11/1996 | Potter |
| 5,614,212 A | 3/1997 | D'Angelo et al. |
| 5,665,378 A | 9/1997 | Davis et al. |
| 5,708,038 A | 1/1998 | Davis |
| 5,716,625 A | 2/1998 | Hahn et al. |
| 5,744,368 A | 4/1998 | Goldgaber et al. |
| 5,837,853 A | 11/1998 | Takashima et al. |
| 5,840,746 A | 11/1998 | Ducharme et al. |
| 5,849,334 A | 12/1998 | Rivlin |
| 5,861,268 A | 1/1999 | Tang et al. |
| 5,885,597 A | 3/1999 | Botknecht et al. |
| 5,891,651 A | 4/1999 | Roche et al. |
| 5,891,857 A | 4/1999 | Holt et al. |
| 5,939,082 A | 8/1999 | Oblong et al. |
| 5,958,384 A | 9/1999 | Holick |
| 5,993,846 A | 11/1999 | Friedman et al. |
| 6,004,566 A | 12/1999 | Friedman et al. |
| 6,103,246 A | 8/2000 | Tisdale et al. |
| 6,113,921 A * | 9/2000 | Friedman ............... A61P 25/22 514/939 |
| 6,375,960 B1 | 4/2002 | Simonnet et al. |

(Continued)

FOREIGN PATENT DOCUMENTS

| | | |
|---|---|---|
| CN | 1245394 A | 2/2000 |
| CN | 1874740 | 12/2006 |

(Continued)

OTHER PUBLICATIONS

Office Action Dated Jun. 1, 2020 issued in Korean Patent Application No. 10-2015-7019652.
U.S. Appl. No. 11/412,182, filed Aug. 24, 2006, Frederick L. Jordan. Aloe Laboratories, "Manufacturing Procedures, Product :Regular Traditional Hand Fillet Aloe Vera Juice," 1 page, date unknown.
Amadio et al., "Nonsteroidal anti-inflammatory drugs," Postgraduate Medicine, 93(4): 73-97 (1993).
Barel and Clarys, "Study of the Stratum Corneum Barrier Function by Transepidermal Water Loss Measurements: Comparison between Two Commercial Instruments," Skin Pharmacol., 8:186-195.
Biomedical Information Services, Ltd., "Inspection Criteria," General Standard for Testing Purity of Aloe Vera, 7 pages, Copyright 1996.

(Continued)

Primary Examiner — Jennifer Chin
(74) Attorney, Agent, or Firm — Knobbe, Martens, Olson & Bear, LLP

(57) ABSTRACT

Aspects of the present invention are directed to compositions that are useful for delivery of an active ingredient to a subject. Some embodiments are formulated with an active ingredient, including, for example, a non-steroidal anti-inflammatory drug (NSAID), such as aspirin, ibuprofen, ketoprofen, or naproxen, acetaminophen, or a polypeptide or protein, such as insulin, wherein the active ingredient is stabilized and greater than 90% of the particles of the active ingredient have a particle size that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, or smaller, as determined by Dynamic Light Scattering (DLS), using a volume-weighted particle size distribution calculation method.

14 Claims, 16 Drawing Sheets

(56) References Cited

U.S. PATENT DOCUMENTS

| | | |
|---|---|---|
| 6,416,722 B1 | 7/2002 | Izutsu et al. |
| 6,444,234 B1 | 9/2002 | Kirby et al. |
| 6,645,507 B2 | 11/2003 | Bettle et al. |
| 6,759,056 B2 | 7/2004 | Jordan |
| 6,787,152 B2 | 9/2004 | Kirby et al. |
| 6,946,144 B1 | 9/2005 | Jordan |
| 7,201,919 B2 | 4/2007 | Jordan |
| 7,220,427 B2 | 5/2007 | Jordan |
| 7,300,666 B2 | 11/2007 | Jordan |
| 7,316,820 B2 | 1/2008 | Jordan |
| 7,371,738 B2 | 5/2008 | Mohapatra et al. |
| 2003/0104040 A1 | 6/2003 | Kirby et al. |
| 2003/0152626 A1 | 8/2003 | Lang et al. |
| 2004/0170676 A1 | 9/2004 | Jordan |
| 2004/0202709 A1 | 10/2004 | Kirby et al. |
| 2005/0019384 A1 | 1/2005 | Jordan |
| 2005/0271752 A1 | 12/2005 | Roth |
| 2006/0046962 A1 | 3/2006 | Meezan et al. |
| 2006/0121103 A1 | 6/2006 | Kirby et al. |
| 2006/0182771 A1 | 8/2006 | Dor et al. |
| 2006/0188531 A1 | 8/2006 | Jordan |
| 2006/0188532 A1 | 8/2006 | Jordan |
| 2006/0193901 A1 | 8/2006 | Jordan |
| 2007/0264346 A1 | 11/2007 | Guimberteau |
| 2007/0264349 A1 | 11/2007 | Lee et al. |
| 2008/0064640 A1 | 3/2008 | Jordan |
| 2008/0154210 A1* | 6/2008 | Jordan ............... A61K 31/7008 514/12.3 |
| 2010/0086611 A1 | 4/2010 | Rabinow et al. |
| 2011/0159104 A1 | 3/2011 | Teslenko |
| 2011/0117187 A1 | 5/2011 | Stock et al. |
| 2011/0166530 A1 | 7/2011 | Kreiner et al. |

FOREIGN PATENT DOCUMENTS

| | | |
|---|---|---|
| CN | 102389401 | 3/2012 |
| KR | 10-2007-0034451 | 3/2007 |
| WO | WO 92/08470 | 5/1992 |
| WO | WO 97/09992 A1 | 3/1997 |
| WO | WO 97/25023 A1 | 7/1997 |
| WO | WO 98/03163 | 1/1998 |
| WO | WO 98/29085 | 7/1998 |
| WO | WO 98/33474 | 8/1998 |
| WO | WO 98/34629 | 8/1998 |
| WO | WO 99/06024 | 2/1999 |
| WO | WO 99/44584 | 9/1999 |
| WO | WO 99/56727 | 11/1999 |
| WO | WO 00/02601 | 1/2000 |
| WO | WO 2005/039464 | 5/2005 |
| WO | WO 2005/039464 A1 | 5/2005 |
| WO | WO 2006/041538 | 4/2006 |
| WO | WO 2009/019604 | 2/2009 |

OTHER PUBLICATIONS

Botanical.com, "Frankincense," 3 pages, date unknown, http://www.botanical.com/botanical/mgmh/f/franki31.html.
Bronaugh and Collier, "In Vitro Percutaneous Absorption Studies: Principle, Fundamentals, and Applications," eds., Bronaugh and Maibach, Bock Raton, Fl., CRC Press pp. 237-241 (1991).
Chattem Inc., Packaging—"Flexall QuickGel," Copyright 1999.
Cohen et al., in "Wound Healing/Biochemical and Clinical Aspects," 1st ed. WB Saunders, Philadelphia (1992).
Collier et al., "Maintenance of Skin Viability During In vitro Percutaneous Absorption/Metabolism Studies" Toxicology and Applied Pharmacology, 99:522-533 (1989).
Croda, "Guide to Specialty Ingredients for the Personal Care Industry," pp. i-iii and 1-42 (2000).
Cummings, et al., "A Natural Alternative: Jojoba esters are a New Category of Naturally Derived, Oil Free Emollients that Offer Good Properties for a Wide Variety of Cosmetic Products," SPC Asia, (May 1999): 4 pages.
Cummings, et al., "In a Nutshell,": 3 pages.
David Julian McClements, (2011), "Edible nanoemulsions: fabrication, properties, and functional performance", Soft Matter, 7: 2297-2316.
Downing et al., Dermatology in General Medicine, pp. 185-190 (1993).
Flick, E.W. (1991). Cosmetics Additives—An Industrial Guide. William Andrew Publishing/Noyes. Online version available at: http://knovel.com/web/portal/browse/display?_EXT_KNOVEL_DISPLAY_bookid=581&VerticalID=0.
Floraesters® International Flora Technologies. Product Specification for Floraesters® 20: 1 page.
Floraesters® International Flora Technologies. Product Specification for Floraesters® 30: 1 page.
Floraesters® International Flora Technologies. Product Specification for Floraesters® 60: 1 page.
Floraesters® International Flora Technologies. Product Specification for Floraesters® 70: 1 page.
Floraesters® International Flora Technologies. Product Specification for Florasolvs® PEG-10 Sunflower: 1 page.
Floraesters® International Flora Technologies. Product Specification for Florasun® 90, Refined, Bleached, Winterized, Deodorized: 1 page.
Floraesters® International Flora Technologies. Product Specification for floraesters® IPJ: 1 page.
Floraesters® International Flora Technologies. Product Specification for Floraesters® HIPJ: 1 page.
Floraesters® International Flora Technologies. Product Specification for Florabeads®, Jojoba 40/60: 1 page.
Floraesters® International Flora Technologies. Product Specification for Florabeads®, Jojoba White 60/100: 1 page.
Floraesters® International Flora Technologies. Product Specification for Florasolvs® PEG-80 Jojoba: 1 page.
Floraesters® International Flora Technologies. Product Specification for Florasolvs® PEG-120 Jojoba: 1 page.
Floraesters® International Flora Technologies. Product Specification for Floraesters® Jojoba Oil, Pasteurized, Not Refined: 1 page.
Floraesters® International Flora Technologies. Product Specification for Floraesters® 15: 1 page.
Floraesters® International Flora Technologies. Product Specification for Florabeads®, Jojoba 28/60, 1 of 2: 1 page.
Floraesters® International Flora Technologies. Product Specification for Florabeads®, Jojoba 28/60, 2 of 2: 1 page.
Grindlay and Reynolds, "The Aloe Vera Phenomenon: A Review of the Properties and Modern Uses of the Leaf Parenchyma Gel," J. of Ethnopharmacology, 16:117-151 (1986).
Hart et al., "Two Functionally and Chemically Distinct Immunomodulatory Compounds in the Gel of Aloe Vera," J. of Ethnopharmacology, 23:61-71 (1988).
Hirata et al., "Biologically Active Constituents of Leaves and Roots of the Aloe Vera *Arborescens* var. *natalensis*," Z. Naturforsch, 32c:731-734 (1977).
International Aloe Science Council, Inc., "The Datasheet—100% Pure Aloe Vera," 1 page, date unknown.
International Preliminary Report on Patentability from PCT/US2013/077985 dated Jul. 9, 2015.
International Search Report and Written Opinion from PCT/US2013/077985 dated Jun. 24, 2014.
International Search Report issued on the related PCT Application No. PCT/US99/15409, Jan. 13, 2000.
International Search Report issued on the related PCT Application No. PCT/US2004/017169, dated Feb. 23, 2005.
International Search Report issued on the related PCT Application No. PCT/US2005/19017, dated Mar. 20, 2007.
Melaslow™, Brightening Cream with Melaslow™, SC-306, product formula: 2 pages.
Melaslow™, Skin Lightening Age Spot Treatment, product specification and claim substantiation: 2 pages.
Nature's Plus, "Search Results: Boswellic", 1 page, date unknown, http://www.natplus.com/products/productNumber=7124.
Nelson et al., "Mid-Infrared Laser Ablation of Stratum Corneum Enhances in Vitro Percutaneous Transport of Drugs," The Society for Investigative Dermatology, Inc., pp. 874-879 (1991).

(56) References Cited

OTHER PUBLICATIONS

O'Malley et al., "Emu Products, Increasing Production and Profitability," Rural Industries Research & Development Corporation, pp. i-110, Dec. 1999.
Office Action (1st Final) Issued on Aug. 29, 2007 in the U.S. Appl. No. 11/412,182.
Office Action (2nd Final) Issued on Aug. 24, 2009 in the U.S. Appl. No. 11/412,182.
Office Action issued on Apr. 4, 2008 in the U.S. Appl. No. 11/931,288.
Office Action issued on Aug. 4, 2009 in the U.S. Appl. No. 11/931,288.
Office Action issued on Feb. 20, 2008 in Chinese Patent Application No. 2004800320502, Feb. 20, 2008.
Office Action Issued on Jan. 8, 2009 in the U.S. Appl. No. 11/412,182.
Office Action issued on Jun. 10, 2010 in the U.S. Appl. No. 11/597,700.
Office Action issued on Jun. 20, 2013 in the U.S. Appl. No. 11/597,700.
Office Action issued on Mar. 3, 2011 in the U.S. Appl. No. 11/597,700.
Office Action Issued on May 22, 2008 in the U.S. Appl. No. 11/412,182.
Office Action issued on Oct. 30, 2008 in the U.S. Appl. No. 11/931,288.
Office Action Issued on Sep. 14, 2006 in the U.S. Appl. No. 11/412,182.
Pamphlet—Certificate of Analysis for Florasolvs® PEG-16 Macadamia, Jun. 2001.
Pamphlet—Life Extension™, Apr. 2002.
Pamphlet—*The mighty macadamia*, SPC Asia, Mar. 2000.
Ponec, M., "Epidermal lipids in vivo," The Keratinocyte Handbook, Leigh et al., eds, pp. 351-363 (1994).
Sederma, Etioline, product brochure, pp. 1-16 (Oct. 1996).
Sederma, Ichtyocollagene, product brochure, pp. 1-19 (Aug. 1993).
Sederma, Matrixyl "The physiological reconstruction of the matrix structures of the dermis to reduce deep and medium wrinkles: tested in vivo on a panel of 35 subjects during 2-4-6 months," product brochure, synopsis and pp. 1-44 (Sep. 1999).
Sederma, Melaslow™ "Lightens the complexion/Decreases age spots," product brochure, overview and pp. 1-28 (Dec. 2000).
Taguchi et al., "Enhancement of Propylene Glycol Distribution in the Skin by High Purity cis-Unsaturated Fatty Acids with Different Alkyl Chain Lengths Having Different Double Bond Position," Biol. Pharm. Bull., 22(4):407-411 (1999).
Woodin, L., "Cutting Postop Pain," RN, pp. 26-33 (1993).
Office Action issued on Oct. 3, 2017 in Japanese Patent Application No. 2015-550799.
Office Action dated May 17, 2017 issued in Chinese Patent Application No. 201380074085.1, filed Aug. 28, 2015.
Office Action including Search Report and Written Opinion issued on Nov. 1, 2016 in Singapore Patent Application No. 11201505076U.
Office Action dated Oct. 26, 2016 issued in Eurasian Patent Application No. 201591015, filed Jun. 23, 2015.
Extended Search Report dated Aug. 26, 2016 issued in European Patent Application No. 13869707.3, filed Jul. 3, 2015.
Yuan et al., "Investigation of microemulsion system for transdermal delivery of meloxicam" International Journal of Pharmaceuticals 321 (2006) 117-123.
Leica Microsystems, "New Labeling Tools Can Help to Realize the Full Potential of Super-Resolution Microscopy", accessed from: https://www.leica-microsystems.com/science-lab/new-labeling-tools-can-help-to-realize-the-full-potential-of-super-resolution-microscopy/; pp. 1-10 (Year: 2013).
Cosmetic Ingredient Review, "Safety Assessment of PEGylate Alkyl Glycerides as Used in Cosmetics", accessed from: "https://www.cir-safety.org/sites/default/files/peg_glycerides.pdf", pp. 1 and 28 (Year: 2014).
Examination Report issued on Nov. 8, 2019 in Singaporean Patent Application No. 11201505076U filed Dec. 27, 2013.
Office Action Dated May 13, 2020 issued in European Patent Application No. 13869707.3.
Brazilian Office Action of Apr. 28, 2022 for Brazilian Patent Application No. BR 11 2015 015788 2.

* cited by examiner

FIGURE 1A. Contact angle using Quartz Plate as Substrate - Water.
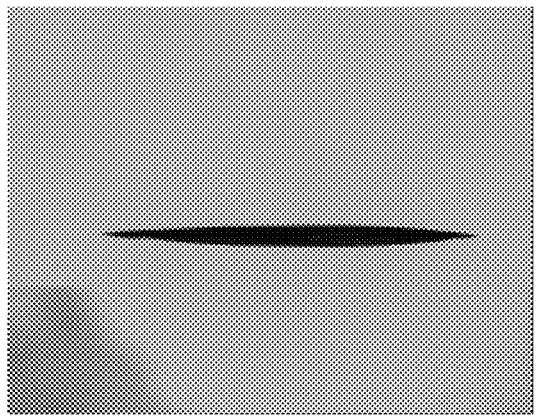
FIGURE 1B. Contact angle using Quartz Plate as Substrate - DermXTM Direct "Liquid Aspirin".
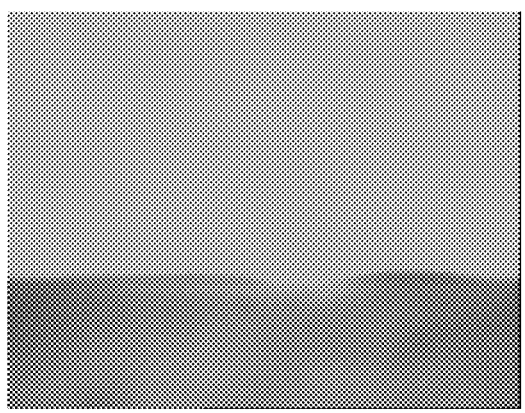

FIGURE 2A. Photomicrograph of Spreading using Quartz Plate as Substrate – Water. Each grid division equals 2 mm.
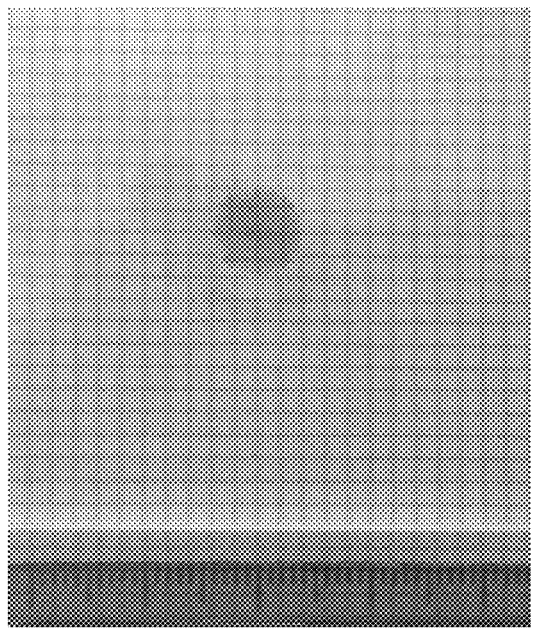
FIGURE 2B. Photomicrograph of Spreading using Quartz Plate as Substrate – DermX™ Direct "Liquid Aspirin". Each grid division equals 2 mm.
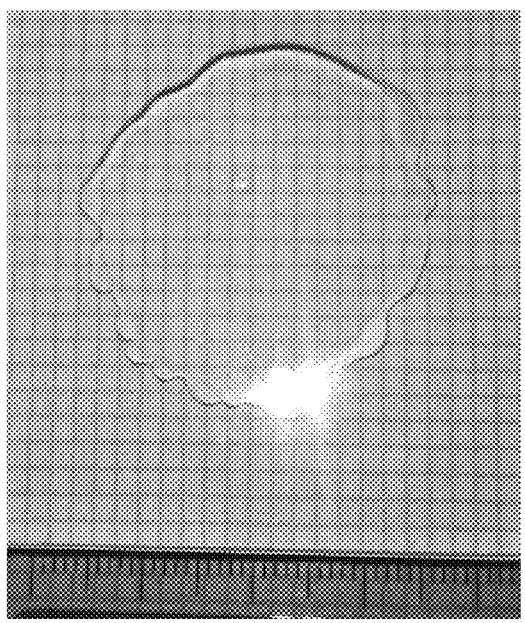

FIGURE 3A: Optical Image of Acetominophen dry powder (400X magnification).
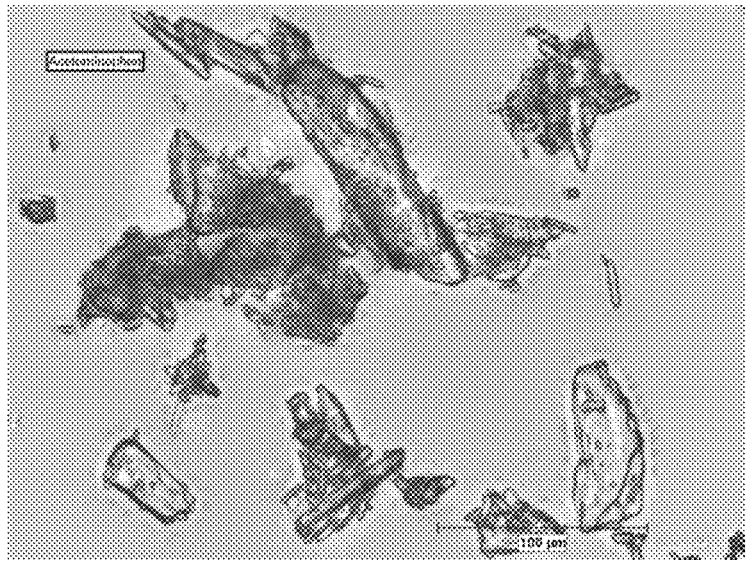
FIGURE 3B: Particle Size Distribution of Acetominophen suspension.
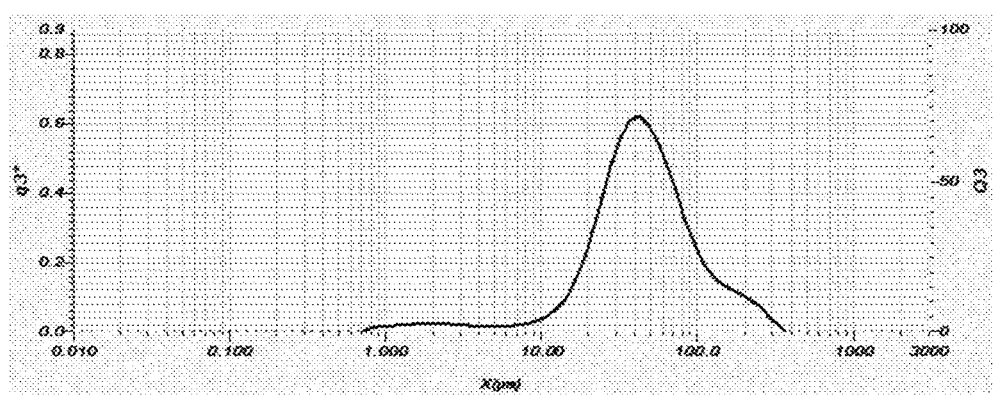

FIGURE 3C: Particle Size Distribution of "Liquid Acetominophen".
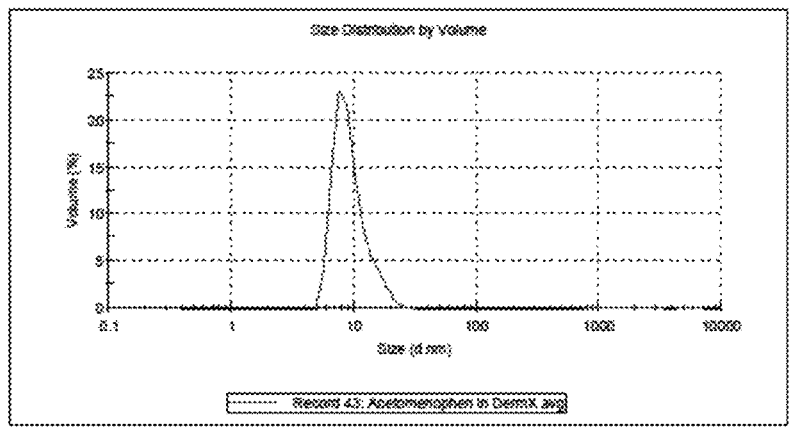
FIGURE 3D: Particle Size Distribution of the DermX™ Megaspheres™ carrier system ("Placebo").
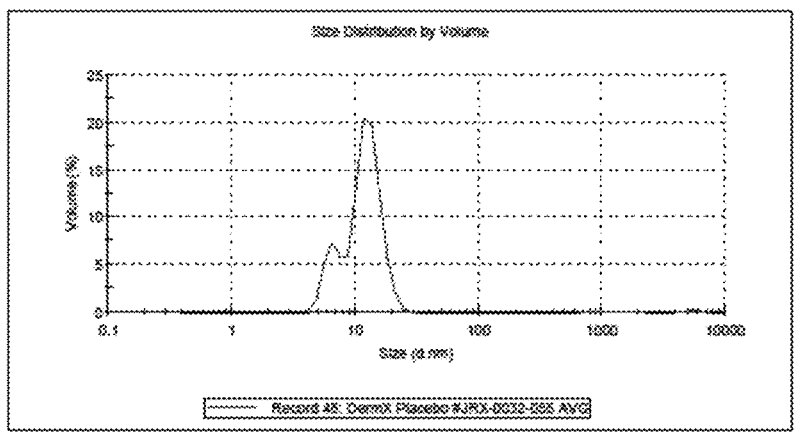

FIGURE 3E: Comparison of Raman Spectra.
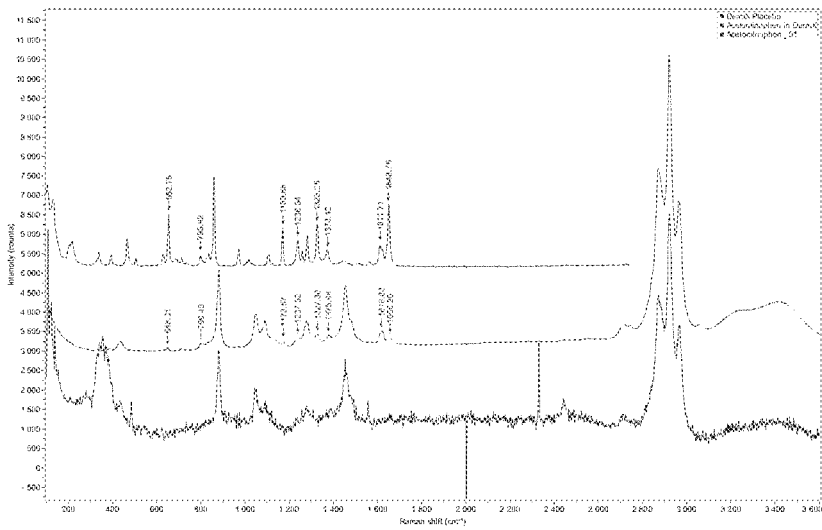
FIGURE 4A: Optical Image of Ibuprofen dry powder (400X magnification).

FIGURE 4B: Particle Size Distribution of Ibuprofen suspension.
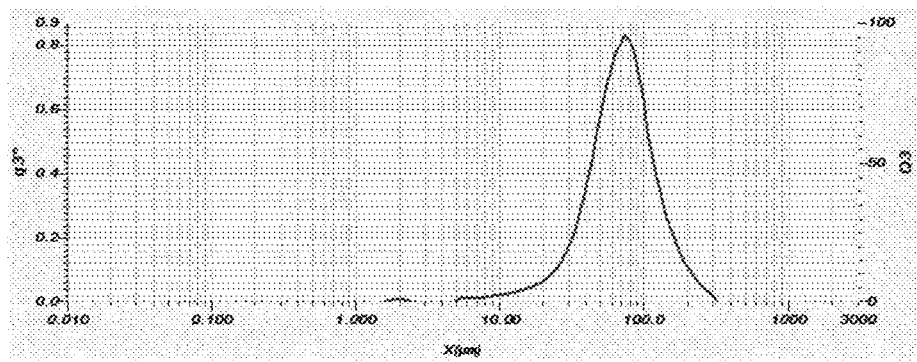
FIGURE 4C: Particle Size Distribution of "Liquid Ibuprofen".
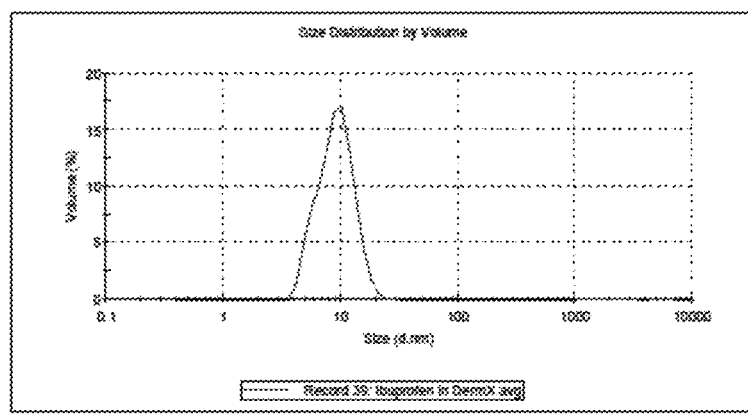

FIGURE 4D: Comparison of Raman Spectra.
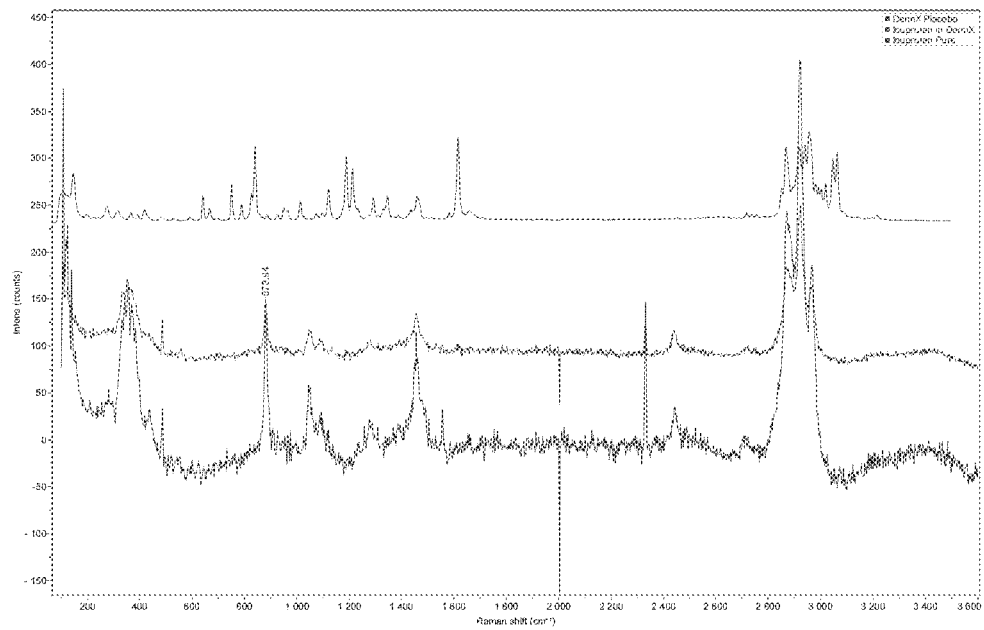
FIGURE 5A: Particle Size Distribution of Insulin solution.
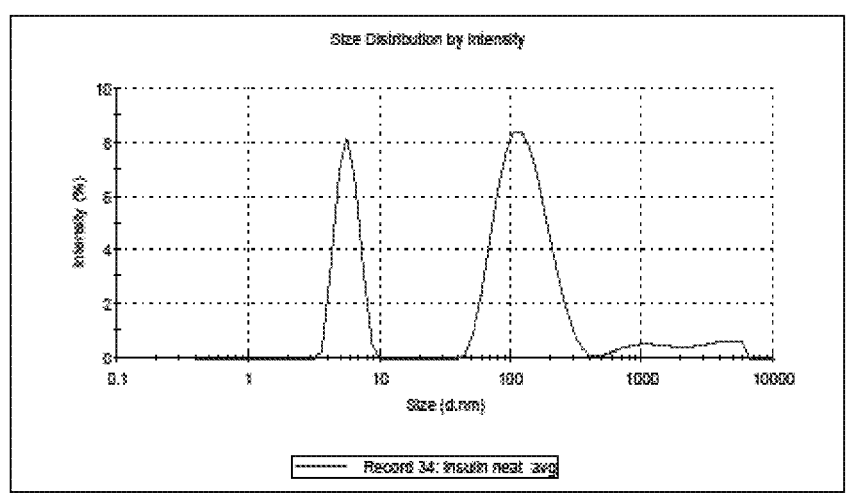

FIGURE 5B: Particle Size Distribution of Insulin suspension.
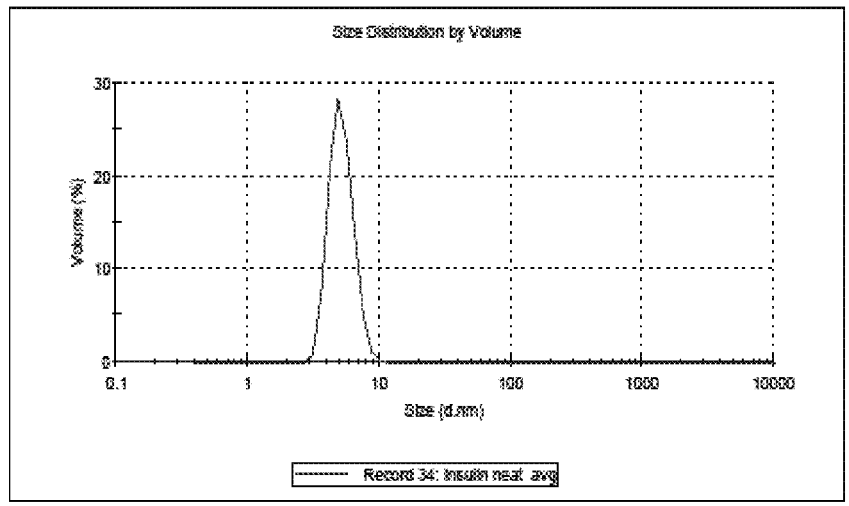
FIGURE 5C: Particle Size Distribution of "Liquid Ibuprofen".
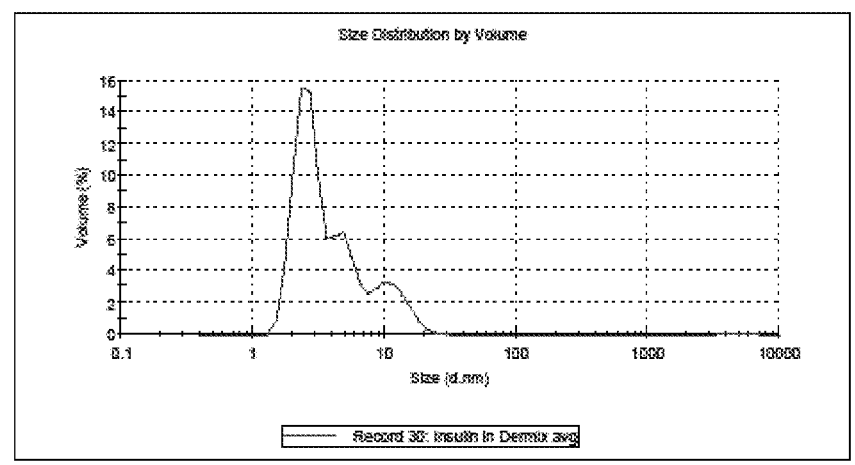

FIGURE 6A: Optical Image of Ketoprofen dry powder (400X magnification).
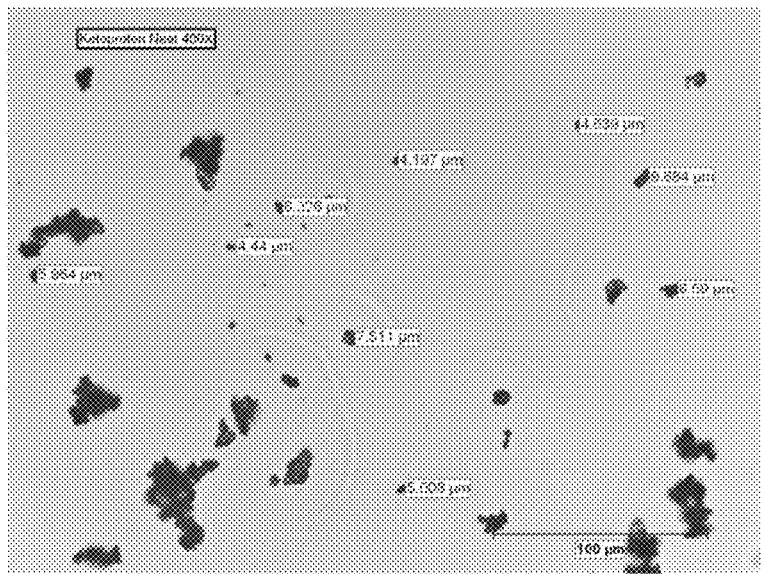
FIGURE 6B: Particle Size Distribution of Ketoprofen suspension.
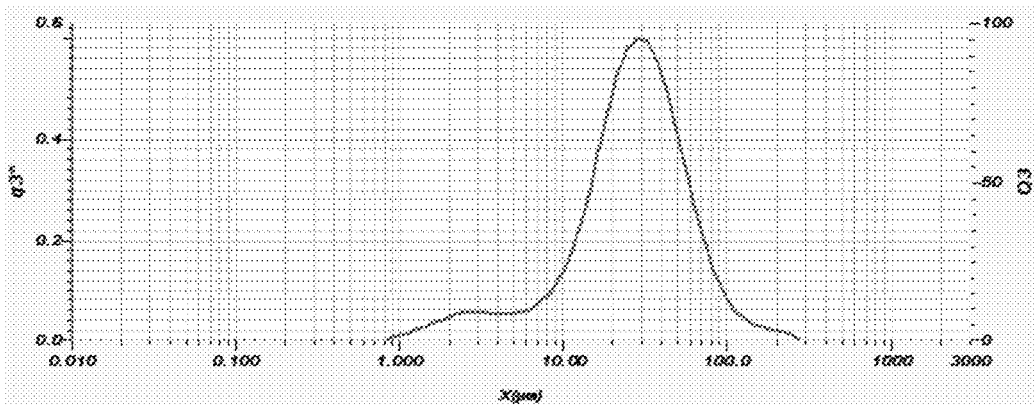

FIGURE 6C: Particle Size Distribution of "Liquid Ketoprofen".
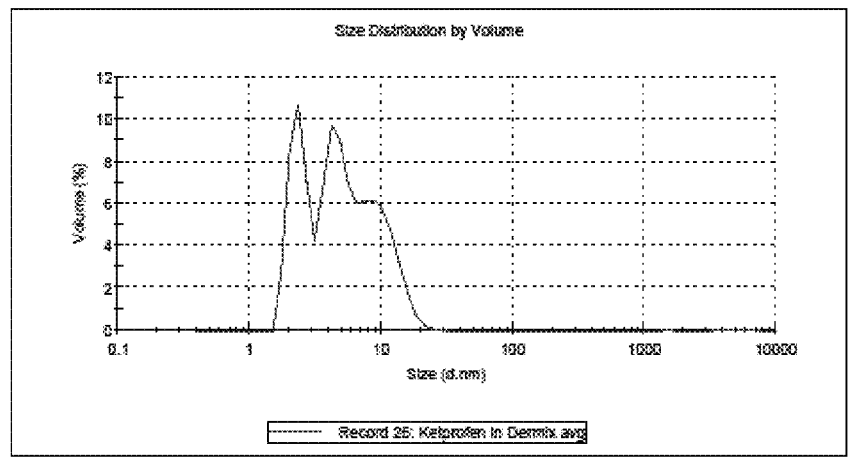
FIGURE 6D: Comparison of Raman Spectra.
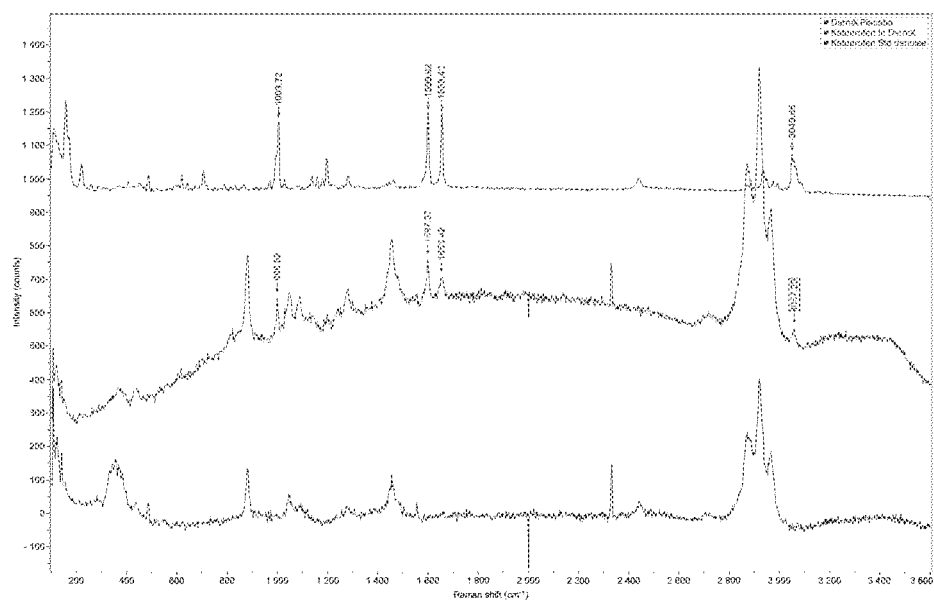

FIGURE 7A: Optical Image of Naproxen dry powder (400X magnification).
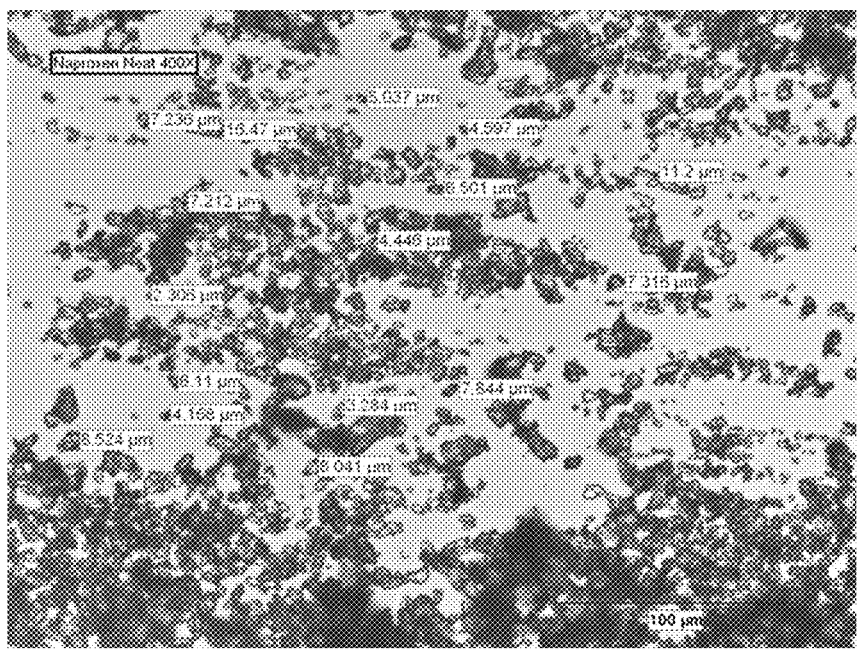
FIGURE 7B: Particle Size Distribution of Naproxen suspension.
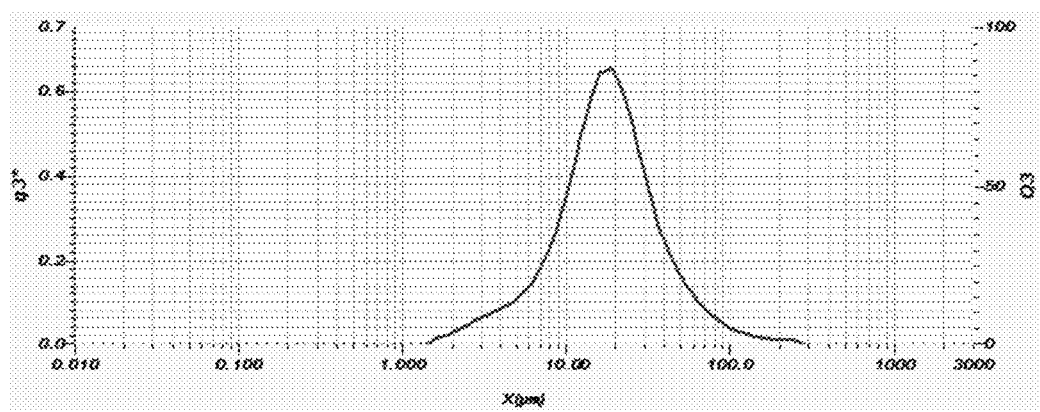

FIGURE 7C: Particle Size Distribution of "Liquid Naproxen".
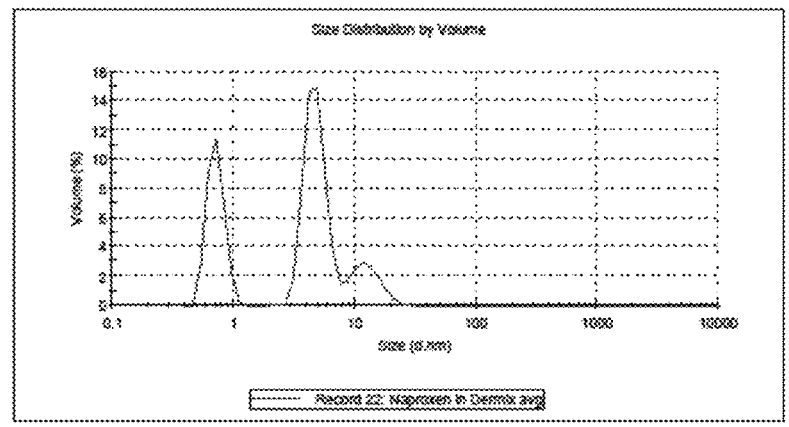
FIGURE 7D: Comparison of Raman Spectra.
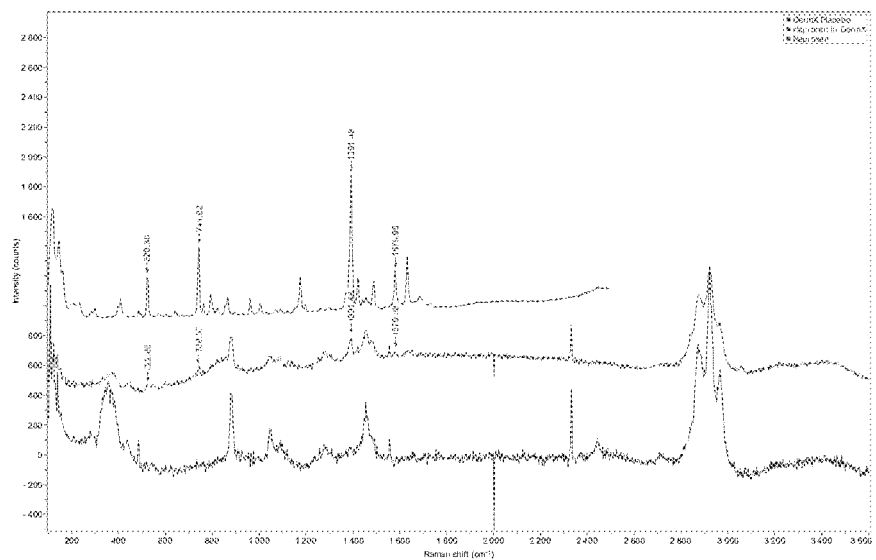

FIGURE 8A: Dry Aspirin at 100X Magnification.
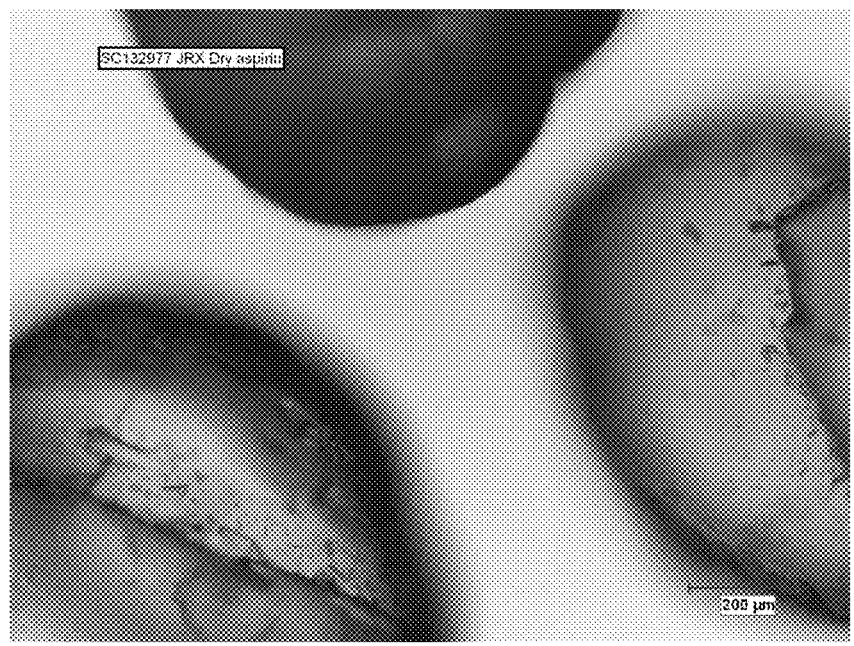
FIGURE 8B: Formula 1 at 100X Magnification.

FIGURE 8C: Formula 1C at 100X Magnification.
FIGURE 8D: Formula 2 at 100X Magnification.
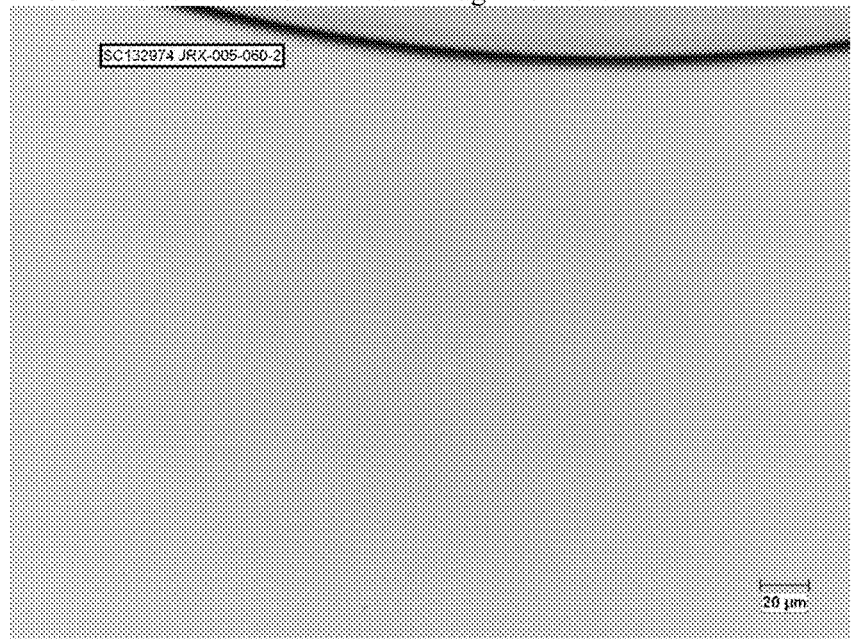

FIGURE 8E: Formula 3 at 100X Magnification.
FIGURE 8F: Dry Aspirin suspension at 400X Magnification.
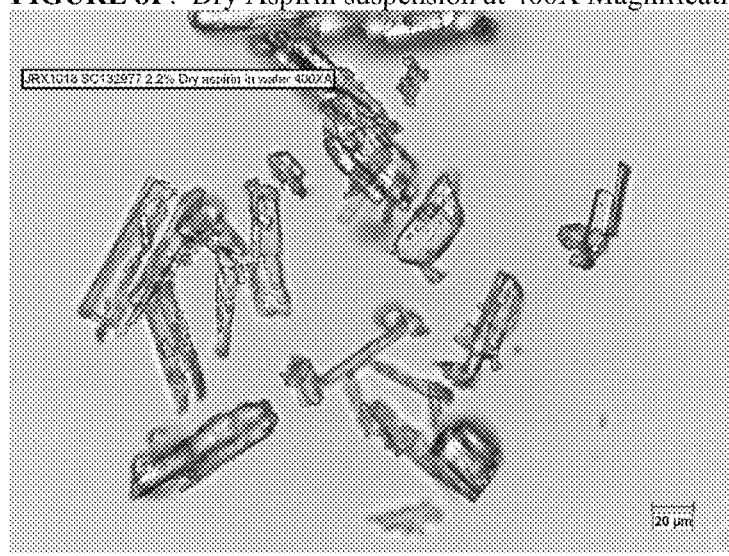

FIGURE 8G: Laser Diffraction Result for Dry Aspirin at 2.2% in Water.
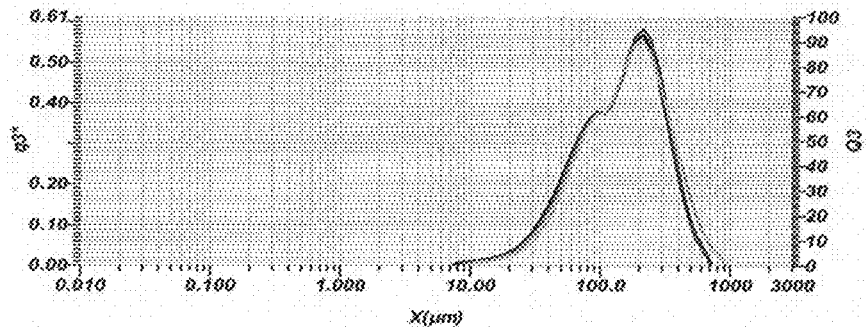

LIQUID TOPICAL PHARMACEUTICAL NANO-EMULSION FORMULATIONS

RELATED APPLICATIONS

The present application is a divisional of U.S. National Phase Ser. No. 14/655,238, filed on Jun. 24, 2015, under 35 U.S.C. § 371 of International Application No. PCT/US2013/077985, filed on Dec. 27, 2013, designating the United States of America and published in English language, which claims the benefits of priority to U.S. Provisional Application Ser. No. 61/748,036; filed Dec. 31, 2012; and U.S. Provisional Application Ser. No. 61/758,726; filed Jan. 30, 2013. The disclosures of the above-referenced applications are hereby expressly incorporated by reference in their entireties.

FIELD OF THE INVENTION

Aspects of the present invention are directed to preparations that are useful for delivery of an active ingredient. Some embodiments of these preparations include transdermal and/or dermal compositions, which are formulated with an active ingredient, including, for example, a non-steroidal anti-inflammatory drug (NSAID), such as aspirin, ibuprofen, ketoprofen, or naproxen, acetaminophen, or a polypeptide or protein, such as insulin, wherein the active ingredient is stabilized and greater than 90% of the particles of the active ingredient have a particle size that is less than or equal to 100 nanometers, such as 4 to 20 nanometers, as determined by Dynamic Light Scattering (DLS).

BACKGROUND OF THE INVENTION

It is common practice today for people to use a non-steroidal anti-inflammatory drug (hereinafter, an "NSAID") or acetaminophen to alleviate pain and/or reduce inflammation. NSAIDs are also commonly prescribed medications for treating medical conditions including acute pain, chronic pain, arthritis and fever. Today, people are very familiar with over-the-counter, nonprescription NSAIDs, such as aspirin and ibuprofen, as well as, acetaminophen. Many people today also suffer from diabetes and rely on insulin therapy to combat this disease.

NSAIDs are a class of drugs that provide analgesic, anti-inflammatory and antipyretic effects. While NSAIDs have similar anti-inflammatory properties to steroids, they are unique in that they are non-narcotic and lack many of the substantial side-effects of systemic steroid use. Typical NSAIDs include, but are not limited to, salicylic acid, aspirin, ibuprofen, naproxen, ketoprofen, indomethacin, etodolac, diclofenac sodium, diclofenac epolamine, ketorolac, meloxicam, piroxicam and nabumetone, all of which are available in most countries. Acetaminophen is a pain reliever and fever reducer but is not recognized for its anti-inflammatory properties and, thus, is not considered to be an NSAID.

A typical and very popular NSAID is acetylsalicylic acid, i.e., aspirin, a well-known anti-inflammatory. Since 1915, aspirin has been used effectively in the medical and scientific communities to treat pain. Despite its effectiveness, aspirin and other NSAIDs are not without shortcomings. NSAIDs taken orally may cause an increased risk of serious cardiovascular thrombotic events, myocardial infarction, and stroke, which can be fatal. This risk may increase with duration of systemic use. Patients with cardiovascular disease or risk factors for cardiovascular disease may be at a greater risk. Taking oral NSAIDs, including aspirin, can also increase the risk of serious gastrointestinal adverse events including bleeding, ulceration, and perforation of the stomach or intestines, which can be fatal. These events can occur at any time during use and without warning symptoms. Elderly patients are at greater risk for serious gastrointestinal events.

In view of these issues, topical NSAID and/or acetaminophen therapy is desired, especially if the clinical benefits of oral NSAID and/or acetaminophen therapy can be achieved without the side effects commonly associated with systemic NSAID and/or acetaminophen therapy, e.g. from ingesting oral tablets. However, there are many obstacles to achieving a useful topical formulation containing an NSAID and/or acetaminophen, including safety, stability of the active ingredient over time, and efficacy.

An important aspect of any NSAID and/or acetaminophen based topical pain reliever is the ability to permeate the necessary layers of the integument (skin) in order to relieve pain. Accordingly, an effective topical NSAID and/or acetaminophen formulation should be in the form of a liquid that suspends or dissolves the active ingredient, and facilitates transport across the integument to provide effective relief. Topical pain reliever formulations in the form of a liquid have been introduced in the past, but such topical pain relievers have traditionally lacked the ability to maintain the active ingredient in a suspension within the liquid of the topical pain reliever formulation.

Further, topical pain reliever formulations may have significant lag time between application to the skin and reducing pain/inflammation. There may be several reasons for this lag time. For example, the topical pain reliever formulations may not quickly or effectively permeate the skin. As a consequence, it may take longer, if at all, for a user to experience any pain relief due to slow penetration of active ingredient of penetration of only an insignificant dose of active ingredient.

Additionally, current NSAID and/or acetaminophen-containing topical pain reliever formulations have not adequately stabilized the active ingredient in liquid. That is, current NSAID and/or acetaminophen-containing topical pain formulations generally have a short shelf life since the active ingredient degrades, for example, by hydrolysis, glycolysis and/or transesterification. The industry has sought to minimize the effects of the above problems and to maintain a stable topical NSAID, e.g., see U.S. Pat. Nos. 5,318,960; 6,416,722; and 6,759,056, the disclosures of which are hereby expressly incorporated by reference in their entireties.

Similarly, investigators have long sought to stabilize and dermally and/or transdermally deliver therapeutically effective amounts of proteins, including insulin, e.g., see U.S. Pat. App. Pub. No. 2006/0046962, the disclosure of which is hereby expressly incorporated by reference in its entirety. Although a variety of approaches have been attempted in the past, the need for formulations that stabilize active ingredients, such as NSAIDs, acetaminophen, and proteins such as, insulin, so as to transdermally and/or dermally deliver therapeutically effective amounts of these active ingredients is manifest.

SUMMARY OF THE INVENTION

Aspects of the present invention concern the discovery of compositions and methods that reduce the particle size of active ingredients, including non-steroidal anti-inflammatory drugs (NSAID)s, acetaminophen, and/or polypeptides or proteins such as, insulin and thereby stabilize these active ingredients in an emulsion (a nano-emulsion), which, in turn, improves the delivery of the active ingredients and/or extends the shelf-life of these products. For example, when the transdermal and/or dermal formulations are prepared as described herein, it was found that the particle size of the active ingredient (e.g., NSAIDS, such as aspirin, ibuprofen, ketoprofen, and naproxen, and acetaminophen, as well as polypeptides or proteins such as, insulin) was reduced (e.g., after formulation as described herein, greater than 90% of the particles have a particle size of less than or equal to 100 nanometers, such as 4-20 nanometers, as determined by Dynamic Light Scattering (DLS), preferably using a volume-weighted particle size distribution calculation method). Accordingly, when the transdermal and/or dermal formulations are prepared, as described herein, it is contemplated that greater than or equal to or any number in between 90%, 91%, 92%, 93%, 94%, 95%, 96%, 97%, 98%, or 99% of the particles of the active ingredient in the transdermal and/or dermal liquid, e.g., NSAIDS such as, aspirin, ibuprofen, ketoprofen, naproxen, and/or acetaminophen, and/or polypeptides or proteins such as, insulin, are reduced to an average particle size of less than or equal to any number in between 100, 90, 80, 70, 60, 50, 40, 30, 20, 19, 18, 17, 16, 15, 14, 13, 12, 11, 10, 9, 8, 7, 6, 5, 4, or 3 nanometers, as determined by DLS, preferably using a volume-weighted particle size distribution calculation method.

The reduced particle size of the active ingredient is contemplated to increase the stability of the active ingredient within the composition (e.g., a transdermal and/or dermal preparation). It is contemplated that formulations prepared by an alternative method, wherein water is allowed to contact the active ingredient prior to mixing the active ingredient with an alcohol or ethoxylated oil or both will have considerably larger particle size of active ingredient, with greater heterogeneity in size of particles and the active ingredient in these formulations will be less stable and will have a shorter shelf-life than formulations prepared in accordance with the teachings provided herein.

It is contemplated that the reduced particle size and the increased stability of the active ingredient in the transdermal and/or dermal formulations described herein are the result of the particular amounts of the components in the formulations (e.g., the amount of ethoxylated oil, such as ethoxylated macadamia nut oil, ethoxylated meadow foam oil, or ethoxylated emu oil or mixtures thereof, having 10, 11, 12, 13, 14, 15, 16, 17, 18, 19, 20, 21, or 22 ethoxylations per molecule relative to the amount of water, alcohol (e.g., 100% ethanol), and any additional ingredients, such as fragrance), as well as, the order of the addition of the active ingredient(s) to the components of the liquid (e.g., the alcohol, ethoxylated oil, and water) during the mixing phase. For example, a process for making the transdermal and/or dermal compositions (e.g., liquids) described herein can be practiced by mixing an alcohol (e.g., 200 proof ethyl alcohol) and/or an ethoxylated oil (e.g., macadamia nut oil that has been ethoxylated to 10, 11, 12, 13, 14, 15, 16, 17, 18, 19, 20, 21, or 22 ethoxylations per molecule) with an active ingredient (e.g., an NSAID, such as aspirin, acetaminophen, or a protein such as, insulin) and subsequently adding water. By this approach, in particular adding the water after the active ingredient has mixed with the alcohol and/or ethoxylated oil, it is thought that the active ingredient reduces its particle size and the active ingredient is protected from destabilizing forces, such as hydrolysis mediated by the water in the formulation. In addition to increasing the stability of the active ingredient, it is contemplated that the reduced particle size of the active ingredient achieved by the methodologies described herein also allows for the active ingredient to remain in a liquid form for extended periods of time, which will facilitate and/or improve transdermal and/or dermal delivery of the active ingredient.

Nanoemulsion delivery system technology has been reviewed in the past, see e.g., "Edible nanoemulsions: fabrication, properties, and functional performance" (review) by David Julian McClements, Soft Matter, (2011) 7: 2297-2316. Nanoemulsions are typically characterized by extremely low interfacial tension. Accordingly, the system not only forms with minimal shear, but also spreads very easily after application to the surface of the skin or tissue (e.g., when applied topically or when introduced internally by injection or oral consumption). In the context of a transdermal and/or dermal composition, this property allows the formulation to immediately spread across the surface of the skin, penetrating all of the macroscopic openings in the dermis (e.g., pores and hair follicles) well in advance of the transfer of an active ingredient. The low interfacial tension can also be exploited in conjunction with micro-abrasion and injection or oral administration methodologies.

As used herein, the terms "formulation," "preparation," or "composition," can depending on the context, be used interchangeably. Some formulations described herein additionally may comprise one or more viscosity-increasing agents. Preferred viscosity-increasing agents include but are not limited to a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose. That is, some embodiments include a viscosity-increasing agent such as a cellulose derivative selected from the group consisting of hydroxyethylcellulose, methylcellulose, hydroxypropyl cellulose, carboxymethyl cellulose, hydroxypropyl methyl cellulose (E464), and hydroxyethyl methyl cellulose.

Accordingly, the preparations described herein (e.g., a transdermal and/or dermal composition) may be a liquid, a colloid, a hydrogel, a lotion, a cream, a rinse, a serum, a paste, or a puddy.

Aspects of the invention described herein concern a composition (e.g., a liquid) for drug and/or dietary supplement delivery, wherein said composition may be applied topically (e.g., to the skin, scalp, nasal membranes, oral, vaginal, or anal mucosa) or internally (e.g., by injection or ingestion) and, wherein said composition is comprised of a nano-emulsion comprising an active ingredient, including an NSAID (e.g., aspirin, ibuprofen, ketoprofen, or naproxen), acetaminophen, or a protein, such as insulin, collagen, or elastin, an alcohol (e.g., greater than or equal to any number in between 30%, 35%, 40%, 45%, 50%, 55%, 60%, 65%, or 70% alcohol, such as 200 proof ethyl alcohol, by total weight or volume), an ethoxylated oil (e.g., greater than or equal to or any number in between 2%, 4%, 8%, 10%, 12%, 15%, 20%, or 25% of an ethoxylated oil having 10, 11, 12, 13, 14, 15, 16, 17, 18, 19, 20, 21, or 22 ethoxylations per molecule, such as ethoxylated macadamia nut oil having 16 ethoxylations per molecule, by weight or volume), and water, wherein, on average, greater than or equal to or any number in between 90%, 92%, 94%, 96%, 98%, or 99% of the particles of the active ingredient have a particle size that is less than or equal to any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering (DLS), in some embodiments preferably using a volume-weighted particle size distribution calculation method.

Distinctively, the methodologies for formulation of the transdermal and/or dermal preparations provided herein involve adding or solubilizing the delivered material or active ingredient, such as an NSAID (e.g., aspirin, ibuprofen, ketoprofen, or naproxen), acetaminophen, or a protein (e.g., insulin, collagen, or elastin) to an alcohol and/or an ethoxylated oil. The active ingredient is believed to be incorporated into the lamellar (film) phase of the nano-emulsion along with the alcohol and/or the ethoxylated oil, which is created when the addition of the active ingredient is made to the alcohol and/or the ethoxylated oil prior to contacting water.

Since the active ingredient is confined to a region of the nano-emulsion, which does not favor hydrolysis or allow for contact with enzymes, proteases, hydrolases, and other degradative components of the body, e.g. the digestive track, the active ingredient is protected, stabilized, and the shelf-life of the active ingredient is extended. Because the primary surfactants used in the formulations described herein are chosen such that the hydrophobic portion of the surfactants (e.g., ethoxylated macadamia nut oil) matches the lipid makeup of the cell membranes of the target organ, the lamellar phase of the nano-emulsion containing the active ingredient is readily incorporated into the target cell membrane.

Accordingly, some embodiments include a transdermal and/or dermal composition (e.g., a liquid) comprising an ethoxylated oil, an alcohol, water; and an active ingredient, wherein greater than 90% of the particles of the active ingredient have a particle size that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering, using a volume-weighted particle size distribution calculation method. In some embodiments, the active ingredient is an NSAID, acetaminophen, or a protein or polypeptide, such as insulin. In some of these embodiments, the ethoxylated oil in the transdermal liquid is present at 2%-25% by total weight or total volume of the transdermal liquid, such as 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%. In some of these embodiments, the ethoxylated oil is an ethoxylated macadamia nut oil having 10, 11, 12, 13, 14, 15, 16, 17, 18, 19, 20, 21, or 22 ethoxylations per molecule. In some of these embodiments, the alcohol in the transdermal liquid is present at 1%-70%, e.g. 30%-70%, such as 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70%, by total weight or total volume of the transdermal liquid.

Additional embodiments concern a method of making a transdermal and/or dermal composition (e.g., a liquid) comprising the following steps in order: (a) mixing an amount of an active ingredient with an alcohol, which is present at a final concentration of 1%-70%, e.g. 30%-70%, such as 30%, 35%, 40%, 45%, 50%, 55%, 60%, 65%, or 70%, by total weight or total volume of the transdermal and/or dermal composition (e.g., liquid); (b) then adding an ethoxylated oil, which is present at a final concentration of 2%-25%, such as 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%, by total weight or total volume of the transdermal and/or dermal composition (e.g., liquid), to the mixture of (a); and (c) then adding an amount of water to bring the transdermal composition (e.g., liquid) to its final volume. In some embodiments, these methods further comprise evaluating the homogeneity of particle size of the active ingredient in the resultant transdermal and/or dermal composition (e.g., liquid). Some of these methods further comprise evaluating the particle size of the active ingredient in the resultant transdermal composition (e.g., liquid). Some of these methods further comprise evaluating the stability, solubility, or bioavailability of the active ingredient in the transdermal and/or dermal composition (e.g., liquid). Some of these methods further comprise filtering the transdermal composition (e.g., liquid) to isolate a fraction that comprises greater than 90% of the particles of the active ingredient with a particle size that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering, using a volume-weighted particle size distribution calculation method. In some of these methods, the active ingredient is an NSAID, acetaminophen, or a protein, such as, insulin.

Additional embodiments concern methods of reducing the particle size of an active ingredient comprising the following steps in order: (a) mixing an amount of an active ingredient with an alcohol, which is present at a final concentration of 1%-70%, e.g. 30%-70%, such as 30%, 35%, 40%, 45%, 50%, 55%, 60%, 65%, or 70%, by total weight or total volume of the transdermal composition (e.g., liquid); (b) adding an ethoxylated oil, which is present at a final concentration of 2%-25%, such as 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%, by total weight or total volume of the transdermal composition (e.g., liquid), to the mixture of (a); (c) adding an amount of water to bring the transdermal composition (e.g., liquid) to its final volume; and (d) analyzing the particle size of the active ingredient after steps (a) through (c).

Additional embodiments concern methods of stabilizing an active ingredient in a composition (e.g., liquid) comprising the following steps in order: (a) mixing an amount of an active ingredient with an alcohol, which is present at a final concentration of 1%-70%, e.g. 30%-70%, such as 30%, 35%, 40%, 45%, 50%, 55%, 60%, 65%, or 70%, by total weight or total volume of the transdermal composition (e.g., liquid); (b) adding an ethoxylated oil, which is present at a final concentration of 2%-25%, such as 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%, by total weight or total volume of the transdermal composition (e.g., liquid), to the mixture of (a); (c) adding an amount of water to bring the transdermal composition (e.g., liquid) to its final volume; and (d) analyzing the stability of the active ingredient after steps (a) through (c).

Additional embodiments concern methods of improving the solubility of an active ingredient in a composition (e.g., liquid) comprising the following steps in order: (a) mixing an amount of an active ingredient with an alcohol, which is present at a final concentration of 1%-70%, e.g. 30%-70%, such as 30%, 35%, 40%, 45%, 50%, 55%, 60%, 65%, or 70%, by total weight or total volume of the transdermal composition (e.g., liquid); (b) adding an ethoxylated oil, which is present at a final concentration of 2%-25%, such as 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%, by total weight or total volume of the transdermal composition (e.g., liquid), to the mixture of (a);

(c) adding an amount of water to bring the transdermal composition (e.g., liquid) to its final volume; and (d) analyzing the solubility of the active ingredient after steps (a) through (c).

Additional embodiments concern methods of improving the bioavailability of an active ingredient in a composition (e.g., liquid) comprising the following steps in order: (a) mixing an amount of an active ingredient with an alcohol, which is present at a final concentration of 1%-70%, e.g. 30%-70%, such as such as 30%, 35%, 40%, 45%, 50%, 55%, 60%, 65%, or 70%, by total weight or total volume of the transdermal composition (e.g., liquid); (b) adding an ethoxylated oil, which is present at a final concentration of 2%-25%, such as 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%, by total weight or total volume of the transdermal composition (e.g., liquid), to the mixture of (a); (c) adding an amount of water to bring the transdermal composition (e.g., liquid) to its final volume; and (d) analyzing the bioavailability of the active ingredient after steps (a) through (c).

Additional embodiments concern methods of reducing pain, fever, and/or inflammation or increasing the amount of insulin in a subject comprising administering to said subject one or more of the transdermal compositions (e.g., liquids) described above. Some of these methods further comprise evaluating a reduction of pain, fever, and/or inflammation or glucose intolerance in said subject.

Additional embodiments include a transdermal or dermal composition comprising an ethoxylated oil, e.g., PEG-16 macadamia glycerides; an alcohol, and an active ingredient, wherein the active ingredient has a particle size that is less than or equal to 100 nanometers (e.g., wherein, on average, greater than or equal to or any number in between 90%, 92%, 94%, 96%, 98%, or 99% of the particles of the active ingredient have a particle size that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering (DLS), using a volume-weighted particle size distribution calculation method). Optionally, these embodiments can include water and/or a viscosity increasing agent such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose.

These embodiments can be made by mixing in the following order: mixing an amount of an active ingredient with an alcohol and adding an amount of ethoxylated oil, such as PEG-16 macadamia glycerides to the alcohol/active ingredient mixture. Optionally, water and/or a viscosity-increasing agent can be added after the addition of the ethoxylated oil.

Aspects of the present invention may be elucidated by considering the embodiments listed below:

1. A transdermal and/or dermal composition (e.g., a liquid) comprising:
   (a) an ethoxylated oil,
   (b) an alcohol,
   (c) an active ingredient, wherein greater than 90% of the particles of the active ingredient have a particle size that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, or smaller, as determined by Dynamic Light Scattering, using a volume-weighted particle size distribution calculation method; and
   (d) optionally, water.

2. The transdermal and/or dermal composition of embodiment 1, further comprising one or more viscosity-increasing agents such as, a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose.

3. The transdermal and/or dermal composition of embodiment 1 or 2, wherein the active ingredient is an Non-Steroidal Anti-Inflammatory Drug (or NSAID), such as aspirin (acetylsalicylic acid), naproxen (2-(6-methoxynaphthalen-2-yl)propanoic acid), diclofenac (2-(2,6-dichloranilino) phenylacetic acid) (sodium and/or epolamine), ibuprofen (iso-butyl-propanoic-phenolic acid), or ketoprofen ((RS)2-(3-benzoylphenyl)-propionic acid); acetaminophen (N-acetyl-para-aminophenol); a protein such as, collagen, elastin, or insulin, or an antibiotic, such as a doxycycline (4S,4aR,5S,5aR,6R,12aS)-4-(Dimethylamino)-3,5,10,12, 12a-pentahydroxy-6-methyl-1,11-dioxo-1,4,4a,5,5a,6,11, 12a-octahydro-2-tetracenecarboxamide) or tetracycline ((4S,6S,12aS)-4-(dimethylamino)-1,4,4a,5,5a,6,11,12a-octahydro-3,6,10,12,12a-pentahydroxy-6-methyl-1,11-dioxonaphthacene-2-carboxamide).

4. The transdermal and/or dermal composition of any one of embodiments 1-3, wherein said ethoxylated oil in the transdermal and/or dermal liquid is present at 2%-25% by total weight or total volume of the transdermal and/or dermal composition.

5. The transdermal and/or dermal composition of any one of embodiments 1-4, wherein said ethoxylated oil is an ethoxylated macadamia nut oil having 10, 11, 12, 13, 14, 15, 16, 17, 18, 19, 20, 21, 22, 23 or 24 ethoxylations per molecule.

6. The transdermal and/or dermal composition of any one of embodiments 1-5, wherein said alcohol in the transdermal and/or dermal liquid is present at 1%-70% by total weight or total volume of the transdermal and/or dermal composition, such as %, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70%.

7. The transdermal and/or dermal composition of any one of embodiments 1-6, further comprising a fragrance.

8. A method of making a transdermal and/or dermal composition (e.g., liquid) comprising the following steps in order:
   (a) mixing an amount of an active ingredient with an alcohol; and
   (b) adding an ethoxylated oil, which is present at a final concentration of 2%-25% by total weight or total volume of the transdermal and/or dermal composition, to the mixture of (a); and
   (c) optionally, adding an amount of water to bring the transdermal and/or dermal composition to its final volume, to the mixture of (a) and (b).

9. The method of embodiment 8, further comprising adding one or more viscosity-increasing agents.

10. The method of embodiment 9, wherein said one or more viscosity-increasing agents comprises a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose.

11. The method of any one of embodiments 8-10, further comprising adding a fragrance.

12. The method of any one of embodiments 8-11, further comprising evaluating the homogeneity of particle size of the active ingredient in the resultant transdermal and/or dermal composition.

13. The method of any one of embodiments 8-12, further comprising evaluating the particle size of the active ingredient in the resultant transdermal and/or dermal composition.

14. The method of any one of embodiments 8-13, further comprising evaluating the chemical stability, physical stability, bioavailability, and/or solubility of the active ingredient in the transdermal and/or dermal composition.

15. The method of any one of embodiments 8-14, further comprising filtering the transdermal and/or dermal composition to isolate a fraction that comprises greater than 90% of the particles of the active ingredient with a particle size that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, or smaller, as determined by Dynamic Light Scattering, using a volume-weighted particle size distribution calculation method.

16. The method of any one of embodiments 8-15, wherein the active ingredient is a Non-Steroidal Anti-Inflammatory Drug, such as aspirin (acetylsalicylic acid), naproxen (2-(6-methoxynaphthalen-2-yl)propanoic acid), diclofenac (2-(2, 6-dichloranilino) phenylacetic acid) (sodium and/or epolamine), ibuprofen (iso-butyl-propanoic-phenolic acid), or ketoprofen ((RS)2-(3-benzoylphenyl)-propionic acid); acetaminophen (N-acetyl-para-aminophenol); a protein such as, collagen, elastin, or insulin, or an antibiotic, such as a doxycycline (4S,4aR,5S,5aR,6R,12aS)-4-(Dimethylamino)-3,5,10,12,12a-pentahydroxy-6-methyl-1,11-dioxo-1,4,4a,5, 5a,6,11,12a-octahydro-2-tetracenecarboxamide) or tetracycline ((4S,6S,12aS)-4-(dimethylamino)-1,4,4a,5,5a,6,11, 12a-octahydro-3,6,10,12,12a-pentahydroxy-6-methyl-1,11-dioxonaphthacene-2-carboxamide).

17. A method of reducing the particle size of an active ingredient comprising the following steps in order:
(a) mixing an amount of an active ingredient with an alcohol;
(b) adding an ethoxylated oil, which is present at a final concentration of 2%-25% by total weight or total volume, to the mixture of (a);
(c) optionally, adding an amount of water to bring the composition to its final volume, to the mixture (a) and (b); and
(d) analyzing the particle size of the active ingredient after steps (a) through (c).

18. The method of embodiment 17, wherein said active ingredient comprises a drug.

19. The method of embodiment 17, wherein said active ingredient comprises a dietary supplement.

20. The method of embodiment 19, wherein said dietary supplement comprises a vitamin or a mixture of vitamins or an amino acid or mixtures of amino acids.

21. The method of embodiment 17, wherein said active ingredient comprises an antioxidant.

22. The method of embodiment 21, wherein said antioxidant is selected from the list comprising alpha-lipoic acid, vitamin C, resveratrol, Epigallocatechin gallate (EGCG), green tea extract, N-acetyl cysteine, glutathione, a tocopherol, a tocotrienol, or mixture thereof.

23. The method of embodiment 17, wherein said active ingredient comprises an amino acid.

24. The method of embodiment 23, wherein said amino acid is selected from the list comprising glutamine or arginine, or an arginine derivative.

25. The method of embodiment 17, wherein said active ingredient comprises a sugar or a sugar-containing compound such as a cyclodextrin or beta-cyclodextrin.

26. The method of embodiment 17, wherein said active ingredient comprises a hormone precursor or hormone mimic.

27. The method of embodiment 26, wherein said hormone precursor or hormone mimic is dehydroepiandrosterone (DHEA).

28. The method of embodiment 26, wherein said hormone precursor or hormone mimic is human growth hormone (hGH).

29. The method of embodiment 26, wherein said hormone precursor or hormone mimic is erythropoietin (EPO).

30. A method of stabilizing an active ingredient in a composition (e.g., a liquid) comprising the following steps in order:
(a) mixing an amount of an active ingredient with an alcohol;
(b) adding an ethoxylated oil, which is present at a final concentration of 2%-25% by total weight or total volume, to the mixture of (a);
(c) optionally, adding an amount of water to bring the composition to its final volume, to the mixture of (a) and (b); and
(d) analyzing the chemical and/or physical stability of the active ingredient after steps (a) through (c).

31. The method of embodiment 30, wherein said active ingredient comprises a dietary supplement.

32. The method of embodiment 31, wherein said dietary supplement comprises a vitamin or a mixture of vitamins or an amino acid or mixtures of amino acids.

33. The method of embodiment 30, wherein said active ingredient comprises an antioxidant.

34. The method of embodiment 33, wherein said antioxidant is selected from the list comprising alpha-lipoic acid, vitamin C, resveratrol, Epigallocatechin gallate (EGCG), green tea extract, N-acetyl cysteine, glutathione, a tocopherol, a tocotrienol, or mixture thereof.

35. The method of embodiment 30, wherein said active ingredient comprises an amino acid.

36. The method of embodiment 35, wherein said amino acid is selected from the list comprising glutamine or arginine, or an arginine derivative.

37. The method of embodiment 30, wherein said active ingredient comprises a sugar or a sugar-containing compound such as a cyclodextrin or beta-cyclodextrin.

38. The method of embodiment 30, wherein said active ingredient comprises a hormone precursor or hormone mimic.

39. The method of embodiment 38, wherein said hormone precursor or hormone mimic is dehydroepiandrosterone (DHEA).

40. The method of embodiment 38, wherein said hormone precursor or hormone mimic is human growth hormone (hGH).

41. The method of embodiment 38, wherein said hormone precursor or hormone mimic is erythropoietin (EPO).

42. A method of improving solubility of an active ingredient in a composition (e.g, a liquid) comprising the following steps in order:
(a) mixing an amount of an active ingredient with an alcohol;

(b) adding an ethoxylated oil, which is present at a final concentration of 2%-25% by total weight or total volume, to the mixture of (a);

(c) optionally, adding an amount of water to bring the composition to its final volume, to the mixture of (a) and (b); and (d) analyzing the solubility of the active ingredient after steps (a) through (c).

43. The method of embodiment 42, wherein said active ingredient comprises a drug.

44. The method of embodiment 42, wherein said active ingredient comprises a dietary supplement.

45. The method of embodiment 44, wherein said dietary supplement comprises a vitamin or a mixture of vitamins or an amino acid or mixtures of amino acids.

46. The method of embodiment 42, wherein said active ingredient comprises an antioxidant.

47. The method of embodiment 46, wherein said antioxidant is selected from the list comprising alpha-lipoic acid, vitamin C, resveratrol, Epigallocatechin gallate (EGCG), green tea extract, N-acetyl cysteine, glutathione, a tocopherol, a tocotrienol, or mixture thereof.

48. The method of embodiment 42, wherein said active ingredient comprises an amino acid.

49. The method of embodiment 48, wherein said amino acid is selected from the list comprising glutamine or arginine, or an arginine derivative.

50. The method of embodiment 42, wherein said active ingredient comprises a sugar or a sugar-containing compound such as a cyclodextrin or beta-cyclodextrin.

51. The method of embodiment 42, wherein said active ingredient comprises a hormone precursor or hormone mimic.

52. The method of embodiment 51, wherein said hormone precursor or hormone mimic is dehydroepiandrosterone (DHEA).

53. The method of embodiment 51, wherein said hormone precursor or hormone mimic is human growth hormone (hGH).

54. The method of embodiment 51, wherein said hormone precursor or hormone mimic is erythropoietin (EPO).

55. A method of improving bioavailability of an active ingredient in a composition (e.g., a liquid) comprising the following steps in order:

(a) mixing an amount of an active ingredient with an alcohol;

(b) adding an ethoxylated oil, which is present at a final concentration of 2%-25% by total weight or total volume, to the mixture of (a);

(c) optionally, adding an amount of water to bring the composition to its final volume, to the mixture of (a) and (b); and (d) analyzing the bioavailability of the active ingredient after steps (a) through (c).

56. The method of embodiment 55, wherein said active ingredient comprises a drug.

57. The method of embodiment 55, wherein said active ingredient comprises a dietary supplement.

58. The method of embodiment 57, wherein said dietary supplement comprises a vitamin or a mixture of vitamins or an amino acid or mixtures of amino acids.

59. The method of embodiment 55, wherein said active ingredient comprises an antioxidant.

60. The method of embodiment 59, wherein said antioxidant is selected from the list comprising alpha-lipoic acid, vitamin C, resveratrol, Epigallocatechin gallate (EGCG), green tea extract, N-acetyl cysteine, glutathione, a tocopherol, a tocotrienol, or mixture thereof.

61. The method of embodiment 55, wherein said active ingredient comprises an amino acid.

62. The method of embodiment 61, wherein said amino acid is selected from the list comprising glutamine or arginine, or an arginine derivative.

63. The method of embodiment 55, wherein said active ingredient comprises a sugar or a sugar-containing compound such as a cyclodextrin or beta-cyclodextrin.

64. The method of embodiment 55, wherein said active ingredient comprises a hormone precursor or hormone mimic.

65. The method of embodiment 64, wherein said hormone precursor or hormone mimic is dehydroepiandrosterone (DHEA).

66. The method of embodiment 64, wherein said hormone precursor or hormone mimic is human growth hormone (hGH).

67. The method of embodiment 64, wherein said hormone precursor or hormone mimic is erythropoietin (EPO).

68. A method of reducing pain, fever, and/or inflammation or increasing the amount of insulin in a subject (e.g., human or animal) comprising:

administering to said subject the transdermal and/or dermal composition of embodiment 2.

69. The method of embodiment 68, further comprising evaluating a reduction of pain, fever, and/or inflammation or glucose intolerance in said subject.

70. The method of embodiment 68, wherein said active ingredient comprises a drug.

71. The method of embodiment 68, wherein said active ingredient comprises a dietary supplement.

72. The method of embodiment 71, wherein said dietary supplement comprises a vitamin or a mixture of vitamins or an amino acid or mixtures of amino acids.

73. The method of embodiment 68, wherein said active ingredient comprises an antioxidant.

74. The method of embodiment 73, wherein said antioxidant is selected from the list comprising alpha-lipoic acid, vitamin C, resveratrol, Epigallocatechin gallate (EGCG), green tea extract, N-acetyl cysteine, glutathione, a tocopherol, a tocotrienol, or mixture thereof.

75. The method of embodiment 68, wherein said active ingredient comprises an amino acid.

76. The method of embodiment 75, wherein said amino acid is selected from the list comprising glutamine or arginine, or an arginine derivative.

77. The method of embodiment 68, wherein said active ingredient comprises a sugar or a sugar-containing compound such as a cyclodextrin or beta-cyclodextrin.

78. The method of embodiment 68, wherein said active ingredient comprises a hormone precursor or hormone mimic.

79. The method of embodiment 78, wherein said hormone precursor or hormone mimic is dehydroepiandrosterone (DHEA).

80. The method of embodiment 78, wherein said hormone precursor or hormone mimic is human growth hormone (hGH).

81. The method of embodiment 78, wherein said hormone precursor or hormone mimic is erythropoietin (EPO).

82. A method of inhibiting a bacterial infection in a subject (e.g., human or animal) comprising:
   administering to said subject the transdermal and/or dermal composition of embodiment 2 and, optionally, determining the inhibition of bacteria in said subject after said administration.

83. The method of embodiment 82, wherein said active ingredient comprises a drug.

84. The method of embodiment 82, wherein said active ingredient comprises a dietary supplement.

85. The method of embodiment 84, wherein said dietary supplement comprises a vitamin or a mixture of vitamins or an amino acid or mixtures of amino acids.

86. The method of embodiment 82, wherein said active ingredient comprises an antioxidant.

87. The method of embodiment 86, wherein said antioxidant is selected from the list comprising alpha-lipoic acid, vitamin C, resveratrol, Epigallocatechin gallate (EGCG), green tea extract, N-acetyl cysteine, glutathione, a tocopherol, a tocotrienol, or mixture thereof.

88. The method of embodiment 82, wherein said active ingredient comprises an amino acid.

89. The method of embodiment 88, wherein said amino acid is selected from the list comprising glutamine or arginine, or an arginine derivative.

90. The method of embodiment 82, wherein said active ingredient comprises a sugar or a sugar-containing compound such as a cyclodextrin or beta-cyclodextrin.

91. The method of embodiment 82, wherein said active ingredient comprises a hormone precursor or hormone mimic.

92. The method of embodiment 91, wherein said hormone precursor or hormone mimic is dehydroepiandrosterone (DHEA).

93. The method of embodiment 91, wherein said hormone precursor or hormone mimic is human growth hormone (hGH).

94. The method of embodiment 91, wherein said hormone precursor or hormone mimic is erythropoietin (EPO).

95. A method of making a transdermal and/or dermal composition (e.g., a liquid) comprising the following steps in order:
   (a) mixing an amount of an active ingredient with an alcohol, which the minimum amount of such alcohol is used to solubilize such active ingredient, wherein such alcohol is present at a final concentration of 1%-75% by total weight or total volume of the transdermal and/or dermal composition;
   (b) adding an ethoxylated oil, which is present at a final concentration of 2%-25% by total weight or total volume of the transdermal and/or dermal composition, to the mixture of (a); and
   (c) optionally, adding an amount of water to the mixture of (a) and (b);
   wherein said transdermal and/or dermal composition comprises particles 90% of which are not greater than 100 nanometers on average as determined by dynamic light scattering.

96. The method of embodiment 95, further comprising, adding one or more viscosity-increasing agents.

97. The method of embodiment 96, wherein said one or more viscosity-increasing agents comprises a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose.

98. The method of embodiment 95, further comprising, adding one or more of a fragrance and a coloring agent, to the mixture of (a), (b) and (c).

99. The method of embodiment 95, wherein said alcohol is present at a final concentration of 1%-70%.

100. The method of embodiment 95, wherein said alcohol is present at a final concentration of 30%-70%.

101. The method of embodiment 95, wherein said alcohol is present at a final concentration of 40%-60%.

102. The method of embodiment 95, wherein said alcohol is present at a final concentration of 45%-55%.

103. The method of embodiment 95, wherein said alcohol is present at a final concentration of 46%-54%.

104. The method of embodiment 95, wherein said alcohol is present at a final concentration of 47%-53%.

105. The method of embodiment 95, wherein said alcohol is present at a final concentration of 48%-52%.

106. The method of embodiment 95, wherein said alcohol is present at a final concentration of 49%-51%.

107. The method of embodiment 95, wherein said alcohol is present at a final concentration of 50%.

108. The method of any of embodiments 95-107, wherein said ethoxylated oil is present at a final concentration of 2%-20%.

109. The method of any of embodiments 95-107, wherein said ethoxylated oil is present at a final concentration of 4%-20%.

110. The method of any of embodiments 95-107, wherein said ethoxylated oil is present at a final concentration of 4%-16%.

111. The method of any of embodiments 95-107, wherein said ethoxylated oil is present at a final concentration of 5%-15%.

112. The method of any of embodiments 95-107, wherein said ethoxylated oil is present at a final concentration of 6%-14%.

113. The method of any of embodiments 95-107, wherein said ethoxylated oil is present at a final concentration of 7%-13%.

114. The method of any of embodiments 95-107, wherein said ethoxylated oil is present at a final concentration of 8%-12%.

115. The method of any of embodiments 95-107, wherein said ethoxylated oil is present at a final concentration of 9%-11%.

116. The method of any of embodiments 95-107, wherein said ethoxylated oil is present at a final concentration of 10%.

117. The method of any of embodiments 95-116, wherein said ethoxylated oil comprises Pegylated (or PEG) material.

118. The method of embodiment 117, wherein said ethoxylated oil comprises a plant oil.

119. The method of embodiment 118, wherein said ethoxylated oil comprises a plant nut oil.

120. The method of embodiment 119, wherein said plant nut oil is a macadamia nut oil.

121. The method of any of embodiments 117-120, wherein said PEG comprises PEG-16.

122. The method of any of embodiments 117-121, wherein said PEG-16 comprises PEG-16 Macadamia Glycerides.

123. The method of any of embodiments 95-122, wherein said active ingredient comprises a non-steroidal anti-inflammatory drug (NSAID).

124. The method of embodiment 123, wherein said NSAID is at least one aspirin (acetylsalicylic acid), naproxen (2-(6-methoxynaphthalen-2-yl)propanoic acid), diclofenac (2-(2,6-dichloranilino) phenylacetic acid) (sodium and/or epolamine), ibuprofen (iso-butyl-propanoic-phenolic acid), or ketoprofen ((RS)2-(3-benzoylphenyl)-propionic acid); and/or acetaminophen (N-acetyl-para-aminophenol).

125. The method of embodiment 123, wherein said NSAID is aspirin.

126. The method of any of embodiments 95-122, wherein said active ingredient comprises one or more opioids, anti-depressants, anti-epileptic drugs, adjuvant medications, muscle relaxers, nerve abalation drugs, spinal chord stimulators, nutraceuticals, vitamins for improved nutrition, minerals, neuropathy therapy drugs, male hormonal balancing drugs, female hormonal balancing drugs, and bio-identical hormones.

127. The method of any of embodiments 95-122, wherein said active ingredient comprises a polypeptide.

128. The method of embodiment 127, wherein said polypeptide is insulin.

129. The method of any of embodiments 95-128, wherein said transdermal and/or dermal composition comprises particles 90% of which are no greater than 90 nanometers on average as assayed by dynamic light scattering.

130. The method of any of embodiments 95-128, wherein said transdermal and/or dermal composition comprises particles 90% of which are no greater than 80 nanometers on average as assayed by dynamic light scattering.

131. The method of any of embodiments 95-128, wherein said transdermal and/or dermal composition comprises particles 90% of which are no greater than 70 nanometers on average as assayed by dynamic light scattering.

132. The method of any of embodiments 95-128, wherein said transdermal and/or dermal composition comprises particles 90% of which are no greater than 60 nanometers on average as assayed by dynamic light scattering.

133. The method of any of embodiments 95-128, wherein said transdermal and/or dermal composition comprises particles 90% of which are no greater than 50 nanometers on average as assayed by dynamic light scattering.

134. The method of any of embodiments 95-128, wherein said transdermal and/or dermal composition comprises particles 90% of which are no greater than 40 nanometers on average as assayed by dynamic light scattering.

135. The method of any of embodiments 95-128, wherein said transdermal and/or dermal composition comprises particles 90% of which are no greater than 30 nanometers on average as assayed by dynamic light scattering.

136. The method of any of embodiments 95-128, wherein said transdermal and/or dermal composition comprises particles 90% of which are no greater than 25 nanometers on average as assayed by dynamic light scattering.

137. The method of any of embodiments 95-128, wherein said transdermal and/or dermal composition comprises particles 90% of which are no greater than 20 nanometers on average as assayed by dynamic light scattering.

138. The method of any of embodiments 95-128, wherein said transdermal and/or dermal composition comprises particles 90% of which are no greater than 19 nanometers on average as assayed by dynamic light scattering.

139. The method of any of embodiments 95-128, wherein said transdermal and/or dermal composition comprises particles 90% of which are no greater than 18 nanometers on average as assayed by dynamic light scattering.

140. The method of any of embodiments 95-128, wherein said transdermal and/or dermal composition comprises particles 90% of which are no greater than 17 nanometers on average as assayed by dynamic light scattering.

141. The method of any of embodiments 95-128, wherein said transdermal and/or dermal composition comprises particles 90% of which are no greater than 16 nanometers on average as assayed by dynamic light scattering.

142. The method of any of embodiments 95-128, wherein said transdermal and/or dermal composition comprises particles 90% of which are no less than 2 nanometers on average as assayed by dynamic light scattering.

143. The method of any of embodiments 95-128, wherein said transdermal and/or dermal composition comprises particles 90% of which are no less than 3 nanometers on average as assayed by dynamic light scattering.

144. The method of any of embodiments 95-128, wherein said transdermal and/or dermal composition comprises particles 90% of which are no less than 4 nanometers on average as assayed by dynamic light scattering.

145. A method of reducing the particle size of an active ingredient in a drug delivery composition comprising water, said method comprising the following steps in order:
  (a) mixing an amount of an active ingredient with an alcohol;
  (b) adding an ethoxylated oil, which is present at a final concentration of 2%-25% by total weight or total volume, to the mixture of (a);
  (c) optionally, adding an amount of water to bring the composition to its final volume, to the mixture (a) and (b); and
  (d) analyzing the particle size of the active ingredient after steps (a) through (c).

146. The method of embodiment 145, wherein said active ingredient comprises a drug.

147. The method of embodiment 145, wherein said active ingredient comprises a dietary supplement.

148. The method of embodiment 147, wherein said dietary supplement comprises a vitamin or a mixture of vitamins or an amino acid or mixtures of amino acids.

149. The method of embodiment 145, wherein said active ingredient comprises an antioxidant.

150. The method of embodiment 149, wherein said antioxidant is selected from the list comprising alpha-lipoic acid, vitamin C, resveratrol, Epigallocatechin gallate (EGCG), green tea extract, N-acetyl cysteine, glutathione, a tocopherol, a tocotrienol, or mixture thereof.

151. The method of embodiment 145, wherein said active ingredient comprises an amino acid.

152. The method of embodiment 151, wherein said amino acid is selected from the list comprising glutamine or arginine, or an arginine derivative.

153. The method of embodiment 145, wherein said active ingredient comprises a sugar or a sugar-containing compound such as a cyclodextrin or beta-cyclodextrin.

154. The method of embodiment 145, wherein said active ingredient comprises a hormone precursor or hormone mimic.

155. The method of embodiment 154, wherein said hormone precursor or hormone mimic is dehydroepiandrosterone (DHEA).

156. The method of embodiment 154, wherein said hormone precursor or hormone mimic is human growth hormone (hGH).

157. The method of embodiment 154, wherein said hormone precursor or hormone mimic is erythropoietin (EPO).

BRIEF DESCRIPTION OF THE DRAWINGS

FIG. 1A. Contact angle for Water using Quartz Plate as Substrate.

FIG. 1B. Contact angle for DermX® Direct "Liquid Aspirin" using Quartz Plate as Substrate.

FIG. 2A. Photomicrograph of Water Spreading using Quartz Plate as Substrate. Each grid division equals 2 mm.

FIG. 2B. Photomicrograph of DermX® Direct "Liquid Aspirin" Spreading using Quartz Plate as Substrate. Each grid division equals 2 mm.

FIG. 3A: Optical Image of Acetaminophen dry powder (400× magnification).

FIG. 3B: Particle Size Distribution of Acetaminophen suspension.

FIG. 3C: Particle Size Distribution of "Liquid Acetaminophen".

FIG. 3D: Particle Size Distribution of the DermX® Megaspheres™ carrier system ("Placebo").

FIG. 3E: Comparison of Raman Spectra.

FIG. 4A: Optical Image of Ibuprofen dry powder (400× magnification).

FIG. 4B: Particle Size Distribution of Ibuprofen suspension.

FIG. 4C: Particle Size Distribution of "Liquid Ibuprofen".

FIG. 4D: Comparison of Raman Spectra.

FIG. 5A: Particle Size Distribution of Insulin solution.

FIG. 5B: Particle Size Distribution of Insulin suspension.

FIG. 5C: Particle Size Distribution of "Liquid Ibuprofen".

FIG. 6A: Optical Image of Ketoprofen dry powder (400× magnification).

FIG. 6B: Particle Size Distribution of Ketoprofen suspension.

FIG. 6C: Particle Size Distribution of "Liquid Ketoprofen".

FIG. 6D: Comparison of Raman Spectra.

FIG. 7A: Optical Image of Naproxen dry powder (400× magnification).

FIG. 7B: Particle Size Distribution of Naproxen suspension.

FIG. 7C: Particle Size Distribution of "Liquid Naproxen".

FIG. 7D: Comparison of Raman Spectra.

FIG. 8A: Dry Aspirin at 100× magnification.

FIG. 8B: Formula 1 at 100× Magnification.

FIG. 8C: Formula 1C at 100× Magnification.

FIG. 8D: Formula 2 at 100× Magnification.

FIG. 8E: Formula 3 at 100× Magnification.

FIG. 8F: Dry Aspirin Suspension at 400× magnification.

FIG. 8G: Laser Diffraction Result for Dry Aspirin at 2.2% in Water.

DETAILED DESCRIPTION OF THE INVENTION

Transdermal and/or dermal compositions (e.g., liquids) that stabilize and/or reduce the particle size of active ingredients in the formulation, such as, non-steroidal anti-inflammatory drugs (NSAIDs), acetaminophen, and/or proteins or polypeptides, such as insulin, have been developed. Evidence is provided herein that transdermal and/or dermal formulations comprising NSAIDs, acetaminophen, and/or proteins such as insulin, wherein greater than 90% of the particles of the active ingredient have a particle size of less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering (DLS), using a volume-weighted particle size distribution calculation method, can be prepared. Evidence is also provided herein that these transdermal and/or dermal formulations stabilize the active ingredients in liquid for extended periods of time. The reduced particle size of the NSAID, acetaminophen, and/or insulin and the stability in liquid afforded by the formulation described herein, is contemplated to improve transdermal and/or dermal delivery of the active ingredient, as well as, improve the shelf-life of the product.

Aspects of the invention include a transdermal and/or dermal composition (e.g., liquid) comprising alcohol (e.g., absolute ethanol), an NSAID (e.g., aspirin), acetaminophen, and/or a protein (e.g., insulin, collagen, or elastin) water, approximately 4%-25% by weight or volume of an ethoxylated oil having 10, 11, 12, 13, 14, 15, 16, 17, 18, 19, 20, 21, or 22 ethoxylations per molecule (e.g., ethoxylated macadamia nut oil having 16 ethoxylations per molecule), and optionally, a fragrance, wherein greater than or equal to or any number in between 90%, 91%, 92%, 93%, 94%, 95%, 96%, 97%, 98%, or 99% of the NSAID, acetaminophen, and/or insulin particles in the composition (e.g., liquid) have a particle size of less than or equal to 16, 15, 14, 13, 12, 11, 10, 9, 8, 7, 6, 5, or 4 nanometers, as determined by Dynamic Light Scattering (DLS), using a volume-weighted particle size distribution calculation method.

Many different types of alcohol may be used in a transdermal and/or dermal composition (e.g., liquid) prepared as described herein (e.g., isopropanol, amyl, ethanol, or an ethoxylated alcohol, such as Polyethylene glycol hexadecyl ether (BRIJ), which may be used alone or in addition to one of the other aforementioned alcohols). Desirably, the amount of alcohol (e.g., 200 proof ethyl alcohol) in the transdermal and/or dermal liquid formulations described herein is greater than or equal to or any number in between 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, or 60% of the total volume or weight of the transdermal and/or dermal liquid. Preferably, the amount of alcohol (e.g., 200 proof ethyl alcohol) in the afore-mentioned transdermal and/or dermal composition (e.g., liquid) is greater than or equal to or any number in between 48%, 49%, 50%, 51%, or 52% of the total volume or weight of the transdermal and/or dermal composition (e.g., liquid). Most preferably, the amount of alcohol (e.g., 200 proof ethyl alcohol) in the afore-mentioned transdermal and/or dermal composition (e.g., liquid) is greater than or equal to or any number in between, 49%, 50%, or 51% of the total volume or weight of the transdermal and/or dermal composition (e.g., liquid). In some preferred embodiments, the amount of alcohol (e.g., 200 proof ethyl alcohol) in the transdermal and/or dermal composition (e.g., liquid) is 50% of the total volume or weight of the transdermal and/or dermal composition (e.g., liquid).

A variety of active ingredients can be used in one or more of the transdermal and/or dermal compositions (e.g., liquids) described herein. The described embodiments can be organized according to their ability to deliver a low or high molecular weight active ingredient. Low molecular weight molecules (e.g., a molecule having a molecular weight less than 6,000 Daltons) can be effectively delivered using an embodiment of the invention and high molecular weight molecules (e.g., a molecule having a molecular weight equal to or greater than 6,000 Daltons) can be effectively delivered using an embodiment of the invention. Desirably a transdermal and/or dermal composition (e.g., liquid) described herein comprises an active ingredient having a molecular weight of 50 Daltons to less than 6,000 Daltons. Preferably, however, a transdermal and/or dermal composition (e.g., liquid) described herein comprises an active ingredient having a molecular weight of 50 Daltons to 2,000,000 Daltons or less. That is, a preferred transdermal and/or dermal composition (e.g., liquid) described herein comprises an active ingredient having a molecular weight of less than or equal to or any number in-between 50, 100, 200, 500, 1,000, 1,500, 2,000, 2,500, 3,000, 3,500, 4,000, 4,500, 5,000, 5,500, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 56,000, 57,000, 58,000, 59,000, 60,000, 61,000, 62,000, 63,000, 64,000, 65,000, 66,000, 67,000, 68,000, 69,000, 70,000, 75,000, 80,000, 85,000, 90,000, 95,000, 100,000, 125,000, 150,000, 175,000, 200,000, 225,000, 250,000, 275,000, 300,000, 350,000, 400,000, 450,000, 500,000, 600,000, 700,000, 800,000, 900,000, 1,000,000, 1,500,000, 1,750,000, and 2,000,000 Daltons.

In terms of low molecular weight active ingredients, a variety of NSAIDs can be provided in one or more of the transdermal and/or dermal compositions (e.g., liquids) described herein. In some embodiments, one or more of the following NSAIDs are included in the transdermal composition (e.g., liquid): ibuprofen (2-(isobutylphenyl)-propionic acid); methotrexate (N-[4-(2,4 diamino6-pteridinyl-methyl]methylamino]benzoyl)-L-glutamic acid); aspirin (acetylsalicylic acid); salicylic acid; diphenhydramine (2-(diphenylmethoxy)-NN-dimethylethylamine hydrochloride); naproxen (2-naphthaleneacetic acid, 6-methoxy-9-methyl-, sodium salt, (−)); phenylbutazone (4-butyl-1,2-diphenyl-3, 5-pyrazolidinedione); sulindac-(2)-5-fuoro-2-methyl-1-[[p-(methylsulfinyl)phenyl]methylene-]-1H-indene-3-acetic acid; diflunisal (2',4',-difluoro-4-hydroxy-3-biphenylcarboxylic acid; piroxicam (4-hydroxy-2-methyl-N-2-pyridinyl-2H-1,2-benzothiazine-2-carboxamide 1,1-dioxide, an oxicam; indomethacin (1-(4-chlorobenzoyl)-5-methoxy-2-methyl-H-indole-3-acetic acid); meclofenamate sodium (N-(2,6-dichloro-m-tolyl) anthranilic acid, sodium salt, monohydrate); ketoprofen (2-(3-benzoylphenyl)-propionic acid; tolmetin sodium (sodium 1-methyl-5-(4-methylbenzoyl-1H-pyrrole-2-acetate dihydrate); diclofenac sodium (2-[(2,6-dichlorophenyl)amino]benzeneatic acid, monosodium salt); hydroxychloroquine sulphate (2-{[4-[(7-chloro-4-quinolyl)amino]pentyl]ethylamino}ethanol sulfate (1:1); penicillamine (3-mercapto-D-valine); flurbiprofen ([1,1-biphenyl]-4-acetic acid, 2-fluoro-alphamethyl-, (+−)); cetodolac (1-8-diethyl-13,4,9, tetra hydropyrano-[3-4-13]indole-1-acetic acid; mefenamic acid (N-(2,3-xylyl)anthranilic acid; and diphenhydramine hydrochloride (2-diphenyl methoxy-N, N-di-methylethamine hydrochloride). Preferably, a transdermal and/or dermal composition (e.g., liquid) prepared as described herein comprises one or more of the following NSAIDs: ibuprofen, ketoprofen, naproxen, aspirin, salicylic acid, indomethacin, fenoprofen, tolmetin, sulindac, meclofenamate, proxicam, flurbiprofen, or diclofenac (sodium or epolamine). In some embodiments, the transdermal and/or dermal composition (e.g., liquid) prepared as described herein comprises one or more of ibuprofen, ketoprofen, naproxen, aspirin, or salicylic acid.

In some embodiments, when the active ingredient is a dry reagent, for example, desirably, the amount of active ingredient (e.g., a low molecular weight active ingredient, such as an NSAID or acetaminophen) in the transdermal and/or dermal composition (e.g., liquid) is greater than or equal to or any number in between 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%., 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.25%, 5.5%, 5.8%, 6.0%, 6.25%, 6.5%, 6.8%, 7.0%, 7.25%, 7.5%, 7.8%, 8.0% 8.25%, 8.5%, 8.8%, 9.0%, 9.25%, 9.5%, 9.8%, 10.0%, 10.25%, 10.5%, 10.8%, 11.0%, 11.25%, 11.5%, 11.8%, or 12.0% of the total volume or weight of the transdermal and/or dermal composition (e.g., liquid). Preferably, the amount of active ingredient (e.g., an NSAID or acetaminophen) in the transdermal and/or dermal composition (e.g., liquid) formulation is greater than or equal to or any number in between 1.5%, 1.6%, 1.7%, 1.8%, 1.9%, 2.0%, 2.1%, 2.2%., 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.25%, 5.5%, 5.8%, 6.0%, 6.25%, 6.5%, 6.8%, 7.0%, 7.25%, 7.5%, 7.8%, 8.0% 8.25%, 8.5%, 8.8%, 9.0%, 9.25%, 9.5%, 9.8%, 10.0%, 10.25%, 10.5%, 10.8%, 11.0%, 11.25%, 11.5%, 11.8%, or 12.0% of the total volume or weight of the transdermal and/or dermal composition (e.g., liquid). More preferably, the amount of active ingredient (e.g., an NSAID or acetaminophen) in the transdermal and/or dermal composition (e.g., liquid) is greater than or equal to or any number in between 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.25%, 5.5%, 5.8%, 6.0%, 6.25%, 6.5%, 6.8%, 7.0%, 7.25%, 7.5%, 7.8%, 8.0% 8.25%, 8.5%, 8.8%, 9.0%, 9.25%, 9.5%, 9.8%, 10.0%, 10.25%, 10.5%, 10.8%, 11.0%, 11.25%, 11.5%, 11.8%, or 12.0% of the total volume or weight of the transdermal and/or dermal composition (e.g., liquid). Most preferably, the amount of active ingredient (e.g., an NSAID or acetaminophen) in the transdermal and/or dermal composition (e.g., liquid) is greater than or equal to or any number in between 2.0%, 2.1%, 2.2%., 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.25%, 5.5%, 5.8%, 6.0%, 6.25%, 6.5%, 6.8%, 7.0%, 7.25%, 7.5%, 7.8%, 8.0%, 8.25%, 8.5%, 8.8%, 9.0%, 9.25%, 9.5%, 9.8%, 10.0%, 10.25%, 10.5%, 10.8%, 11.0%, 11.25%, 11.5%, 11.8%, or 12.0% of the total volume or weight of the transdermal and/or dermal composition (e.g., liquid). In some preferred embodiments, the amount of active ingredient (e.g., an NSAID or acetaminophen) in the transdermal and/or dermal composition (e.g., liquid) formulation is greater than or equal to or any number in between 2.0%, 2.1%, 2.2%., 2.3%, 2.4%, or 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.25%, 5.5%, 5.8%, 6.0%, 6.25%, 6.5%, 6.8%, 7.0%, 7.25%, 7.5%, 7.8%, 8.0% 8.25%, 8.5%, 8.8%, 9.0%, 9.25%, 9.5%, 9.8%, 10.0%, 10.25%, 10.5%, 10.8%, 11.0%, 11.25%, 11.5%, 11.8%, or 12.0% of the total volume or weight of the transdermal and/or dermal composition (e.g., liquid).

A large number of poly peptides and/or proteins can also be incorporated into one or more of the transdermal and/or dermal composition (e.g., liquid) formulations described herein. Collagens and elastins exist in many forms and can be isolated from a number of sources. Additionally, several forms of collagen can be obtained commercially (e.g., Sederma, New Jersey). Many low molecular weight collagens and elastins can be made, for example, by hydrolysis or protease digestion. Several transdermal and/or dermal compositions (e.g., liquids) described herein comprise collagens and/or elastins having molecular weights less than or equal to 6,000 Daltons (e.g., achievable by limited enzymatic digestion or hydrolysis). Additionally, several higher molecular weight collagens and elastins exist. Some are isolated from animal or plant sources and some are synthesized or produced through techniques common in molecular biology. Several transdermal and/or dermal compositions (e.g., liquids) described herein comprise collagens and/or elastins having molecular weights greater than or equal to 1,000 Daltons to greater than 2,000,000 Daltons. That is, embodiments of the transdermal and/or dermal compositions (e.g., liquids) described herein comprise collagens and/or elastins having molecular weights of greater than or equal to or any number in-between 1,000, 1,500, 2,000, 2,500, 3,000, 3,500, 4,000, 4,500, 5,000, 5,500, 6,000, 7,000, 8,000, 9,000, 10,000, 11,000, 12,000, 13,000, 14,000, 15,000, 16,000, 17,000, 18,000, 19,000, 20,000, 21,000, 22,000, 23,000, 24,000, 25,000, 26,000, 27,000, 28,000, 29,000, 30,000, 31,000, 32,000, 33,000, 34,000, 35,000, 36,000, 37,000, 38,000, 39,000, 40,000, 41,000, 42,000, 43,000, 44,000, 45,000, 46,000, 47,000, 48,000, 49,000, 50,000, 51,000, 52,000, 53,000, 54,000, 55,000, 56,000, 57,000, 58,000, 59,000, 60,000, 61,000, 62,000, 63,000, 64,000, 65,000, 66,000, 67,000, 68,000, 69,000, 70,000, 75,000, 80,000, 85,000, 90,000, 95,000, 100,000, 125,000, 150,000, 175,000, 200,000, 225,000, 250,000, 275,000, 300,000, 350,000, 400,000, 450,000, 500,000, 600,000, 700,000, 800,000, 900,000, 1,000,000, 1,500,000, 1,750,000, and 2,000,000 Daltons.

A variety of insulins can also be provided in one or more of the transdermal and/or dermal compositions (e.g., liquids) provided herein including, but not limited to, human insulin, recombinant insulin, porcine insulin, bovine insulin, and/or modified insulin (e.g., hexyl-insulin monoconjugate 2 (HIM2)). The amount of insulin in a transdermal and/or dermal composition (e.g., liquid) prepared as described herein can also vary widely depending on the patient being treated and the desired amount of insulin that is to be delivered to the patient. Desirably, the amount of insulin in the transdermal and/or dermal composition (e.g., liquid) is greater than or equal to or any number in between 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, or 120 units of insulin per milliliter of transdermal and/or dermal composition (e.g., liquid). Preferably, the amount of insulin in the transdermal and/or dermal composition (e.g., liquid) formulation is greater than or equal to or any number in between 90, 91, 92, 93, 94, 95, 96, 97, 98, 99, 100, 101, 102, 103, 104, or 105 units of insulin per ml of transdermal and/or dermal composition (e.g., liquid). Most preferably, the amount of insulin in the transdermal and/or dermal composition (e.g., liquid) is greater than or equal to or any number in between 95, 96, 97, 98, 99, 100, 101, or 102 units of insulin per ml of transdermal and/or dermal composition (e.g., liquid). In some preferred embodiments, the amount of insulin in the transdermal and/or dermal composition (e.g., liquid) is 100 units of insulin per ml of transdermal and/or dermal composition (e.g., liquid).

Stated differently, the amount of insulin in a transdermal and/or dermal composition (e.g., liquid) described herein can be greater than or equal to or any number in between 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, or 2.0% of the total volume or weight of the transdermal and/or dermal composition (e.g., liquid). Preferably, the amount of insulin in a transdermal and/or dermal composition (e.g., liquid) described herein can be greater than or equal to or any number in between 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, or 0.3% of the total volume or weight of the transdermal and/or dermal composition (e.g., liquid). More preferably, the amount of insulin in a transdermal and/or dermal composition (e.g., liquid) described herein can be greater than or equal to or any number in between 0.15%, 0.16%, 0.17%, 0.18%, 0.19%, 0.2%, 0.21%, 0.22%, 0.23%, 0.24%, or 0.25% of the total volume or weight of the transdermal and/or dermal composition (e.g., liquid). In preferred embodiments, the amount of insulin in a transdermal and/or dermal composition (e.g., liquid) is 0.2% of the total volume or weight of the transdermal and/or dermal composition (e.g., liquid).

Stated in yet another way, the amount of insulin in a transdermal and/or dermal composition (e.g., liquid) described herein is adjusted according to the patient's weight and/or treatment needs. For example, the amount of insulin in a transdermal and/or dermal composition (e.g., liquid) can be an amount that provides to a patient an amount of insulin in one, two, three, or more applications that is greater than or equal to or any number in between 0.5 g, 0.6 g, 0.7 g, 0.8 g, 0.9 g, 1.0 g, 1.1 g, 1.2 g, or 1.3 g of insulin per kg of patient body weight per day.

Using the aforementioned formulations as guiding principles, additional proteins can be provided in one or more of the transdermal and/or dermal compositions (e.g., liquids) provided herein. That is, for example, polypeptides and/or proteins that can be included in one or more of the transdermal compositions (e.g., liquids) described herein include: vasopressin, vasopressin polypeptide analogs, desmopressin, glucagon, corticotropin (ACTH), gonadotropin, calcitonin, C-peptide of insulin, parathyroid hormone (PTH), hepatocyte growth factor (HGF), growth hormone (HG), human growth hormone (hGH), growth hormone releasing hormone (GHRH), oxytocin, corticotropin releasing hormone (CRH), somatostatin or somatostatin polypeptide analogs, gonadotropin agonist or gonadotropin agonist polypeptide analogs, human atrial natriuretic peptide (ANP), human thyroxine releasing hormone (TRH), follicle stimulating hormone (FSH), prolactin, insulin like growth factor-I (IGF-I) somatomedin-C(SM-C), calcitonin, leptin and the leptin derived short peptide OB-3, melatonin, GLP-1 or Glucagon-like peptide-1, GiP, neuropeptide pituitary adenylate cyclase, GM-1 ganglioside, nerve growth factor (NGF), nafarelin, D-tryp6)-LHRH, FGF, VEGF antagonists, leuprolide, interferon (e.g., alpha, beta, or gamma) low molecular weight heparin, PYY, LHRH antagonists, Keratinocyte Growth Factor (KGF), Glial-Derived Neurotrophic Factor (GDNF), ghrelin, and ghrelin antagonists.

Using the aforementioned formulations as guiding principles, additional molecules can be provided in one or more of the transdermal and/or dermal compositions (e.g., liquids) provided herein. That is, for example, additional active ingredients that can be included in one or more of the transdermal and/or dermal compositions (e.g., liquids) described herein include: sex hormones, such as, estradiol, diethylstilbestrol, conjugated estrogens, estrone, norethindrone, medroxyprogesterone, progesterone, norgestrel, testosterone, methyltestosterone, fluoxymesterone, or thymosin beta-4; anabolic steroids, such as, androstenediol methandrostenolone, androstenedione methenolone, boldenone, methyltestosterone, chlorotestosterone (4-chlortestosterone) mibolerone, clostebol, methandriol, dehydrochlormethyltestosterone nandrolone, dehydroepiandrosterone (DHEA) norandrostenediol, dihydrotestosterone (DHT) norandrostenedione, dromostanolone norethandrolone, drostanolone oxandrolone, epitrenbolone, oxymesterone, ethylestrenol oxymetholone, fluoxymesterone stanolone, formebulone, stanozolol, gestrinone testolactone, mesterolone testosterone, methandienone, tetrahydrogestrinone (THG), or methandranone trenbolone; steroidal anti-inflammatory agents such as, corticosteroids such as hydrocortisone, hydroxyltriamcinolone alphamethyl dexamethasone, dexamethasone-phosphate, beclomethasone dipropionate, clobetasol valerate, desonide, desoxymethasone, desoxycorticosterone acetate, dexamethasone, dichlorisone, diflorasone diacetate, diflucortolone valerate, fluadrenolone, fluclarolone acetonide, fludrocortisone, flumethasone pivalate, fluosinolone acetonide, fluocinonide, flucortine butylester, fluocortolone, fluprednidene (fluprednylidene)acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenalone acetonide, medrysone, amc, amcinafide, betamethasone and the balance of its esters, chlorprednisone, chlorprednisone acetate, clocortelone, clescinolone, dichlorisone, difluprednate, flucloronide, flunisolide, fluoromethalone, fluperolone, fluprednisolone, hydrocortisone valerate, hydrocortisone cyclopentylproprionate, hydrocortamate, meprednisone, paramethasone, prednisolone, prednisone, beclomethasone dipropionate, betamethasone dipropionate, triamcinolone, and combinations thereof; antibiotic agents, such as, chloramphenicol; synthetic and semi-synthetic penicillins; beta-lactames; quinolones; fluoroquinolnes; macrolide antibiotics; peptide antibiotics; cyclosporines; erythromycin; clinndamycin; antibiotics of the lincomycin family; antibiotics of the tetracycline family; and sulfur-based antibiotics, such as sulfonamides. Exemplary antibiotics of the lincomycin family include lincomycin (6,8-dideoxy-6-[[(1-methyl-4-propyl-2-pyrrolidinyl)-carbonyl]amino]-1-thio-L-threo-alpha-D-galacto-octopyranoside), clindamycin, the 7-deoxy, 7-chloro derivative of lincomycin (i.e., 7-chloro-6,7,8-trideoxy-6-[[(1-methyl-4-propyl-2-pyrrolidinyl)carbonyl]am-ino]-1-thio-L-threo-alpha-D-galacto-octopyranoside), and other known analogs and/or related. Exemplary antibiotics of the tetracycline family, which may be included in a formulation described herein include tetracycline (4-(dimethylamino)1,4,4-alpha-,5,5-alpha-,6,11,12 alpha-octahydro-3,-6,12-,12-alpha-pentahydroxy-6-methyl-1,11-dioxo-2naphthacenecarboxamide)-chlortetracycline, oxytetracycline, tetracycline, demeclocycline, rolitetracycline, methacycline and doxycycline and their pharmaceutically acceptable salts and esters. Exemplary sulfur-based antibiotics include, which may be included in one or more of the formulations described herein include the sulfonamides sulfacetamide, sulfabenzamide, sulfadiazine, sulfadoxine, sulfamerazine, sulfanethazine, sulfamethizole, sulfamethoxazole, and pharmacologically acceptable salts and esters thereof, such as sulfacetamide sodium. Anti-viral agents for use with the formulations described herein include reverse transcriptase inhibitors such as Nevirapine, Delavirdine, and Efavirenz; nucleoside reverse transcriptase inhibitors (nucleoside analogs) such as Zidovudine, Didanosine, Zalcitabine, Stavudine, Lamivudine, Abacavir, and Emtricitabine; protease inhibitors such as Amprenavir, Fosamprenavir, Indinavir, lopinavir, Ritonavir, Saquinavir, and Nelfinavir; and nucleotide analog reverse transcriptase inhibitors (NtARTIs or NtRTIs) such as Tenofovir and Adefovir. Ultra-violet (UV) blocking agents or sunscreen agents that may be incorporated into the formulations described herein include: UVB blocking agents such as salicylic acid derivatives, cinnamic acid derivatives, liquid beta, beta'-diphenylacrylate derivatives, p-aminobenzoic acid derivatives, 4-methylbenzylidene camphor, 2-phenylbenzimidazole-5-sulfonic acid, and 1,3,5-triazine derivatives; UVA blocking agents such as dibenzoylmethane derivatives, benzophenone derivatives, silane derivatives or polyorganosiloxanes containing a benzophenone group, anthranilates, silicon derivatives of N-substituted benzimidazolylbenzazoles or of benzofurylbenzazoles, and triazine derivatives; and combinations thereof. Anti-wrinkle agents for use with the formulations described herein include retinol and retinoic acid derivatives, such as 13-trans retinoic acid, 13-cis retinoic acid and retinyl ester; hydroxy acids, such as hydroxy acid, alpha hydroxy acid, beta hydroxy acid, poly hydroxy acid, glycolic acid, and lactic acid; exfoliants; Coenzyme Q10 copper peptides; kinetins; hyaluronic acid and tea extracts; as well as the aforementioned collagens and elastins. Anti-malarial agents for use with the formulations described herein include quinine; quinimax; quinidine; chloroquine and derivatives such as chloroquine phosphate and hydroxychloroquine; amodiaquine; pyrimethamine; sulphadoxine; proguanil; mefloquine; atovaquone; primaquine; artemesinin; halofantrine; doxycycline; and clindamycin. In some embodiments an active ingredient comprises a sugar or a sugar-containing compound such as a cyclodextrin or beta-cyclodextrin. Pain-management and additional agents for use with the formulations described herein include opioids, anti-depressants, anti-epileptic, adjuvant medications, muscle relaxer, nerve abalation, spinal chord stimulators, nutraceuticals, vitamins for improved nutrition, minerals, neuropathy therapy, hormonal balancing (male & female), and bio-identical hormones.

Many different ethoxylated oils can be used to prepare a transdermal and/or dermal composition (e.g., liquid), as described herein (e.g., macadamia nut oil, meadow foam oil, jojoba oil, emu oil, and/or synthetic oil). Preferably, these ethoxylated oils have been ethoxylated to have 10, 11, 12, 13, 14, 15, 16, 17, 18, 19, 20, 21, or 22 ethoxylations per molecule. Preferably, the ethoxylated oils used in the preparations described herein have 16, 17, or 18 ethoxylations per molecule and most preferable are ethoxylated oils having 16 ethoxylations per molecule. In some embodiments, macadamia nut oil having 16 ethoxylations per molecule is used in the transdermal compositions (e.g., liquids) described herein.

The amount of the aforementioned ethoxylated oils to include in a transdermal and/or dermal composition (e.g., liquid) is preferably greater than or equal to or any number in between 2%-25% by total weight or volume. That is, the amount of ethoxylated oil that can be incorporated into a transdermal composition (e.g., liquid), as described herein, can be greater than or equal to or any number in between 2.0%, 2.25%, 2.5%, 2.75%, 3.0%, 3.25%, 3.5%, 3.75%, 4.0%, 4.25%, 4.5%, 4.75%, 5.0%, 5.25%, 5.5%, 5.75%, 6.0%, 6.25%, 6.5%, 6.75%, 7.0%, 7.25%, 7.5%, 7.75%, 8.0% 8.25%, 8.5%, 8.75%, 9.0%, 9.25%, 9.5%, 9.75%, 10.0%, 10.25%, 10.5%, 10.75%, 11.0%, 11.25%, 11.5%, 11.75%, 12.0%, 12.25%, 12.5%, 12.75%, 13.0%, 13.25%, 13.5%, 13.75%, 14.0%, 14.25%, 14.5%, 14.75%, 15.0%, 15.5%, 16.0%, 16.5%, 17.0%, 17.5%, 18.0%, 18.5%, 19.0%, 19.5%, 20.0%, 20.5%, 21.0%, 21.5%, 22.0%, 22.5%, 23.0%, 23.5%, 24.0%, 24.5%, or 25.0%.

The amount of water in the transdermal and/or dermal composition (e.g., liquid) varies according to the amount of alcohol, active ingredient, and ethoxylated oil present. That is, for example, when making 100 ml of a transdermal and/or dermal composition (e.g., liquid), as described herein, the water is used to bring the volume of the emulsion comprising the alcohol, ethoxylated oil, and active ingredient with or without fragrance up to the total volume of 100 ml.

As described in greater detail below, it is contemplated that the water should be added to the transdermal and/or dermal composition (e.g., liquid) subsequent to the addition of the active ingredient to the alcohol and/or ethoxylated oil so as to protect the active ingredient from degradative forces (e.g., hydrolysis) and force particle size reduction of the active ingredient, which will improve stability and skin penetration. A variety of fragrances can be added to the transdermal liquids described herein (e.g., Peace and Calming oil, Sandal Wood Oil, or Tangerine oil). It is preferred that the fragrances are added to the transdermal composition (e.g., liquid) after the addition of water.

One approach to making the transdermal and/or dermal composition (e.g., liquid) described herein involves mixing an amount (e.g., 1%-70%, e.g. 30%-70%, or 30%-60% by total weight or volume or any number in between this range, as described supra) of alcohol (e.g., 200 proof ethyl alcohol) with an amount (e.g., 0.5%-12.0% by total weight or volume or any number in between this range, as described supra) of an active ingredient, such as an NSAID (e.g., aspirin), acetaminophen, or a protein such as, insulin while stirring the alcohol continuously with a stir plate and magnetic stir bar. When insulin is the active ingredient, the amount of insulin added to the formulation can be an amount sufficient to achieve a final concentration of 80-120 units insulin per ml or any number in between this range, as described supra. Once the active ingredient has mixed with the alcohol, an amount (e.g., 2%-25% by total weight or volume or any number in between either of these ranges, as described supra) of ethoxylated oil (e.g., macadamia nut oil having 10, 11, 12, 13, 14, 15, 16, 17, 18, 19, 20, 21, or 22 ethoxylations per molecule) is added to the alcohol and active ingredient mixture while continuously stirring so as to generate a nano-emulsion. Once the nano-emulsion has formed, water (e.g., distilled water) is added, preferably in a dropwise fashion, to bring the remaining volume up to the total volume of the preparation.

For example, by one such preparation approach, a 100 ml transdermal and/or dermal composition (e.g., liquid) preparation is prepared by mixing 50 ml of absolute ethanol with 2.2 grams of aspirin powder while stirring continuously; adding 10 ml of ethoxylated macadamia nut oil (16 ethoxylations per molecule) to the alcohol and aspirin mixture while stirring so as to generate an emulsion; and bringing the total remaining volume up to 100 ml by adding distilled water in a drop-wise fashion. Optionally, fragrance is added after adding the water. Additional steps of column chromatography (e.g., size exclusion or reverse phase HPLC or FPLC) can also be employed so as to separate, isolate and/or purify a transdermal and/or dermal composition (e.g., liquid) having an active ingredient that is of a relatively homogeneous size (e.g., a transdermal and/or dermal composition (e.g., liquid) having a size of active ingredient that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering (DLS), using a volume-weighted particle size distribution calculation method).

Another approach that can be used to make the transdermal and/or dermal compositions (e.g., liquids) described herein involves mixing an amount (e.g., 2%-25% by total weight or volume or any number in between this range, as described supra) of ethoxylated oil (e.g., macadamia nut oil having 10, 11, 12, 13, 14, 15, 16, 17, 18, 19, 20, 21, or 22 ethoxylations per molecule) with an amount (e.g., 0.5%-12.0% by total weight or volume or any number in between this range, as described supra) of an active ingredient, such as an NSAID (e.g., aspirin), acetaminophen, or a protein, such as insulin, while stirring the ethoxylated oil continuously (e.g., with a stir plate and magnetic stir bar). When insulin is the active ingredient, e.g., the amount of insulin added to the formulation can be an amount sufficient to achieve a final concentration of 80-120 units insulin per ml or any number in between this range, as described supra. Next, an amount (e.g., 1%-70%, e.g. 30%-70%, by total weight or volume or any number in between this range, as described supra) of alcohol (e.g., 200 proof ethyl alcohol) is added to the ethoxylated oil and active ingredient mixture while stirring continuously. Once a nano-emulsion has formed, water (e.g., distilled water) is added, preferably in a dropwise fashion, to bring the remaining volume up to the total volume of the preparation.

For example, by one such preparation approach, a 100 ml transdermal and/or dermal composition (e.g., liquid) preparation is prepared by mixing 10 ml of ethoxylated macadamia nut oil (16 ethoxylations per molecule) with 2.2 grams of aspirin powder while stirring continuously; adding 50 ml of absolute ethanol to the ethoxylated oil and aspirin mixture while stirring so as to generate a nano-emulsion; and bringing the total remaining volume up to 100 ml by adding distilled water in a drop-wise fashion. Optionally, fragrance is added after adding the water. Additional steps of column chromatography (e.g., size exclusion or reverse phase HPLC or FPLC) can also be employed so as to separate, isolate and/or purify a transdermal composition (e.g., liquid) having an active ingredient that is of a relatively homogeneous size and having a size of the active ingredient that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering (DLS), using a volume-weighted particle size distribution calculation method).

The transdermal and/or dermal compositions (e.g., liquids) described herein can be introduced into a container, e.g., a bottle that preferably has a convenient applicator (e.g., sprayer, roller ball, or roll-on applicator). The applicators can also be configured such that a measured amount of a transdermal and/or dermal composition (e.g., liquid) is provided with each application such that an effective dose of the active ingredient can be administered.

The a transdermal and/or dermal compositions (e.g., liquids) made in accordance with the teachings herein comprise greater than or equal to or any number in between 90%, 91%, 92%, 93%, 94%, 95%, 96%, 97%, 98%, or 99% of the particles of active ingredient with a particle size of less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering (DLS), using a volume-weighted particle size distribution calculation method, which is considerably less than the particle size of the active ingredient prior to formulation in accordance with the methods described herein. Without being bound to any theory, it is contemplated that the mixing of the active ingredient with the alcohol and/or ethoxylated oil prior to contacting the active ingredient with water, promotes a reduction of particle size of the active ingredient. This reduced particle size and the nano-emulsion generated by the methodologies provided herein is also thought to protect the active ingredient from degradation e.g., from hydrolysis, and thereby provide greater stability of the active ingredient, which improves shelf-life of the product, and the dermal and/or transdermal delivery of the active ingredient.

In a first set of experiments, it was unexpectedly discovered that a transdermal and/or dermal composition (e.g., liquid) prepared in accordance with the teachings herein, have an active ingredient particle size that is substantially reduced, as compared to the particle size of the active ingredient prior to it being diluted into a formulation. As shown in the Examples 4 and 8, when the NSAIDs: ibuprofen, ketoprofen, naproxen, and aspirin, the pain reliever acetamenophin, and insulin were formulated into a transdermal and/or dermal composition (e.g., liquid) in accordance with the teachings herein, a significant reduction in particle size of the NSAIDs, acetamenophin, and insulin as compared to the NSAIDs, acetaminophen, and insulin prior to formulation, was detected.

For example, with acetaminophen, based on DLS measurements, after formulation in accordance with the methods described herein, it was found that greater than 99% of acetaminophen particles were less than 10 nm in size, when a volume-weighted particle size distribution calculation was used. Prior to formulation, the particle size of the acetaminophen (dry powder) was extremely variable (1-100 microns in size). Similarly, when an ibuprofen-containing transdermal and/or dermal composition (e.g., liquid), prepared in accordance with the teachings herein, was analyzed by DLS, it was found that greater than 99.5% of the ibuprofen particles were less than 10 nm, when a volume-weighted particle size distribution calculation was used. But prior to formulation, the particle size of the ibuprofen (dry powder) was extremely variable (10-100 microns in size). A ketoprofen-containing transdermal and/or dermal composition (e.g., liquid), prepared in accordance with the teachings herein, was also analyzed by DLS and it was found that greater than 90% of the ketoprofen particles were less than 6 nm, when a volume-weighted particle size distribution calculation was used. But prior to formulation the particle size of the ketoprofen (dry powder) was extremely variable (10-100 microns in size). A naproxen-containing transdermal and/or dermal composition (e.g., liquid), prepared in accordance with the teachings herein, was also analyzed by DLS and it was found that greater than 99.9% of the naproxen particles were less than 12 nm, when a volume-weighted particle size distribution calculation was used. But prior to formulation the particle size of the naproxen (dry powder) was extremely variable (approximately, 100 microns in size). An aspirin-containing transdermal and/or dermal composition (e.g., liquid), prepared in accordance with the teachings herein, was also analyzed by DLS and it was found that the aspirin particles after formulation were approximately 12.3 nanometers in size but prior to formulation, the particle size of the aspirin (dry) was on average 670 microns. In another set of experiments, an insulin-containing transdermal and/or dermal composition (e.g., liquid), prepared in accordance with the teachings herein, was analyzed by DLS and it was found that greater than 90% of the insulin particles are less than 3 nm, when a volume-weighted particle size distribution calculation was used but prior to formulation 99.9% of the insulin had a particle size of about 6 nm in size.

It is contemplated that formulations prepared by an alternative method, wherein water is allowed to contact the active ingredient prior to mixing the active ingredient with an alcohol or ethoxylated oil or both will have considerably larger size of active ingredient particles, with greater heterogeneity in size of particles and these formulations will be less stable and will have a shorter shelf-life than formulations prepared in accordance with the teachings provided herein.

Additional aspects of the invention concern methods of reducing particle size of an active ingredient (e.g., an NSAID, such as aspirin, acetaminophen, or a polypeptide or protein, such as insulin) in a transdermal and/or dermal composition (e.g., liquid). These methods can be practiced by contacting an amount (e.g., 0.5%-12.0% by total weight or volume or any number in between this range, as described supra) of an active ingredient, such as an NSAID (e.g., aspirin), acetaminophen, or a protein, such as insulin with an amount (e.g., 1%-70%, e.g. 30%-70%, by total weight or volume or any number in between this range, as described supra) of alcohol (e.g., 200 proof ethyl alcohol) or an amount (e.g., 2%-25% by total weight or volume or any number in between this range, as described supra) of ethoxylated oil (e.g., macadamia nut oil having 10, 11, 12, 13, 14, 15, 16, 17, 18, 19, 20, 21, or 22 ethoxylations per molecule) while stirring continuously (e.g., with a stir plate and magnetic stir bar). When insulin is the active ingredient, the amount of insulin added to the formulation can be an amount sufficient to achieve a final concentration of 80-120 units insulin per ml or any number in between this range, as described supra. Optionally, once an emulsion has formed, water (e.g., distilled water) can be added, preferably in a dropwise fashion, to bring the remaining volume up to the total volume of the preparation desired. It is contemplated that the mixing of the active ingredient with the alcohol and/or the ethoxylated oil induces the reduction in particle size of the active ingredient in the transdermal and/or dermal liquid. Optionally, the methods above can include a step of measuring the particle size after the formulation is prepared or after the active ingredient is mixed with the alcohol and/or ethoxylated oil. See Example 4 and 8. Another optional step that can be performed with these methods includes separating, isolating and/or purifying the prepared formulation and/or the mixture of active ingredient with the alcohol and/or the ethoxylated oil (e.g., by separating the formulation and/or the mixture of active ingredient with the alcohol and/or the ethoxylated oil by HPLC or FPLC column chromatography (e.g., size exclusion chromatography)).

Similarly, another aspect of the invention concerns methods of improving the stability or preventing degradation or hydrolysis of an active ingredient (e.g., an NSAID, acetaminophen, or a protein, such as insulin) in a transdermal and/or dermal or oral or injectable composition (e.g., liquid). These methods can be practiced by contacting an amount (e.g., 0.5%-12.0% by total weight or volume or any number in between this range, as described supra) of an active ingredient, such as an NSAID (e.g., aspirin), acetaminophen, or a protein, such as insulin with an amount (1%-70%, e.g. 30%-70%, by total weight or volume or any number in between this range, as described supra) of alcohol (e.g., 200 proof ethyl alcohol) or an amount (e.g., 2%-25% by total weight or volume or any number in between this range, as described supra) of ethoxylated oil (e.g., macadamia nut oil having 10, 11, 12, 13, 14, 15, 16, 17, 18, 19, 20, 21 or 22 ethoxylations per molecule) while stirring continuously (e.g., with a stir plate and magnetic stir bar). When insulin is the active ingredient, the amount of insulin added to the formulation can be an amount sufficient to achieve a final concentration of 80-120 units insulin per ml or any number in between this range, as described supra. Optionally, once an emulsion has formed, water (e.g., distilled water) can be added, preferably in a dropwise fashion, to bring the remaining volume up to the total volume of the preparation desired. It is contemplated that the mixing of the active ingredient with the alcohol and/or the ethoxylated oil stabilizes the active ingredient in the composition (e.g., liquid), preventing degradation (e.g., proteolysis) and/or hydrolysis. Optionally, the methods above can include a step of measuring the stability of the formulation or the mixture of active ingredient, alcohol and/or ethoxylated oil after it is prepared (e.g., measuring the degradation or hydrolysis of the active ingredient by HPLC after high temperature and high humidity stress tests).

Yet more aspects of the invention concern methods of improving the solubility and/or bioavailability of an active ingredient (e.g., an NSAID, acetaminophen, or a protein, such as insulin) in a transdermal and/or dermal or oral or injectable composition (e.g., liquid). These methods can be practiced by contacting an amount (e.g., 0.5%-12.0% by total weight or volume or any number in between this range, as described supra) of an active ingredient, such as an NSAID (e.g., aspirin), acetaminophen, or a protein, such as insulin with an amount (e.g., 1%-70% or 30%-70% by total weight or volume or any number in between this range, as described supra) of alcohol (e.g., 200 proof ethyl alcohol) or an amount (e.g., 2%-25% by total weight or volume or any number in between this range, as described supra) of ethoxylated oil (e.g., macadamia nut oil having 10, 11, 12, 13, 14, 15, 16, 17, 18, 19, 20, 21 or 22 ethoxylations per molecule) while stirring continuously (e.g., with a stir plate and magnetic stir bar). When insulin is the active ingredient, the amount of insulin added to the formulation can be an amount sufficient to achieve a final concentration of 80-120 units insulin per ml or any number in between this range, as described supra. Optionally, once an emulsion has formed, water (e.g., distilled water) can be added, preferably in a dropwise fashion, to bring the remaining volume up to the total volume of the preparation desired. It is contemplated that the mixing of the active ingredient with the alcohol and/or the ethoxylated oil stabilizes the active ingredient in the composition (e.g., liquid), preventing degradation (e.g., proteolysis) and/or hydrolysis. Optionally, the methods above can include a step of measuring the solubility and/or bioavailability of the formulation or the mixture of active ingredient, alcohol and/or ethoxylated oil after it is prepared.

Additional embodiments concern methods of using the compositions (e.g., liquids) described herein to provide therapeutic benefit to subjects (e.g., humans, animals, and/or domestic pets). In some embodiments, a method of reducing pain, fever, and/or inflammation is practiced by providing one or more of the transdermal and/or dermal compositions (e.g., liquids) comprising an NSAID and/or acetaminophen, as described herein to a subject (human or animal) in need of a medicament that reduces pain, fever, and/or inflammation (e.g., a patient that has been diagnosed with acute pain, chronic pain, arthritis, inflammation, or a fever, all of which can be ascertained by routine clinical or diagnostic evaluation). Accordingly, in some embodiments, a subject (human or animal) is identified as one being in need of a transdermal and/or dermal composition (e.g., liquid) that provides a particle size of an NSAID (e.g., aspirin, ibuprofen, ketoprofen, naproxen, salicylic acid) and/or acetaminophen that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering, using a volume-weighted particle size distribution calculation method (e.g., a dermal and/or transdermal composition (e.g., liquid) having greater than 90% of the particles of the NSAID and/or acetaminophen having a particle size of less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering, using a volume-weighted particle size distribution calculation method). Such subjects can be identified by evaluation that said subjects are experiencing pain, fever, and/or inflammation and such subjects need a dermal and/or transdermal composition (e.g., liquid) that exhibits a stabilized NSAID or acetaminophen, or a dermal and/or transdermal liquid that has deep penetrance by virtue of the small particle size. Subjects are then provided one or more of the NSAID- and/or acetaminophen-containing transdermal and/or dermal compositions (e.g., liquids) prepared as described herein. Optionally, after administration of the transdermal and/or dermal composition (e.g., liquid) comprising the NSAID and/or acetaminophen, the subject is evaluated for pain reduction, fever reduction, and/or a reduction in inflammation.

Similarly, in some embodiments, a method of administering or providing insulin to a subject is practiced by providing one or more of the transdermal and/or dermal or oral or injectable compositions (e.g., liquids) comprising an amount of insulin, as described herein to a subject in need of a medicament that treats, ameliorates, or reduces diabetes or a condition associated with diabetes or an insulin deficiency (e.g., a patient that has been diagnosed with an insulin deficiency, or diabetes, all of which can be ascertained by routine clinical or diagnostic evaluation). Accordingly, in some embodiments, a subject is identified as one being in need of a composition (e.g., liquid) that provides a particle size of insulin or modified insulin that is less than or equal to 16 nanometers, as determined by Dynamic Light Scattering, using a volume-weighted particle size distribution calculation method (e.g., a dermal and/or transdermal composition (e.g., liquid) having greater than 90% of the particles of the insulin or modified insulin having a particle size of less than 16 nm, as determined by Dynamic Light Scattering, using a volume-weighted particle size distribution calculation method). Such subjects can be identified by evaluation that said subjects are experiencing a reduced production of insulin and such subjects need a transdermal and/or dermal or oral or injectable composition (e.g., liquid) that exhibits a stabilized insulin or modified insulin, or a transdermal and/or dermal liquid that has deep penetrance by virtue of the small particle size of the insulin. Subjects are then provided one or more of the insulins and/or modified insulin-containing compositions (e.g., liquids) prepared as described herein. Optionally, after administration of the compositions (e.g., liquids) comprising the insulin and/or modified insulin, the subject is evaluated for an increase in insulin and/or glucose tolerance.

Similarly, compositions useful for the delivery of an active ingredient as provided herein have a Z-avg particle size measured by dynamic light scattering of less than, equal to, or any number in between 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, such as 1 nm-100 nm, 1 nm-75 nm, 1 nm-50 nm, 1 nm-30 nm, 1 nm-25 nm, 1 nm-24 nm, 1 nm-23 nm, 1 nm-22 nm, 1 nm-21 nm, 1 nm-20 nm, 1 nm-19 nm, 1 nm-18 nm, 1 nm-17 nm, 2 nm-20 nm, 3 nm-20 nm, 4 nm-20 nm, 4 nm-19 nm, 4 nm-18 nm, 4 nm-17 nm, or 4 nm-16 nm. In these compositions the amount of alcohol (such as ethyl alcohol, for example) can be at a final concentration of less than or equal to any number including or in between 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65%, such as 20%-60%, 25%-55%, 30%-55%, 35%-55%, 40%-55%, 45%-55%, or 50%. In these compositions the amount of active ingredient in the formulation (including an NSAID (e.g., aspirin, ibuprofen, ketoprofen, or naproxen), acetaminophen, or a protein, such as insulin, collagen, or elastin) can be at a final concentration of less than or equal to or any number in between 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.5%, 6.0%, 6.5%, 7.0%, 7.5%, 8.0%, 8.5%, 9.0%, 9.5%, 10.0%, 10.5%, 11.0%, 11.5% or 12%. In these compositions, the amount of an ethoxylated oil (such as PEG-16 Macadamia Glycerides) can be present at a final concentration of less than or equal to or any number in between 4%, 5%, 6%, 7%, 8%, 9%, 10%, 11%, 12%, 13%, 14%, 15%, 16%, 17%, 18%, 19%, 20%, 21%, 22%, 23%, 24%, or 25%, such as 5%-20%, 5%-15%, 6%-14%, 7%-13%, 8%-12%, 9%-11% or 10%. In some embodiments, water is added to bring the transdermal and/or dermal composition to or near to its final volume, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70%, for example 25%, 26%, 27%, 28%, 29%, 30%, 31%, 32%, 33%, 34%, 35%, 36%, 37%, 38%, 39%, 40%, 41%, 42%, 43%, 44%, or 45%, or for example 30%, 31%, 32%, 33%, 34%, 35%, 36%, 37%, 38%, 39%, 40%, 41%, 42%, 43%, 44%, or 45%, within a modest error to accommodate for an additional additive as indicated below such as a fragrance. Optionally one or more viscosity-increasing agents can be added, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose; and optionally adding a fragrance or coloring or a fragrance and a coloring, at for example about 0.1% to about 1% by total weight or volume (that is, 0.09, 0.1, 0.2, 0.3, 0.4, 0.5, 0.6, 0.7, 0.8, 0.9, 1.0%, or up to 1.1%), which when calculated with the amount of water to be added the final volume is 100%.

Similarly, methods are provided herein, which are useful for the production of compositions useful for the delivery of an active ingredient as provided herein that have a Z-avg particle size measured by dynamic light scattering of less than, equal to, or any number in between 1 nm, 2 nm, 3 nm, 4 nm, 5 nm, 6 nm, 7 nm, 8 nm, 9 nm, 10 nm, 11 nm, 12 nm, 13 nm, 14 nm, 15 nm, 16 nm, 17 nm, 18 nm, 19 nm, 20 nm, 21 nm, 22 nm, 23 nm, 24 nm, 25 nm, 26 nm, 27 nm, 28 nm, 29 nm, 30 nm, 31 nm, 32 nm, 33 nm, 34 nm, 35 nm, 36 nm, 37 nm, 38 nm, 39 nm, 40 nm, 41 nm, 42 nm, 43 nm, 44 nm, 45 nm, 46 nm, 47 nm, 48 nm, 49 nm, 50 nm, 51 nm, 52 nm, 53 nm, 54 nm, 55 nm, 56 nm, 57 nm, 58 nm, 59 nm, 60 nm, 61 nm, 62 nm, 63 nm, 64 nm, 65 nm, 66 nm, 67 nm, 68 nm, 69 nm, 70 nm, 71 nm, 72 nm, 73 nm, 74 nm, 75 nm, 76 nm, 77 nm, 78 nm, 79 nm, 80 nm, 81 nm, 82 nm, 83 nm, 84 nm, 85 nm, 86 nm, 87 nm, 88 nm, 89 nm, 90 nm, 91 nm, 92 nm, 93 nm, 94 nm, 95 nm, 96 nm, 97 nm, 98 nm, 99 nm, 100 nm, such as 1 nm-100 nm, 1 nm-75 nm, 1 nm-50 nm, 1 nm-30 nm, 1 nm-25 nm, 1 nm-24 nm, 1 nm-23 nm, 1 nm-22 nm, 1 nm-21 nm, 1 nm-20 nm, 1 nm-19 nm, 1 nm-18 nm, 1 nm-17 nm, 2 nm-20 nm, 3 nm-20 nm, 4 nm-20 nm, 4 nm-19 nm, 4 nm-18 nm, 4 nm-17 nm, or 4 nm-16 nm. In these compositions the amount of alcohol (such as ethyl alcohol, for example) can be at a final concentration of less than or equal to any number including or in between 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, or 65%, such as 20%-60%, 25%-55%, 30%-55%, 35%-55%, 40%-55%, 45%-55%, or 50%. In these compositions the amount of active ingredient in the formulation (including an NSAID (e.g., aspirin, ibuprofen, ketoprofen, or naproxen), acetaminophen, or a protein (such as insulin, collagen, or elastin) can be at a final concentration of less than or equal to or any number in between 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9%, 2.0%, 2.1%, 2.2%, 2.3%, 2.4%, 2.5%, 2.6%, 2.7%, 2.8%, 2.9%, 3.0%, 3.1%, 3.2%, 3.3%, 3.4%, 3.5%, 3.6%, 3.7%, 3.8%, 3.9%, 4.0%, 4.1%, 4.2%, 4.3%, 4.4%, 4.5%, 4.6%, 4.7%, 4.8%, 4.9%, 5.0%, 5.5%, 6.0%, 6.5%, 7.0%, 7.5%, 8.0%, 8.5%, 9.0%, 9.5%, 10.0%, 10.5%, 11.0%, 11.5% or 12%. In these compositions, the amount of an ethoxylated oil (such as PEG-16 Macadamia Glycerides) can be present at a final concentration of less than or equal to any number in between 4%, 5%, 6%, 7%, 8%, 9%, 10%, 11%, 12%, 13%, 14%, 15%, 16%, 17%, 18%, 19%, 20%, 21%, 22%, 23%, 24%, or 25%, such as 5%-20%, 5%-15%, 6%-14%, 7%-13%, 8%-12%, 9%-11% or 10%. In some embodiments, water is added to bring the transdermal and/or dermal composition to or near to its final volume, such as 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, or 70%, for example 25%, 26%, 27%, 28%, 29%, 30%, 31%, 32%, 33%, 34%, 35%, 36%, 37%, 38%, 39%, 40%, 41%, 42%, 43%, 44%, or 45%, or for example 30%, 31%, 32%, 33%, 34%, 35%, 36%, 37%, 38%, 39%, 40%, 41%, 42%, 43%, 44%, or 45%, within a modest error to accommodate for an additional additive as indicated below such as a fragrance. Optionally one or more viscosity-increasing agents can be added, such as, a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose; and optionally adding a fragrance or coloring agent or a fragrance and a coloring agent, at for example about 0.1% to about 1% by total weight or volume (that is, 0.09, 0.1, 0.2, 0.3, 0.4, 0.5, 0.6, 0.7, 0.8, 0.9, 1.0%, or up to 1.1%), which when calculated with the amount of water to be added the final volume is 100%. In some embodiments the methods provided herein are useful for the production of said compositions comprise the following steps in order: mixing an amount of an above-mentioned active ingredient with an above-mentioned alcohol, adding an above-mentioned ethoxylated oil; optionally adding an amount of water to bring the transdermal and/or dermal composition to or substantially to its final volume; and optionally adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or optionally adding a fragrance or coloring or a fragrance and a coloring.

Similarly, disclosed herein are methods of making a transdermal and/or dermal composition (e.g., liquid) comprising the following steps in order: (a) mixing an amount of an active ingredient with an alcohol, which such alcohol is present at a final concentration of 1%-70%, e.g. 30%-70% by total weight or total volume of the transdermal and/or dermal composition (b) adding an ethoxylated oil, which is present at a final concentration of 2%-25% by total weight or total volume of the transdermal and/or dermal composition, to the mixture of (a); (c) optionally, adding an amount of water to bring the transdermal and/or dermal composition to its final volume; and (d) optionally, adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents.

Similarly, disclosed herein are methods of making a transdermal and/or dermal composition (e.g., liquid) comprising the following steps in order: (a) mixing an amount of an active ingredient with an alcohol, which such alcohol is present at a final concentration of 1%-70%, e.g. 30%-70%, by total weight or total volume of the transdermal and/or dermal composition (b) adding an ethoxylated oil, which is present at a final concentration of 2%-25% by total weight or total volume of the transdermal and/or dermal composition, to the mixture of (a); (c) optionally, adding an amount of water to bring the transdermal and/or dermal composition to its final volume and/or adding one or more fragrances or coloring agents to the mixture of (a) and (b); and (d) optionally, adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents, to the mixture of (a), (b) and (c).

In some embodiments of these methods, the addition of an ethoxylated oil, which may be present at a final concentration of 2%-25% by total weight or total volume of the transdermal and/or dermal composition (such as PEG-16 Macadamia Glycerides at 10%, for example), has a substantial impact on particle size as indicated by final Z-Avg values as measured by dynamic light scattering. Particle sizes may be over 100× smaller when an ethoxylated agent present at a final concentration of 2%-25% by total weight or total volume of the transdermal and/or dermal composition (such as PEG-16 Macadamia Glycerides at 10%, for example) is added compared to formulations where it is not added. This indicates that the addition of an ethoxylated oil, which is present at a final concentration of 2%-25% by total weight or total volume of the transdermal and/or dermal composition, has a substantial impact on final particle size or volume.

In some embodiments of these methods, the order of addition of the components has a substantial impact on particle size as indicated by final Z-Avg values as measured by dynamic light scattering. Particle sizes for compositions constituted following the sequential combination of components as disclosed in methods herein (constituted by practicing a method of making a transdermal and/or dermal composition (e.g., liquid) comprising the following steps in order: (a) mixing an amount of an active ingredient with an alcohol, which such alcohol is present at a final concentration of 1%-70%, e.g. 30%-70%, by total weight or total volume of the transdermal and/or dermal composition; (b) adding an ethoxylated oil, which is present at a final concentration of 2%-25% by total weight or total volume of the transdermal and/or dermal composition, to the mixture of (a); (c) adding an amount of water to bring the transdermal and/or dermal composition to its final volume; and (d) optionally, adding one or more viscosity-increasing agents such as, a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents or both), produce compositions having substantially smaller particle sizes than the sizes seen for formulations of compositions comprising the same constituents but assembled through a different order of constituent addition. For example, particle sizes for formulations wherein the order of addition is altered may yield particle sizes of greater than 100 nm, while compositions generated through the sequential addition of constituents as indicated herein yield particle sizes of 100 nm, less than 100 nm, less than 90 nm, less than 80 nm, less than 70 nm, less than 60 nm, less than 40 nm, less than 30 nm, or less than 20 nm, as indicated by final Z-Avg values as measured by dynamic light scattering.

Similarly, it is disclosed herein that the order of sequential addition of components is relevant to composition properties. Formulations useful for the delivery of an active ingredient were prepared using the components as disclosed herein, but differing in the order in which the components are added.

In formulation 1, the formulation was constituted by the following steps in order: (a) mixing an amount of an active ingredient with an alcohol, which is present at a final concentration of 30-70% by total weight or total volume of the transdermal and/or dermal composition; (b) adding an ethoxylated oil, PEG-16 Macadamia Glycerides, which is present at a final concentration of 2-25% by total weight or total volume of the transdermal and/or dermal composition, to the mixture of (a); (c) adding an amount of water, to bring the transdermal and/or dermal composition to its final volume; and optionally adding a minimal proportional volume of a fragrance and optionally adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents or both.

In formulation 1c, the formulation was constituted by the following steps in order: (a) mixing an amount of an active ingredient with an alcohol, which is present at a final concentration of 30-70% by total weight or total volume of the transdermal and/or dermal composition; (b) adding an amount of water to bring the transdermal and/or dermal composition to its final volume; and optionally adding a minimal proportional amount of a fragrance and optionally adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents or both. Formulation 1c was a control for formulation 1 and lacks PEG-16 Macadamia Glycerides.

In formulation 2, the formulation was constituted by the following steps in order: (a) mixing an amount of an active ingredient with an amount of water; (b) adding an alcohol, which is present at a final concentration of 30-70% by total weight or total volume of the transdermal and/or dermal composition; (c) adding an ethoxylated oil, PEG-16 Macadamia Glycerides, which is present at a final concentration of 2-25% by total weight or total volume of the transdermal and/or dermal composition, to the mixture of (a); and optionally adding a minimal proportional amount of a fragrance and optionally adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents or both.

In formulation 3, the formulation was constituted by the following steps in order: (a) mixing an amount of water with an ethoxylated oil, PEG-16 Macadamia Glycerides, which is present at a final concentration of 2-25% by total weight or total volume of the transdermal and/or dermal composition; (b) mixing an amount of an active ingredient; (c) optionally adding a minimal proportional amount of a fragrance; and (d) adding an alcohol, which is present at a final concentration of 30-70% by total weight or total volume of the transdermal and/or dermal composition and optionally adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents or both.

In formulation 4, the formulation was constituted by the following steps in order: (a) providing an amount of an alcohol, which is present at a final concentration of 30-70% by total weight or total volume of the transdermal and/or dermal composition; (b) adding an ethoxylated oil, PEG-16 Macadamia Glycerides, which is present at a final concentration of 2-25% by total weight or total volume of the transdermal and/or dermal composition, to the alcohol of (a); (c) adding an amount of water, to bring the transdermal and/or dermal composition to its final volume; and optionally adding a minimal proportional amount of a fragrance and optionally adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents or both.

When the above-mentioned formulations are constituted in the sequential order of the non-optional constituents as indicated above, it is observed by Dynamic Light Scattering that Z-avg values in nanometers for Formulation 1 are substantially smaller than those of Formulations 2, 3, and 4.

For example, Formulation 1 particles have a particle size that is less than or equal to or any number in between 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering (DLS), using a volume-weighted particle size distribution calculation method, wherein particles of Formulations 2, 3 and 4 are greater than 100 nm. In some embodiments, particles of Formulations 2, 3 and 4 are at least 2×, 5×, 6×, 7×, 8×, 9×, 10×, 20×, or greater than particles of Formulation 1.

Formulation 1c particle sizes are substantially greater than those of Formulas 2, 3, or 4.

In some embodiments water is optionally excluded from the compositions disclosed herein. That is, a 'dry' formulation 1 can constituted by the following steps in order: (a) mixing an amount of an active ingredient with an alcohol; (b) adding an ethoxylated oil, PEG 16 Mac, which is present at a final concentration of 2-25% by total volume of the transdermal and/or dermal composition, to the mixture of (a); (c) and optionally adding a minimal proportional volume of a fragrance and optionally adding one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose and/or one or more fragrances or coloring agents or both).

Similarly, 'dry' formulations having constituents as recited in the paragraph immediately above, but in which the order of addition of the active ingredient, the alcohol and the ethoxylated oil, PEG-16 Mac, which is present at a final concentration of 2-25% by total volume of the transdermal and/or dermal composition, is changed with respect to the 'dry' formulation above, the resulting particles are substantially larger than those observed by Dynamic Light Scattering to measure Z-avg values in nm for 'dry' formulation 1, above.

Although the invention has been described with reference to embodiments and examples, it should be understood that various modifications can be made without departing from the spirit of the invention.

Example 1

Provided in this Example is an approach to prepare a transdermal and/or dermal composition (e.g., liquid) comprising an NSAID, acetaminophen, or insulin, wherein greater than 90% of the particles of the NSAID, acetaminophen, or insulin are less than or equal to 13 nanometers in size, as determined by a volume-weighted particle size distribution calculation. An exemplary formulation is shown below, but alternative formulations can be made by substituting another NSAID, acetaminophen, or insulin for aspirin (see below). Additionally, as noted above, the amounts of alcohol, active ingredient, and/or ethoxylated oil can be altered within the ranges provided in this disclosure so long as the amount of water added is adjusted to accommodate the increase or decrease in weight or volume afforded by the alteration in the amount of alcohol, active ingredient, and/or ethoxylated oil.

Liquid Aspirin 2.2% Formulation (Quantity=100 g, which is approximately 100 mL).

Perform the following steps in order:
1. Provide 50 g of 200 Proof Ethyl Alcohol (approximately 50%).
2. Mix continuously with stir bar during preparation.
3. Slowly add 2.2±0.1 g USP grade aspirin.

4. Once the aspirin has mixed with the alcohol, slowly add 10 g (approximately 10%) of macadamia nut oil having 16 ethoxylations per molecule.
5. Once the emulsion has formed, add 37.7 ml of distilled or deionized water, dropwise (approximately 38%).
6. Add 0.13 g Peace & Calming Oil (fragrance).
7. Continue stirring until bottling.
8. Optionally, the resultant formulation is separated by size-exclusion chromatography (e.g. HPLC or FPLC) and the fraction representing the solubilized Aspirin in the dermal and/or transdermal liquid having a reduced particle size (e.g. a particle size of less than or equal to 13 nm, 12 nm, 11 nm, 10 nm, 9 nm, 8 nm, 7 nm, 6 nm, or 5 nm) is isolated from the non-solubilized Aspirin (having a particle size of greater than 13 nm, 12 nm, 11 nm, 10 nm, 9 nm, 8 nm, 7 nm, 6 nm, or 5 nm).
9. Optionally, a cream, rinse, hydrogel, serum, lotion, gel, paste or puddy can be obtained by adding an appropriate amount of one or more viscosity-increasing agents, such as a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose.

Additional NSAID, acetaminophen, and insulin formulations were made using the approach described above with the following modifications:

Acetaminophen 2.2% formulation: Substitute 2.2% Acetaminophen for 2.2% aspirin.

Naproxen 2.2% formulation: Substitute 2.2% Naproxen for 2.2% aspirin.

Ketoprofen 2.2% formulation: Substitute 2.2% Ketoprofen for 2.2% aspirin.

Ibuprofen 2.2% formulation: Substitute 2.2% ibuprofen for 2.2% aspirin.

Insulin 2.2% formulation: Substitute 2.2% insulin for 2.2% aspirin.

The viscosity of a sample of the 2.2% liquid aspirin formulation was measured (at ambient room temperature) using a Brookfield Model LV viscometer (Spindle #6 at Speed 3). The viscosity of the formulation was found to be only 20 cP. For reference, the viscosity of water is approximately 1 cP. The viscosity value for the 2.2% liquid aspirin formulation was compared a sample of Thermazene™ (having a viscosity of 192,000 cP) using a TA Instruments Rheometer Model AR1000. Thermazene™ is an Over-The-Counter (or OTC) topical antimicrobial drug product, manufactured by Ascend Kendall Healthcare. Thermazene™ is sold as a soft, water-dispersible cream containing 1% silver sulfadiazine (claimed to be in micronized form) and used as an adjunct for the prevention and treatment of wound sepsis in patients with second and third degree burns. The exceptionally low viscosity of the 2.2% liquid aspirin formulation provides evidence that upon application to the skin, the formulation disperses as a thin film, which allows rapid diffusion of the active ingredient (i.e., Aspirin).

In a separate set of experiments, the contact angle of distilled/deionized water on a quartz plate substrate (at ambient room temperature) was compared to the contact angle of the liquid aspirin 2.2% formulation set forth above using a Krüss Model DSA 10 contact angle goniometer (see FIGS. 1A and 1B). The contact angle of the water under these conditions was found to be about 15°; however, it was not possible to measure the contact angle of the liquid aspirin 2.2% formulation set forth above because it wetted and spread too rapidly over the quartz plate resulting in too thin a film. This result was also confirmed from a spreading experiment, wherein 0.02 mL drop of each liquid (i.e. water and the liquid aspirin 2.2% formulation set forth above) was placed, using a glass syringe, onto a horizontal quartz plate (see FIGS. 2A and 2B). It was evident from the photomicrograph pictures that the liquid aspirin spread 4× more than pure water.

Accordingly, these results provide evidence that the liquid aspirin 2.2% formulation set forth above promotes deep penetration into human skin because of: (i) the low viscosity characteristics of the formulation, (ii) its ability to significantly reduce particle size (see Example 4) and enhance dispersion (e.g., to dramatically increase the solubility of aspirin) and (iii) its ability to efficiently (and rapidly) wet and spread over a surface.

Example 2

Additional NSAID transdermal and/or dermal compositions (e.g., liquids) can be readily prepared following the approach described in Example 1 with the following modifications.

Diclofenac Sodium 2.2% formulation: Substitute 2.2% Diclofenac Sodium for 2.2% aspirin.

Diclofenac Epolamine 2.2% formulation: Substitute 2.2% Diclofenac Epolamine for 2.2% aspirin.

Salicylic Acid 2.2% formulation: Substitute 2.2% Salicylic Acid for 2.2% aspirin.

Indomethicin 2.2% formulation: Substitute 2.2% Indomethicin for 2.2% aspirin.

Etodolac 2.2% formulation: Substitute 2.2% Etodolac for 2.2% aspirin.

Ketorolac 2.2% formulation: Substitute 2.2% Ketorolac for 2.2% aspirin.

Meloxicam 2.2% formulation: Substitute 2.2% Meloxicam for 2.2% aspirin.

Piroxicam 2.2% formulation: Substitute 2.2% Piroxicam for 2.2% aspirin.

Nabumetone 2.2% formulation: Substitute 2.2% Nabumetone for 2.2% aspirin.

For transdermal and/or dermal compositions (e.g., liquids) with higher concentrations of NSAIDs, acetaminophen, or insulin, e.g., 4.4% or 6.6% or higher concentration of active ingredient, the amount of water added is reduced accordingly, but the additional components in the mixture are added as described in the same amount. Similarly, should a greater or less concentration of alcohol or ethoxylated oil be desired, the differences in volume can be accommodated by altering the amount of water added so as to maintain the same total volume, as mentioned previously.

Example 3

A prior art dermal and/or transdermal composition (liquid) for use in comparative particle size and stability studies is prepared as follows:

Liquid Aspirin 2.2% (Prior art) Formulation (Quantity=100 g, which is approximately 100 mL).

Perform the following steps in order:

1. Bring 2.2±0.1 g USP grade aspirin into solution with 37.7 ml (approximately 38%) of distilled or deionized water.
2. Add 50 g of 200 Proof Ethyl Alcohol (approximately 50%) mixing continuously with a stir bar.
3. Slowly add 10 g (approximately 10%) of macadamia nut oil having 16 ethoxylations per molecule while mixing.

4. Once the emulsion has formed, add 0.13 g Peace & Calming Oil (fragrance dropwise.
5. Continue stirring until bottling.
6. Optionally, a cream, rinse, hydrogel, serum, gel, lotion, paste or puddy can be obtained by adding an appropriate amount of one or more viscosity-increasing agents such as, a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose.

Additional prior art NSAID, acetaminophen, and insulin formulations can be made using the approach described above with the following modifications:

Acetaminophen 2.2% formulation: Substitute 2.2% Acetaminophen for 2.2% aspirin.

Naproxen 2.2% formulation: Substitute 2.2% Naproxen for 2.2% aspirin.

Ketoprofen 2.2% formulation: Substitute 2.2% Ketoprofen for 2.2% aspirin.

Ibuprofen 2.2% formulation: Substitute 2.2% ibuprofen for 2.2% aspirin.

Insulin 2.2% formulation: Substitute 2.2% insulin for 2.2% aspirin.

These prior art formulations can be used to compare the particle size, stability, and efficacy of the inventive formulations provided in Examples 1 and 2.

Example 4

The particle size of aspirin (dry powder) and the aspirin diluted in the dermal and/or transdermal liquid formulation set forth in Example 1 were compared. Two studies were carried out to determine the particle size (and distribution) of samples of: (i) the formulation of Example 1, lacking only the aspirin (delivery system control), (ii) the formulation of Example 1, including the aspirin (experimental) and (iii) pure (dry) aspirin (control). The analysis revealed that the Z-average (Z-Avg) size as determined by Dynamic Light Scattering (DLS) measurements for the formulation of Example 1 containing the aspirin was 12.3 nanometers ($10^{-9}$), which was very similar to the measurements obtained for the formulation of Example 1, lacking only the aspirin (delivery system control, which measured 15.9 nanometers). In contrast, the pure (dry) Aspirin was measured at an average "particle size" of 670 microns ($10^{-6}$); which is more than 10,000 times larger than the aspirin present in the formulation set forth in Example 1 (the formulation containing aspirin). These results provide evidence that the aspirin was solubilized (at the molecular level) within the carrier system comprising the ethanol, ethoxylated oil, and water.

Example 5

The liquid aspirin 2.2% formulation set forth in Example 1 is analyzed for shelf-life/stability. Stability of the aspirin when it is disposed in a liquid is a particular problem for aspirin-based liquid formulations because aspirin is very susceptible to hydrolysis. The formulation of Example 1 creates a favorable environment for aspirin stability. Because the water is added last in the manufacturing method, the water can be excluded from the interior of the emulsified particles, wherein the aspirin is incorporated. It is contemplated that the methodology set forth in Example 1 reduces hydrolysis of the aspirin, and thus increases stability of the formulation and improves shelf-life of the product.

Example 6

Safety of Liquid NSAIDs in Humans. Topical administration of a liquid formulation comprising an NSAID requires a very small dosage of the NSAID, as compared to a typical oral dose of NSAID. Five subjects were given a single one-gram (approximately 1 ml) application of 2.2% liquid aspirin (formulation from Example 1) and the amount of aspirin in their blood was determined (in triplicate) at 15 and 30 minutes and again at one and three hours after topical application. Under these conditions, no aspirin or salicylates were detected in the blood plasma among all five subjects, demonstrating very low, if any, systemic exposure. The liquid aspirin 2.2% formulation set forth in Example 1 was also tested for skin irritation and allergenicity with a human repeat insult patch test (HRIPT). Irritation and allergenicity were tested separately, each on 50 human subjects over a six week period. No skin irritation or allergic reactions were observed during the course of the trial on any of the 50 human subjects tested.

Example 7

Efficacy of Liquid NSAIDs in Humans. A clinical study will be performed to evaluate the ability of the NSAID and/or acetaminophen formulations set forth in Example 1 to effectively deliver a therapeutically effective amount of the NSAID and/or acetaminophen across the skin of a subject so as to provide therapeutic benefit. The NSAID and/or acetaminophen formulations set forth in Example 1 are administered to subjects suffering from degenerative arthritis over 10 days. The test groups are divided as follows: (i) a control topical agent lacking NSAID or acetaminophen; (ii) an NSAID and/or acetominophen formulation set forth in Example 1, (iii) an NSAID and/or acetaminophen formulation prepared in accordance with Example 3 (prior art control), and (vi) an oral NSAID or acetaminophen dosage. Participants are asked to fill out a daily survey detailing amount of pain relief and noticeable side-effects. It is expected that the NSAID and/or acetaminophen formulations set forth in Example 1 will provide faster pain relief and greater reduction in pain for a prolonged period than the NSAID and/or acetaminophen formulations set forth in Example 3.

Example 8

In this example, the particle size of acetaminophen, ibuprofen, ketoprofen, naproxen, and insulin within the dermal and/or transdermal liquid, prepared in accordance with the teachings of Example 1 ("Liquid Acetaminophin," "Liquid ibuprofen," "Liquid insulin," "Liquid ketoprofen," and "Liquid naproxen"), were compared to the particle size of dry acetaminophen, dry ibuprofen, dry ketoprofen, and dry naproxen powder and a suspension of insulin in distilled water. As described in greater detail below, based on Dynamic Light Scattering measurements, after formulation in accordance with the methods described in Example 1, greater than 90% of the acetaminophen, ibuprofen, ketoprofen, naproxen, and insulin particles were less than 13 nm in size, when a volume-weighted particle size distribution calculation was used.

Materials:

The active ingredients (Neat API) evaluated were: Acetaminophen, Ibuprofen, Insulin, Ketoprofen, Naproxen.

All active ingredients were supplied as dry powders except for the insulin, which was supplied as an aqueous solution/suspension. The corresponding liquid formulations comprising acetaminophen, ibuprofen, insulin, ketoprofen, and naproxen, prepared as described in Example 1 (Liquid API), were supplied in a roller bottle.

Methods:

Sample Preparation.

Neat API: For optical microscopic/image analysis examination the material was used as received. A small aliquot was placed on a clean microscope slide and a clean glass coverslip placed on top.

For particle size analysis, by laser diffraction (LD), a small sample of the dry powder was dispersed into cyclohexane with sonication and then diluted to an appropriate signal level.

Liquid API: For particle size analysis by dynamic light scattering (DLS), a sample was retrieved from the roller bottle and measured directly.

Instrumentation

The optical microscope was a Zeiss Model Std 25 fitted with a 40× objective. The particle size analyzers were the Horiba LA 950 (LD) and a Malvern NanoSizer 90Z (DLS). The Raman spectrometer was a Horiba XploRA Raman Microscope.

Results and Discussion:

Sample 1: Acetaminophen (A) Neat API:

Optical Microscopic Examination

A visual image was obtained (FIG. 3A) from which it can be clearly seen that the particle size distribution (PSD) of the Acetominophen dry powder material is very broad—estimates of size range from around one or two microns (μm) to over 100 μm depending upon the dimension measured.

Particle Size Analysis by Laser Diffraction

The results of particle size distribution measurements are shown in FIG. 3B and are summarized in Table 1A.

TABLE 1A

| Particle Size (μm) | | |
|---|---|---|
| Mean | Mode | Median |
| 58 | 42 | 44 |

FIG. 3B shows a very broad irregular distribution ranging from about 1 μm to ca 400 μm. Given that the LD method provides only an "equivalent spherical diameter" size, the PSD data so obtained are consistent with the estimates from the microscopic examination.

(B) Liquid API

Particle Size Analysis by Dynamic Light Scattering

The data are summarized in Table 1B.

TABLE 1B

| "Liquid Acetominophen" | | | | | |
|---|---|---|---|---|---|
| | Particle Size (nm) Modes | | | | |
| Intensity-weighted | 9.3 | 15.9 | 1500 | 2000 | 6500 |
| Volume-weighted | 9.4 | — | 1700 | — | 5400 |
| Number-weighted | 8.0 | — | — | — | — |

In DLS measurements, the raw light "intensity" data is weighted (i.e. influenced and emphasized) by the 6th power of the particle diameter. As such it is very sensitive to any larger particles within a particle size distribution (PSD). The intensity data for the Liquid Acetominophen reveals multiple peaks and indicates the presence of particles as large as 6.5 μm in size. The measured polydispersity index (PDI) (which can be thought of as a variance) was 1.00 suggesting an extremely broad particle size distribution and this is clearly concordant with the size data in Table 1B. To put the PDI value into perspective a "narrow" distribution would typically have a PDI<0.03. However, the actual amount of these larger fractions is very small indeed as will be illustrated in the following.

For pharmaceutical applications, it is usual to express particle size results in terms of a "volume-weighted" size because dosage is usually by mass or volume. DLS intensity data can be transformed mathematically into volume data and, so doing, the resulting PSD is shown in FIG. 3C. Now we can see that these larger "fractions" disappear when the data is converted to volume-weighting and this is consistent with the fact that there was very little present. Indeed, on a volume-weighted basis, >99% of the Acetominophen particles are <10 nm in size. If the raw data is further transformed to a number-weighting it can be seen that there are so few particles>8 nm that they cannot be statistically counted.

Two conclusions can be drawn from inspection of the DLS data. The first is that the "size" of the Liquid Acetominophen formulation prepared as set forth in Example 1 is similar to that found with the previous measurements of samples of the delivery system alone (e.g., the liquid comprising the ethanol, ethoxylated oil, and water in the absence of the active ingredient).

The intensity-weighted data determined for the original delivery system alone (e.g., the liquid comprising the ethanol, ethoxylated oil, and water in the absence of the active ingredient, or otherwise referred to herein as "DermX® Megaspheres™") also indicated the presence of a small fraction of much larger particles. Thus, it was decided to reevaluate a second sample of DermX® Megaspheres™ alone. The results are summarized in Table 1C and the volume-weighted PSD is shown in FIG. 3D.

TABLE 1C

| DermX ® Megaspheres ™ | | | | |
|---|---|---|---|---|
| | Particle Size (nm) Modes | | | |
| Intensity-weighted | — | 14.6 | 1150 | 5300 |
| Volume-weighted | — | 12.7 | 1240 | — |
| Number-weighted | 7.0 | 12.0 | — | — |

Again, it was found that the "size" of the delivery system alone (DermX® Megaspheres™) was consistent with that for the Liquid Acetominophen formulation prepared as set forth in Example 1.

The second conclusion is, as a consequence (compared with the size measurements on the bulk dry powder sample), that the Acetominophen powder material has been solubilized within the DermX® Megaspheres™ carrier system. This will result in a much more efficient delivery of acetominophen.

It is believed that the "Liquid Acetominophen" is, indeed, Active Pharmactical Ingredient (or API) solubilized within DermX® Megaspheres™. To confirm this, a Raman spectroscopic examination of the neat acetaminophen, the DermX® Megaspheres™ by itself (no API present) and the "Liquid Acetaminophen" was conducted. A comparison of the three spectra shown in FIG. 3E (RED: neat acetaminophen; BLUE: DermX® Megaspheres™ only; Green: Liquid API) clearly demonstrates that the Liquid API is solubilized Acetaminophen.

Sample 2: Ibuprofen (A) Neat API:

Optical Microscopic Examination

A visual image was obtained (FIG. 4A) from which it can be seen that the PSD or the dry powder Ibuprofen is very broad—estimates of size range from around 10 µm to over 100 µm depending upon the dimension measured.

Particle Size Analysis by Laser Diffraction

The results of particle size distribution measurements are shown in FIG. 4B and are summarized in Table 2A.

TABLE 2A

| Particle Size (µm) | | |
|---|---|---|
| Mean | Mode | Median |
| 78 | 72 | 70 |

FIG. 4B shows a very broad irregular distribution ranging from about 2 µm to about 300 µm. Given that the LD method provides only an "equivalent spherical diameter" size, the PSD data so obtained are consistent with the estimates from the microscopic examination above.

(B) Liquid API

Particle Size Analysis by Dynamic Light Scattering

The data are summarized in Table 2B.

TABLE 2B

"Liquid Ibuprofen"

| | Particle Size (nm) Modes | | |
|---|---|---|---|
| Intensity-weighted | 12.3 | 1760 | 5500 |
| Volume-weighted | 9.4 | 1900 | 5500 |
| Number-weighted | 8.0 | — | — |

The intensity data for the Liquid Ibuprofen reveals multiple peaks and indicates the presence of particles as large as 5.5 µm in size. The measured PDI was 0.94 suggesting an extremely broad PSD and this is clearly concordant with the size data in Table 2B. The actual amount of these larger fractions is very small as can be seen from the volume-weighted PSD (FIG. 4C); 99.5% of the Ibuprofen particles are <10 nm in size. On a number-weighted basis there are so few particles>8 nm that they cannot be statistically counted.

Two conclusions can be drawn from inspection of the DLS data. The first is that the "size" of the Liquid Ibuprofen is similar to that found with the measurement of the DermX® Megaspheres™ by itself (no API) (FIG. 3D). The second conclusion is that the Ibuprofen powder has been solubilized within the DermX® Megaspheres™ carrier system (and confirmed by Raman spectroscopic analysis—FIG. 4D). This will result in a much more efficient delivery of Ibuprofen.

Sample 3: Insulin (A) Neat API:

Optical Microscopic Examination

No visual imaging was attempted because the insulin was supplied as a solution/suspension and it was assumed that the particle size would be below the limits of detection by the human eye (ca 1 µm).

Particle Size Analysis by Dynamic Light Scattering

After initial investigation it was decided that Laser Diffraction was not considered to be the most appropriate technique to measure the particle size for this insulin solution/suspension. Accordingly, DLS was chosen and the results of the analysis are shown in FIGS. 5A and 5B and are summarized in Table 3A.

TABLE 3A

"Neat Insulin"

| | Particle Size (nm) Modes | | | |
|---|---|---|---|---|
| Intensity-weighted | 6.0 | 130 | 1000 | 5000 |
| Volume-weighted | 5.2 | 91 | — | 4300 |

The intensity data for the supplied Insulin solution/suspension reveals multiple peaks and indicates the presence of particles as large as 5 µm in size. The measured polydispersity index (PDI) was 0.97 suggesting an extremely broad PSD and this is clearly concordant with the size data in Table 3A. The actual amount of these larger fractions is small as can be seen from the volume-weighted PSD (FIG. 4C); 99.9% of the Insulin particles are around 6 nm in size.

Given these measured sizes, we postulate that the "neat insulin" supplied is virtually a solution (a sugar molecule has a dimension of 3 nm) containing some suspended particle matter. The latter material is unlikely to be insulin particles because insulin is known to be fairly soluble in water.

(B) Liquid API

Particle Size Analysis by Dynamic Light Scattering

The data are summarized in Table 3B.

TABLE 3B

"Liquid Insulin"

| | Particle Size (nm) Modes | | |
|---|---|---|---|
| Intensity-weighted | 2.9 | 14.4 | 4600 |
| Volume-weighted | 2.5 | 11.5 | 4900 |
| Number-weighted | 2.5 | 4.9 | — |

The intensity data for the Liquid Insulin reveals multiple peaks and indicates the presence of particles as large as 5 µm in size. The measured polydispersity index (PDI) was 0.26 suggesting a very broad PSD and this is clearly concordant with the size data in Table 3B. The actual amount of these larger fractions is small as can be seen from the volume-weighted PSD (FIG. 5C). On a number-weighted basis>90% of the Insulin "particles" are <3 nm.

Two conclusions can be drawn from inspection of the DLS data. The first is that the "size" of the Liquid Insulin is similar to that found with the measurement of the DermX® Megaspheres™ by itself (no API) (FIG. 3D). This is not surprising since the neat Insulin was essentially a solution. The second conclusion is that the Insulin has been more efficiently solubilized within the DermX® Megaspheres™ carrier system and this will result in a much more efficient delivery of Insulin.

It was not possible to carry out a Raman Spectrum analysis because the signal from even the "neat Insulin" was too weak—possibly because the concentration of insulin was very low. Nevertheless, by analogy with the previous results for the Acetaminophen and Ibuprofen, it seems reasonable that the "Liquid Insulin" does contain API.

Sample 4: Ketoprofen
(A) Neat API:
Optical Microscopic Examination

A visual image was obtained (FIG. 6A) from which it can be clearly seen that the PSD of the dry powder Ketoprofen is broad—estimates of size range from singlet particles around 10 μm to aggregates between 50 μm and over 100 μm.

Particle Size Analysis by Laser Diffraction

The results of particle size distribution measurements are shown in FIG. 6B and are summarized in Table 4A.

TABLE 4A

| Particle Size (μm) | | |
|---|---|---|
| Mean | Mode | Median |
| 34 | 28 | 27 |

FIG. 6B shows a very broad distribution with sizes ranging from about 1 μm to ca 200 μm, with the majority being about 30 μm. Given that the LD method provides only an "equivalent spherical diameter" size, the PSD data so obtained are consistent with the estimates from the microscopic examination above.

(B) Liquid API
Particle Size Analysis by Dynamic Light Scattering

The data are summarized in Table 4B.

TABLE 4B

| "Liquid Ketoprofen" | | | | | |
|---|---|---|---|---|---|
| | Particle Size (nm) Modes | | | | |
| Intensity-weighted | — | — | 12.9 | 1600 | 5000 |
| Volume-weighted | 2.2 | 5.5 | 9.9 | 1600 | 5200 |
| Number-weighted | 2.2 | 5.5 | — | — | — |

The intensity data for the Liquid Ketoprofen reveals multiple peaks and indicates the presence of particles as large as 6 μm in size. The measured polydispersity index (PDI) was 0.73 suggesting a broad PSD and this is clearly concordant with the size data in Table 4B. The actual amount of these larger fractions is small as can be seen from the volume-weighted PSD (FIG. 6C). On a number-weighted basis>90% of the Ketoprofen "particles" are <6 nm.

Two conclusions can be drawn from inspection of the DLS data. The first is that the "size" of the Liquid Ketoprofen is similar to that found with the measurement of DermX® Megaspheres™ by itself (no API) (FIG. 3D). The second conclusion is that the Ketoprofen powder has been solubilized within the DermX® Megaspheres™ carrier system (and confirmed by Raman spectroscopic analysis—FIG. 6D). This will result in a much more efficient delivery of Ketoprofen.

Sample 5: Naproxen
(A) Neat API:
Optical Microscopic Examination

A visual image was obtained (FIG. 7A) from which it can be clearly seen that the PSD of the dry powder Naproxen is broad. There are lots of singlet particles of only a few microns in size and aggregates as large as 100 μm.

Particle Size Analysis by Laser Diffraction

The results of particle size distribution measurements are shown in FIG. 7B and are summarized in Table 5A.

TABLE 5A

| Particle Size (μm) | | |
|---|---|---|
| Mean | Mode | Median |
| 23 | 19 | 23 |

FIG. 7B shows a very broad symmetrical distribution ranging from about 2 μm to over 200 μm, with the majority being around 20 μm. Given that the LD method provides only an "equivalent spherical diameter" size, the PSD data so obtained are consistent with the estimates from the microscopic examination above.

(B) Liquid API
Particle Size Analysis by Dynamic Light Scattering

The data are summarized in Table 5B.

TABLE 5B

| "Liquid Naproxen" | | | | |
|---|---|---|---|---|
| | Particle Size (nm) Modes | | | |
| Intensity-weighted | 0.7 | 4.9 | 14.2 | 600 |
| Volume-weighted | 0.7 | 4.8 | 12.3 | — |
| Number-weighted | 0.7 | 4.5 | 11.3 | — |

The intensity data for the Liquid Naproxen reveals multiple peaks and indicates the presence of particles as large as 600 nm in size. The measured polydispersity index (PDI) was 0.50 suggesting a broad PSD (but it is the narrowest of all the Liquid API systems) and this is clearly concordant with the size data in Table 5B. The actual amount of this large size fraction is very small as can be seen from the volume-weighted PSD (FIG. 6C). On a number-weighted basis 99.9% of the particles are <12 nm.

Two conclusions can be drawn from inspection of the DLS data. The first is that the "size" of the Liquid Naproxen is similar to that found with the measurement of DermX® Megaspheres™ by itself (no API) (FIG. 3D). The second conclusion is that the Naproxen powder has been well solubilized within the DermX® Megaspheres™ carrier system (and confirmed by Raman spectroscopic analysis—FIG. 7D). This will obviously result in a much more efficient delivery of Naproxen.

As detailed above, the DLS particle size measurements for the Liquid API systems studied were very similar to the data obtained both for a previous batch and also a current batch of the DermX® Megaspheres™ carrier system alone. In all cases, the API in question was solubilized within the DermX® Megaspheres™ carrier system. This will result in a much more efficient delivery of each API.

Example 9

In one set of experiments, the transdermal and/or dermal liquid formulations prepared in accordance with the teachings of Examples 1 and 2 are compared to the prior art liquid formulations prepared in accordance with the teachings of Example 3 and the particle size and stability evaluations detailed in Examples 4, 5, and 8. In these experiments, it is found that the transdermal and/or dermal liquid formulations prepared in accordance with the teachings set forth in Examples 1 and 2 have greater than or equal to 90%, 91%, 92%, 93%, 94%, 95%, 96%, 97%, 98%, or 99% of the particles of the active ingredient with a particle size that is less than or equal to 13 nm, 12 nm, 11 nm, 10 nm, 9 nm, 8 nm, 7 nm, 6 nm, or 5 nm, as determined by Dynamic Light Scattering, using a volume-weighted particle size distribution calculation method. The transdermal and/or dermal liquid formulations prepared in accordance with the teachings set forth in Examples 1 and 2 also have long term stability to degradation and hydrolysis, as determined for example by HPLC analysis of the active ingredients after exposure to 90 days at 40° C./75% relative humidity followed by 30 days at 25° C.

In contrast, it is contemplated that the liquid formulations prepared in accordance with the teachings set forth in Example 3 will have less than 90%, 91%, 92%, 93%, 94%, 95%, 96%, 97%, 98%, or 99% of the particles of the active ingredient with a particle size that is less than or equal to 13 nm, 12 nm, 11 nm, 10 nm, 9 nm, 8 nm, 7 nm, 6 nm, or 5 nm, as determined by Dynamic Light Scattering, using a volume-weighted particle size distribution calculation method. The liquid formulations prepared in accordance with the teachings set forth in Example 3 are also expected to be less stabile to degradation and hydrolysis, as determined by HPLC analysis of the active ingredients after exposure to 90 days at 40° C./75% relative humidity followed by 30 days at 25° C., than the transdermal and/or dermal liquid formulations prepared in accordance with the teachings set forth in Examples 1 and 2. Accordingly, these experiments will demonstrate that reducing the contact of the active ingredient with water during the manufacturing of the transdermal and/or dermal liquid reduces particle size of the active ingredient, improves the homogeneity of size of the population of particles in the liquid, and improves the stability of the active ingredient in the liquid.

Example 10

Additional transdermal and/or dermal liquid formulations containing NSAIDs (e.g., aspirin, naproxen, ibuprofen, and/or ketoprofen), acetaminophen, and/or insulin will be created following the procedures set forth in Examples 1 and 2; however, the amount of ethoxylated oil (e.g., macadamia nut oil having 10, 11, 12, 13, 14, 15, 16, 17, 18, 19, 20, 21 or 22 ethoxylations per molecule) used in the formulations will vary. The transdermal and/or dermal liquid formulations, which will be made for these experiments may have, for example, 3.0%, 4.0%, 5.0%, 6.0%, 7.0%, 8.0%, 9.0%, 10.0%, 11.0%, 12.0%, 13.0%, 14.0%, 15.0%, 16.0%, 17.0%, 18.0%, 19.0%, 20.0%, 21.0%, 22.2%, 23.0%, 24.0%, or 25.0% of the total volume or weight of such ethoxylated oil. The amount of water that will be added to the formulations will also vary accordingly so as to accommodate the increase or decrease in the amount of ethoxylated oil in the preparation. These transdermal and/or dermal liquid formulations will then be evaluated in the particle size and stability tests detailed in Examples 4, 5, and 8.

It will be found that transdermal and/or dermal liquid formulations having an amount of ethoxylated oil in the preparation that is 10.0%, 11.0%, 12.0%, 13.0%, 14.0%, 15.0%, 16.0%, 17.0%, 18.0%, 19.0%, or 20.0% of the total volume or weight of the transdermal and/or dermal liquid will have greater than or equal to 90%, 91%, 92%, 93%, 94%, 95%, 96%, 97%, 98%, or 99% of the particles of the active ingredient with a particle size that is less than or equal to 13 nm, 12 nm, 11 nm, 10 nm, 9 nm, 8 nm, 7 nm, 6 nm, or 5 nm, as determined by Dynamic Light Scattering, using a volume-weighted particle size distribution calculation method. These transdermal and/or dermal liquid formulations will also have long term stability to degradation and hydrolysis, as determined for example by HPLC analysis of the active ingredients after exposure to 90 days at 40° C./75% relative humidity followed by 30 days at 25° C.

In contrast, it is expected that the transdermal and/or dermal liquid formulations having an amount of ethoxylated oil in the preparation that is 7.0%, 8.0%, 9.0% or 21.0%, 22.0%, 23.0%, 24.0%, or 25.0% of the total volume or weight of the transdermal and/or dermal liquid will have less than 90%, 91%, 92%, 93%, 94%, 95%, 96%, 97%, 98%, or 99% of the particles of the active ingredient with a particle size that is less than or equal to 13 nm, 12 nm, 11 nm, 10 nm, 9 nm, 8 nm, 7 nm, 6 nm, or 5 nm, as determined by Dynamic Light Scattering, using a volume-weighted particle size distribution calculation method. The transdermal and/or dermal liquid formulations having an amount of ethoxylated oil in the preparation that is 3.0%, 4.0%, 5.0%, 6.0%, 7.0%, 8.0%, 9.0% or 21.0%, 22.2%, 23.0%, 24.0%, or 25.0% of the total volume or weight of the transdermal and/or dermal liquid are also expected to be less stable and more susceptible to degradation and hydrolysis, as determined by HPLC analysis of the active ingredients after exposure to 90 days at 40° C./75% relative humidity, than the transdermal and/or dermal liquid formulations having an amount of ethoxylated oil in the preparation that is 10.0%, 11.0%, 12.0%, 13.0%, 14.0%, 15.0%, 16.0%, 17.0%, 18.0%, 19.0%, or 20.0% of the total volume or weight of the transdermal and/or dermal liquid. Accordingly, these experiments will demonstrate that when the amount of ethoxylated oil in a transdermal and/or dermal liquid prepared as described in Examples 1 and 2 is 10.0%, 11.0%, 12.0%, 13.0%, 14.0%, 15.0%, 16.0%, 17.0%, 18.0%, 19.0%, or 20.0% a reduced particle size of the active ingredient is generated, the homogeneity of size of the population of particles in the transdermal and/or dermal liquid is improved, and the stability of the active ingredient in the liquid is improved, as compared to transdermal and/or dermal liquids prepared in accordance with the methods of Example 1 and 2, wherein the amount of ethoxylated oil is 7.0%, 8.0%, 9.0% or 21.0%, 22.0%, 23.0%, 24.0%, or 25.0% of the total volume or weight of the transdermal and/or dermal liquid.

Example 11

Efficacy of Liquid Insulin in Rats. Normal rats (with a shaved portion on their dorsal surface) will be anesthetized with a mixture of xylazine and ketamine to elevate their blood glucose levels. The elevated levels of d-glucose that occur in response to anesthesia provide an optimal model system to measure the efficacy of topically delivered insulin. This animal model mimics the hyperglycemic state seen in diabetic animals and humans. The anesthetized rats will be divided into three groups: (i) rats treated with a Liquid Insulin formulation prepared in accordance with the teachings of Example 1; (ii) rats given a control formulation lacking insulin (the DermX® delivery system without insulin); and (iii) rats treated with a Liquid Insulin formulation prepared in accordance with the teachings in Example 3 (prior art formulation).

Each group will receive the same topical "dose" and the change in blood glucose levels detected in the animals will reflect the effect of insulin absorbed transdermally (i.e., the amount of insulin absorbed into systemic circulation). It is expected that the rats that are provided the Liquid Insulin formulation prepared in accordance with the teachings of Example 1 will have a greater amount of insulin detected in their bodies and will experience a greater drop in blood glucose levels than the rats given the control formulation lacking insulin (the DermX® delivery system without insulin); and the rats treated with the Liquid Insulin formulation prepared in accordance with the teachings in Example 3 (prior art formulation).

Example 12

Relevance of Sequential Addition of Components. Preparations useful for the delivery of an active ingredient were prepared as indicated below. Formulations 1, 2, 3, and 4 comprised Alcohol (50%), Aspirin (2.2%), PEG-16 Macadamia Glycerides (10%), water (37.67%), and fragrance (0.13%), to a total of 100%. Formulation 1C comprised Alcohol (50%), Aspirin (2.2%), PEG-16 Macadamia Glycerides (0%), water (47.67%), and fragrance (0.13%), to a total of 100%, lacking PEG-16 Macadamia Glycerides. Formulations 1, 2, 3, and 4 comprise the same constituents but differ in the order in which each constituent is added to assemble the formulation.

In formulation 1, the preparation was constituted by the following steps in order: (a) mixing an amount of an active ingredient (Aspirin, 2.2% of the final formulation) with an alcohol, which is present at a final concentration of 30-70% (50% in the present example) by total weight or total volume of the transdermal and/or dermal composition; (b) adding an ethoxylated oil, PEG-16 Macadamia Glycerides, which is present at a final concentration of 2-25% (10% in the present example) by total weight or total volume of the transdermal and/or dermal composition, to the mixture of (a); (c) adding an amount of water (37.67%), to bring the transdermal and/or dermal composition to its final volume to the mixture of (a) and (b); and (d) adding a minimal proportional volume (0.13%) of a fragrance to the mixture of (a), (b) and (c).

In formulation 1c, the formulation was constituted by the following steps in order: (a) mixing an amount of an active ingredient (Aspirin, 2.2% of the final formulation) with an alcohol, which is present at a final concentration of 30-70% (50% in the present example) by total weight or total volume of the transdermal and/or dermal composition; (b) adding an amount of water (47.67% in this example) to bring the transdermal and/or dermal composition to its final volume; and adding a minimal proportional amount (0.13%) of a fragrance. Formulation 1c lacks PEG-16 Macadamia Glycerides.

In formulation 2, the formulation was constituted by the following steps in order: (a) mixing an amount of an active ingredient (Aspirin, 2.2% of the final formulation) with an amount of water (37.67%); (b) adding an alcohol, which is present at a final concentration of 30-50% (50% in the present example) by total weight or total volume of the transdermal and/or dermal composition to the mixture of (a); (c) adding an ethoxylated oil, PEG-16 Macadamia Glycerides, which is present at a final concentration of 2-25% (10% in the present example) by total weight or total volume of the transdermal and/or dermal composition, to the mixture of (a) and (b); and adding a minimal proportional amount (0.13%) of a fragrance.

In formulation 3, the formulation was constituted by the following steps in order: (a) mixing an amount of water (37.67%) with an ethoxylated oil, PEG-16 Macadamia Glycerides, which is present at a final concentration of 2-25% (10% in the present example) by total weight or total volume of the transdermal and/or dermal composition; (b) mixing an amount of an active ingredient (Aspirin, 2.2% of the final formulation) to the mixture of (a); (c) adding a minimal proportional amount (0.13%) of a fragrance to the mixture of (a) and (b); and (d) adding an alcohol, which is present at a final concentration of 30-70% (50% in the present example) by total weight or total volume of the transdermal and/or dermal composition, to the mixture of (a), (b) and (c).

In formulation 4, the formulation was constituted by the following steps in order: (a) providing an amount of alcohol, which is present at a final concentration of 30-70% (50% in the present example) by total weight or total volume of the transdermal and/or dermal composition; (b) adding an ethoxylated oil, PEG-16 Macadamia Glycerides, which is present at a final concentration of 2-25% (10% in the present example) by total weight or total volume of the transdermal and/or dermal composition, to the mixture of (a); (c) adding an amount of water (39.87%) to mixture (a) and (b), to bring the transdermal and/or dermal composition to its final volume; and (d) adding a minimal proportional amount (0.13%) of a fragrance to mixture (a), (b) and (c). Formulation 4 lacks Aspirin.

Each formulation was constituted using the sequential formulation steps in order as indicated above. Images of these formulations were taken by light microscopy at 100× magnification, and are presented in FIGS. 8A-8F. A particle size distribution was determined for a sample of each formulation by Dynamic Light Scattering and the Z-avg in nanometers (nm) was determined. Similar measurements were made for Dry Aspirin.

The results are presented in Table 6, below.

TABLE 6

Particle Size Results

| Sample | Count Rate | Z-Avg (nm) | Intercept |
| --- | --- | --- | --- |
| Formulation 1 | 5.7 | 16.7 | 0.877 |
| Formulation 1c | 14.7 | 2239 | 0.915 |
| Formulation 2 | 8.3 | 122.8 | 0.918 |
| Formulation 3 | 13.4 | 348.2 | 1.2 |
| Formulation 4 | 26.5 | 132.5 | 1.0 |
| Dry Aspirin | Not Applicable | Not Applicable | Not Applicable |

Z-Avg (nm) is the product of the dynamic light scattering results, and represents the intensity weighted harmonic mean size of particles of each Particle Size.

As indicated in Table 6, addition of an ethoxylated oil, which is present at a final concentration of 2%-25% by total weight or total volume of the transdermal and/or dermal composition (PEG-16 Macadamia Glycerides at 10% in the present example), has a substantial impact on particle size as indicated by final Z-Avg values as measured by dynamic light scattering. Particle sizes for Formulation 1c were over 100× greater than those of Formulation 1, and were 6× to 18× larger than those of Formulations 2, 3, and 4. This indicated that addition of an ethoxylated oil, which is present at a final concentration of 2%-25% by total weight or total volume of the transdermal and/or dermal composition has a substantial impact on final particle size or volume.

Also as indicated above, this example provides evidence that the order of addition of the components has a substantial impact on particle size as indicated by final Z-Avg values as measured by dynamic light scattering. Particle sizes for Formulation 1 (constituted by practicing a method of making a transdermal and/or dermal composition (e.g., liquid) comprising the following steps in order: (a) mixing an amount of an active ingredient with an alcohol, which is present at a final concentration of 1%-70% (or more exemplary at 30%-70%, 30%-60%, or 40%-60%, or 45%-55%, or 50%) by total weight or total volume of the transdermal and/or dermal composition; (b) adding an ethoxylated oil, which is present at a final concentration of 2%-25% by total weight or total volume of the transdermal and/or dermal composition, to the mixture of (a); (c) optionally, adding an amount of water to mixture (a) and (b) to bring the transdermal and/or dermal composition to its final volume; and (d) optionally, adding a fragrance and/or one or more viscosity-increasing agents such as, a cellulose derivative that is selected from the group consisting of hydroxyethylcellulose, methylcellulose, hydroxypropyl cellulose, carboxymethyl cellulose, hydroxypropyl methyl cellulose (E464), and hydroxyethyl methyl cellulose to mixture (a), (b) and (c)), were substantially less than particle sizes for Formulations 2, 3, and 4, comprising the same constituents but assembled through a different order of constituent addition. Particle sizes for Formulations 2, 3, and 4 were greater than 7×, greater than 20×, and greater than 7×, respectively, larger than those of Formulation 1 in size as indicated by final Z-Avg values as measured by dynamic light scattering. Among the Formulations assayed, only Formulation 1 produced particles having a size below 100 nm as measured by Z-avg, the intensity weighted harmonic mean size of particles of each Particle Size.

What is claimed is:

1. A method of making a transdermal and/or dermal composition comprising the following steps in order:
   (a) mixing an amount of an active ingredient comprising particles with an alcohol; and
   (b) adding an ethoxylated oil selected from the group consisting of ethoxylated macadamia nut oil, ethoxylated meadowfoam oil, ethoxylated jojoba oil, and ethoxylated emu oil, which is present at a final concentration of 2%-18% by total weight or total volume of the transdermal and/or dermal composition, to the mixture of (a),
   wherein greater than 90% of the particles of the active ingredient in the composition made by the said method have a particle size that is equal to or less than 100, 90, 80, 70, 60, 50, 40, 30, 20, 19, 18, 17, 16, 15, 14, 13, 12, 11, 10, 9, 8, 7, 6, 5, or 4 nanometers, as determined by Dynamic Light Scattering, using a volume-weighted particle size distribution calculation method.

2. The method of claim 1, wherein the transdermal and/or dermal composition further comprises water.

3. The method of claim 2, wherein the transdermal and/or dermal composition further comprises one or more viscosity-increasing agents selected from the group consisting of hydroxyethylcellulose, methylcellulose, hydroxypropyl cellulose, carboxymethyl cellulose, hydroxypropyl methyl cellulose (E464), and hydroxyethyl methyl cellulose.

4. The method of claim 1, wherein the active ingredient is selected from the group consisting of a Non-Steroidal Anti-Inflammatory Drug (or NSAID), a drug, a protein, a polypeptide, a dietary supplement, an antioxidant, an amino acid, a sugar or a sugar-containing compound, a hormone, a hormone precursor, a hormone mimic, an antibiotic, and an anti-wrinkle agent.

5. The method of claim 4, wherein said active ingredient is a Non-Steroidal Anti-Inflammatory Drug (NSAID) selected from the group consisting of aspirin (acetylsalicylic acid), naproxen (2-(6-methoxynaphthalen-2-yl) propanoic acid), diclofenac (2-(2,6-dichloranilino) phenylacetic acid) (sodium and/or epolamine), ibuprofen (iso-butyl-propanoic-phenolic acid), ketoprofen ((RS) 2-(3-benzoylphenyl)-propionic acid), and acetaminophen (N-acetyl-para-aminophenol).

6. The method of claim 4, wherein said active ingredient is a hormone, hormone precursor, or a hormone mimic selected from the group consisting of insulin, dehydroepiandrosterone (DHEA), a human growth hormone (hGH), and erythropoietin (EPO).

7. The method of claim 1, wherein the active ingredient comprises one or more opioids, anti-depressants, anti-epileptic drugs, adjuvant medications, muscle relaxers, nerve ablation drugs, spinal cord stimulators, nutraceuticals, vitamins, minerals, neuropathy therapy drugs, male hormonal balancing drugs, female hormonal balancing drugs, or bioidentical hormones.

8. The method of claim 1, wherein said ethoxylated macadamia nut oil is an ethoxylated macadamia nut oil having 10, 11, 12, 13, 14, 15, 16, 17, 18, 19, 20, 21, 22, 23 or 24 ethoxylations per molecule.

9. The method of claim 1, wherein said alcohol is present at 1%-70% by total weight or total volume of the transdermal and/or dermal emulsion composition.

10. The method of claim 1, wherein the transdermal and/or dermal composition further comprises a fragrance.

11. The method of claim 2, wherein said ethoxylated oil is an ethoxylated macadamia nut oil having 16 ethoxylations per molecule.

12. The method of claim 4, wherein the active ingredient is an anti-wrinkle agent selected from the group consisting of collagen, elastin, a peptide, retinol, retinoic acid derivatives, hydroxy acids, alpha hydroxy acid, lactic acid, exfoliants, kinetins, and hyaluronic acid.

13. The method of claim 1, wherein the active ingredient is a polypeptide or protein.

14. The method of claim 1, wherein the active ingredient is an insulin, a collagen, an elastin, or a hyaluronic acid.

* * * * *